United States Patent
Van Ooijen et al.

(10) Patent No.: US 6,329,141 B1
(45) Date of Patent: Dec. 11, 2001

(54) METHODS FOR TRANSFORMING PHAFFIA STRAINS, TRANSFORMED PHAFFIA STRAINS SO OBTAINED AND RECOMBINANT DNA IN SAID METHODS

(75) Inventors: Albert Johannes Joseph Van Ooijen, Voorburg; Jan Cornelis Verdoes; Jan Wery, both of Wageningen, all of (NL)

(73) Assignee: DSM N.V., Ma Delft (NL)

( * ) Notice: Subject to any disclaimer, the term of this patent is extended or adjusted under 35 U.S.C. 154(b) by 0 days.

(21) Appl. No.: 09/091,725

(22) PCT Filed: Dec. 23, 1996

(86) PCT No.: PCT/EP96/05887

§ 371 Date: Nov. 19, 1998

§ 102(e) Date: Nov. 19, 1998

(87) PCT Pub. No.: WO97/23633

PCT Pub. Date: Jul. 3, 1997

(30) Foreign Application Priority Data

Dec. 22, 1995 (EP) .................................................. 95203620
Apr. 11, 1996 (EP) .................................................. 96200943

(51) Int. Cl.$^7$ .............................. C12Q 1/68; C12P 21/02
(52) U.S. Cl. .............................. 435/6; 435/69.1; 435/483; 435/200; 435/254.2; 435/320.1; 536/23.1; 536/24.1; 536/24.3; 536/24.5
(58) Field of Search .................. 435/254.2, 6, 320.1, 435/69.1, 200, 483; 536/23.1, 24.1, 24.3, 24.5

(56) References Cited

U.S. PATENT DOCUMENTS 5,840,528 * 11/1998 Van Ooyen ........................ 435/69.1

FOREIGN PATENT DOCUMENTS 0 120 551 B1 10/1984 (EP) .
0 164 556 B1 12/1985 (EP) .
0 509 707 A1 10/1992 (EP) .

OTHER PUBLICATIONS

Adrio, J.L. et al., "Transformation of the Astaxanthin–Producing Yeast *Phaffia rhodozyma*," *Biotechnology Techniques* (Jul. 1995) 9(7):509–512.

Botella, J.A. et al., "A cluster of structural and regulatory genes for light–induced carotenogenesis in *Myxococcus xanthus*," *Eur J Biochem* (1995) 233:238–248.

Boucherie, H. et al., "Differential synthesis of glyceraldehyde–3–phosphate dehydrogenase polypeptides in stressed yeast cells," *FEMS Microbiology Letters* (1995) 135:127–134.

Cryer, D.R. et al., "Isolation of Yeast DNA" in *Methods in Cell Biology* XII:39–44, Prescott, D.M. (ed.) Academic Press, New York, 1975.

McNally, M.T. et al., "Isolation and characterization of a Neurospora glucose–repressible gene," *Current Genetics* (1988) 14:545–551.

Faber, K.N. et al., "Highly–efficient electrotransformation of the yeast *Hansenula polymorpha*," *Current Genetics* (1994) 25:305–310.

B.D. Hames & S.J. Higgins Eds., 1985, IRL, Press Oxford.

Holland, J.P. et al., "The Primary Structure of a Glyceraldehyde–3–phosphate Dehydrogenase Gene from *Saccharomyces cerevisiae*," *Journal of Biological Chemistry* (1979) 254:9839–9845.

Hoshino T. et al., "Overproduction of Carotenoids in *Thermus thermophilus*," *Journal of Fermentation and Bioengineering* (1994) 77(4)423–424.

Jimenez, A. et al., "Expression of a transposable antibiotic resistance element in Saccharomyces," *Nature* (Oct. 30, 1980) 287:869–871.

Johnson, E.A. et al., "Simple Method for the Isolation of Astaxanthin from the Basidiomycetous Yeast *Phaffia rhodozyma*," *Applied Environmental Microbiology* (Jun. 1978) 35:1155–1159.

Johnston, S.A. et al., "Interaction of Positive and Negative Regulatory Proteins in the Galactose Regulon of Yeast," *Cell* (1987) 50:143–146.

Kolar, M. et al., "Transformation of *Penicillium chrysogenum* using dominant selection markers and expression of an *Escherichia coli* lacZ fusion gene," *Gene* (1988) 62:127–134.

Michels, P.A.M. et al., "Two tandemly linked identical genes code for the glycosomal glyceraldehyde–phosphate dehydrogenase in *Trypanosoma brucei*," *EMBO J* (1986) 5(5):1049–1056.

Misawa, N. et al., "Elucidation of the *Erwinia uredovora* Carotenoid Biosynthetic Pathway by Functional Analysis of Gene Products Expressed in *Escherichia coli*," *J Bacteriol* (Dec. 1990) 172(12):6704–6712.

(List continued on next page.)

Primary Examiner—James Ketter
(74) Attorney, Agent, or Firm—Morrison & Foerster LLP

(57) ABSTRACT

The present invention provides recombinant DNA comprising a transcription promoter and a downstream sequence to be expressed, in operable linkage therewith, wherein the transcription promoter comprises a region found upstream of the open reading frame of a highly expressed Phaffia gene, preferably a glycolytic pathway gene, more preferably the gene coding for Glyceraldehyde-3-Phosphate Dehydrogenase. Further preferred recombinant DNAs according to the invention contain promoters of ribosomal protein encoding genes, more preferably wherein the transcription promoter comprises a region found upstream of the open reading frame encoding a protein as represented by one of the disclosed amino acid sequences. According to a further aspect of the invention an isolated DNA sequence coding for an enzyme involved in the carotenoid biosynthetic pathway of *Phaffia rhodozyma* is provided.

45 Claims, 9 Drawing Sheets

OTHER PUBLICATIONS

Oslinga, K.A. et al., "Topogenesis of microbody enzymes: a sequence comparison of the genes for the glycosomal (microbody) and cytosolic phosphoglycerate kinases *Trypanosoma brucei*," *EMBO J* (1985) 4(13B):3811–3817.

Price, V.L. et al., "[25] Expression of Heterlogous Proteins in *Saccharomyces cerevisiae* Using the ADH2 Promoter," *Methods in Enzymology* (1990) in *Gene Expression Technology*, Goeddel, D.V. (ed.) 185:308–318, Academic Press, Inc. (1990).

Rosenberg S. et al., "[28] Glyceraldehyde–3–phosphate Dehydrogenase–Derived Expression Cassettes for Constitutive Synthesis of Heterologous Proteins," *Methods in Enzymology* (1990) in *Gene Expression Technology*, Goeddel, D.V. (ed.) 185:341–351, Academic Press, Inc. (1990).

Sambrook, J. et al., *Molecular Cloning: a Laboratory Manual*, 2nd Ed. Cold Spring Harbor Laboratory Press, 1989.

Scorer, C.A. et al. "Rapid Selection Using G418 of High Copy Number Transformants of *Pichia pastorsis* for High–level Foreign Gene Expression," *Bio/Technology* (Feb. 12, 1994) 12:181–184.

Swinkels, B.W. et al., "Characterization of the gene for the microbody (glycosomal) triosephosphate isomerase of *Trypanosoma brucei*," *EMBO J* (1986) 5(6):1291–1298.

Tuite, M.F. et al. "Regulated high efficiency expression of human interferon–alpha in *Saccharomyces cerevisiae*," *EMBO J* (1982) 1(5):306–308.

Woolford, J.L., Jr., "Nuclear Pre–mRNA Splicing in Yeast," *Yeast* (1989) 5:439–457.

* cited by examiner

A  pPRcrtE

B  pPRcrtBY

C  pPRcrtI pPRcrtY

|―――――|
 1.0kb

METHODS FOR TRANSFORMING PHAFFIA STRAINS, TRANSFORMED PHAFFIA STRAINS SO OBTAINED AND RECOMBINANT DNA IN SAID METHODS

TECHNICAL FIELD

The present invention relates to methods for transforming Phaffia yeast, transformed Phaffia strains, as well as recombinant DNA for use therein.

BACKGROUND OF THE INVENTION

Methods for transforming the yeast *Phaffia rhodozyma* have been disclosed in European patent application 0 590 707 A1. These methods involve incubation of protoplasts with DNA or incubation of Phaffia cells with DNA followed by lithium acetate treatment. The recombinant DNA used to transform Phaffia strains with either of these methods comprised a Phaffia actin gene promoter to drive expression of the selectable marker genes coding for resistance against G418 or phleomycin. The methods involve long PEG and lithium acetate incubation times and transformation frequencies are low. When protoplasts are used, the transformation frequency is dependent on the quality of the protoplast suspension, making the procedure less reliable.

Recently a method for transforming Phaffia strains has been reported by Adrio J. L. and Veiga M. (July 1995, Biotechnology Techniques Vol. 9, No. 7, pp. 509–512). With this method the w transformation frequencies are in the range of 3 to 13 transformants per µg DNA, which is low. A further disadvantage of the method disclosed by these authors consists in increased doubling time of the transformed cells. The authors hypothesised that this may be due to interference of the autonomously replicating vector with chromosome replication.

Clearly, there is still a need for a reliable and efficient method of transforming Phaffia strains with foreign DNA. It is an objective of the present invention to provide methods and means to achieve this. It is a further objective of the invention to optimize expression of certain genes in *Phaffia rhodozyma* in order to make Phaffia a more suitable production host for certain valuable compounds.

SUMMARY OF THE INVENTION

The invention provides a method for obtaining a transformed Phaffia strain, comprising the steps of contacting cells or protoplasts of a Phaffia strain with recombinant DNA under conditions conducive to uptake thereof, said recombinant DNA comprising a transcription promoter and a downstream sequence to be expressed which is heterologous to said transcription promoter, in operable linkage therewith, identifying *Phaffia rhodozyma* cells or protoplasts having obtained the said recombinant DNA in expressible form, wherein the transcription promoter comprises a region that is found upstream of the open reading frame of a highly expressed Phaffia gene. According to a preferred embodiment of the invention said highly expressed Phaffia gene is a glycolytic pathway gene, more preferably the glycolytic pathway gene is coding for Glyceraldehyde-3-Phosphate Dehydrogenase (GAPDH). According to one aspect of the invention, said heterologous downstream sequence comprises an open reading frame coding for resistance against a selective agent, such as G418 or phleomycin.

Another preferred method according to the invention is one, wherein said recombinant DNA comprises further a transcription terminator downstream from the said DNA to be expressed, in operable linkage therewith, which transcription terminator comprises a region found downstream of the open reading frame of a Phaffia gene. It is still further preferred, that the recombinant DNA is in the form of linear DNA.

Another preferred embodiment comprises, in addition to the steps above, the step of providing an electropulse after contacting of Phaffia cells or protoplasts with DNA.

According to another embodiment the invention provides a transformed Phaffia strain capable of high-level expression of a heterologous DNA sequence, which strain is obtainable by a method according to the invention. Preferably, said Phaffia strain contains at least 10 copies of the said recombinant DNA integrated into its genome, such as a chromosome, particularly in the ribosomal DNA locus of said chromosome.

The invention also provides recombinant DNA comprising a transcription promoter and a heterologous downstream sequence to be expressed, in operable linkage therewith, wherein the transcription promoter comprises a region found upstream of the open reading frame of a highly expressed Phyla gene, preferably a glycolytic pathway gene, more preferably a gene coding for Glyceraldehyde-3-Phosphate Dehydrogenase.

Also provided is recombinant DNA according to the invention, wherein the heterologous downstream sequence comprises an open reading frame coding for reduced sensitivity against a selective agent, preferably G418 or phleomycin. Said recombinant DNA preferably comprises further a transcription terminator downstream from the said heterologous DNA sequence to be expressed, in operable linkage therewith.

Further aspects of the invention concern a microorganism harbouring recombinant DNA according to the invention, preferably Phaffia strains, more preferably *Phaffia rhodozyma* strains, as well as cultures thereof.

According to still other preferred embodiments isolated DNA fragments are provided comprising a Phaffia GAPDH-gene, or a fragment thereof, as well as the use of such a fragment for making a recombinant DNA construct. According to one embodiment of this aspect said fragment is a regulatory region located upstream or downstream of the open reading frame coding for GAPDH, and it is used in conjunction with a heterologous sequence to be expressed under the control thereof The invention according to yet another aspect, provides a method for producing a protein or a pigment by culturing a Phaffia strain under conditions conducive to the production of said protein or pigment, wherein the Phaffia strain is a transformed Phaffia strain according to the invention.

According to another aspect of the invention, a method for obtaining a transformed Phaffia strain, comprising the steps of contacting cells or protoplasts of a Phaffia strain with recombinant DNA under conditions conducive to uptake thereof, said recombinant DNA comprising a transcription promoter and a downstream sequence to be expressed in operable linkage therewith, identifying *Phaffia rhodozyma* cells or protoplasts having obtained the said recombinant DNA in expressible form, wherein the downstream am sequence to be expressed comprise s an isolate d DNA sequence coding for an enzyme involved in the carotenoid biosynthetic pathway of *Phaffia rhodozyma*. Preferably, said enzyme has an activity selected from geranylgeranyl pyrophosphate synthase (crtE), phytoene synthase (crtB), phytoene desaturase (crtI) and lycopene cyclase (crtY), more preferably an enzyme having an amino acid sequence selected from the one represented by SEQIDNO: 13, SEQIDNO: 15, SEQIDNO: 17 and SEQIDNO: 19. According to a further embodiment, the transcription promoter is heterologous to said isolated DNA sequence, such as a glycolytic pathway gene in Phaffia. Especially preferred according to this embodiment is the Glyceraldehyde-3-Phosphate Dehydrogenase (GAPDH) gene promoter.

Also provided is a transformed Phaffia strain obtainable by a method according to the invention and capable of expressing preferably over-expressing the DNA sequence encoding an enzyme, involved in the carotenoid biosynthesis pathway gene.

The invention is also embodied in recombinant DNA comprising an isolated DNA sequence according to the invention, preferably in the form of a vector.

Also claimed is the use of such a vector to transform a host, such as a Phaffia strain:

A host obtainable by transformation, optionally of an ancestor, using a method according to any one of claims 1 to 5, wherein said host is preferably capable of over-expressing DNA according to the invention.

According to a further embodiment a method is provided for expressing an enzyme involved in the carotenoid biosynthesis pathway, by culturing a host according to the invention under conditions conducive to the production of said enzyme. Also provided is a method for producing a carotenoid by cultivating a host according to the invention under conditions conducive to the production of carotenoid.

The following figures further illustrate the invention.

DETAILED DESCRIPTION OF THE INVENTION

Figure 1:
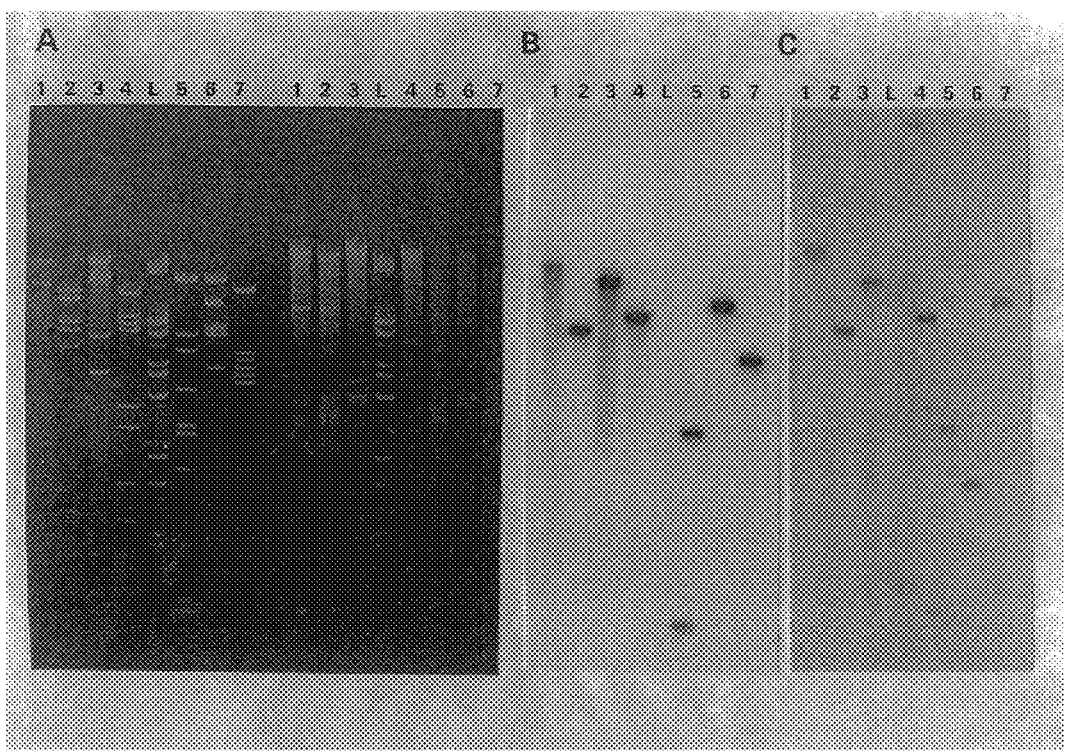
FIGS. 1A–1C Mapping of the restriction sites around the *Phaffia rhodozyma* GAPDH gene. Ethidium bromide stained 0.8% agarose gel (A) and Southern blot of chromosomal DNA (B) and cosmid pPRGDHcos1 (C) digested with several restriction enzymes and hybridized with the 300-bp PCR fragment of the, *Phaffia rhodozyma* GAPDH gene. Lane 1, DNA xKpnI; 2, xPstI; 3, xSmaI; 4, xSphI; L, lambda DNA digested with BstEII; 5, xSstI; 6, xXbaI and 7, xXhoI. The blot was hybridized in 6×SSC, 5×Denhardt's, 0.1% SDS, 100 ng/ml herring sperm DNA at 65° C. and washed with 0.1×SSC/0.1% SDS at 65° C. Exposure time of the autoradiogram was 16 h for the cosmid and 48 h from the blot containing the chromosomal DNA.

The invention provides in generalised terms a method for obtaining a transformed Phaffia strain, comprising the steps of contacting cells or protoplasts of a Phaffia strain with recombinant DNA under conditions conducive to uptake thereof, said recombinant DNA comprising a transcription promoter and a downstream sequence to be expressed which is heterologous to said transcription promoter, in operable linkage therewith, identifying *Phaffia rhodozyma* cells or protoplasts having obtained the said recombinant DNA in expressible form, wherein the transcription promoter comprises a region that is found upstream of the open reading frame of a highly expressed Phaffia gene.

In order to illustrate the various ways of practicing the invention, some embodiments will be high-lighted and the meaning or scope of certain phrases will be elucidated.

The meaning of the expression recombinant DNA is well known in the art of genetic modification, meaning that a DNA molecule is provided, single or double stranded, either linear or circular, nicked or otherwise, characterised by the joining of at least two fragments of different origin. Such joining is usually, but not necessarily done in vitro. Thus, within the ambit of the claim are molecules which comprise DNA from different organisms or different genes of the same organism, or even different regions of the same gene, provided the regions are not adjacent in nature. The recombinant DNA according to the invention is characterised by a transcription promoter found upstream of an open reading frame of a highly expressed Phaffia gene, fused to a heterologous DNA sequence. With heterologous is meant 'not naturally adjacent'. Thus the heterologous DNA sequence may be from a different organisms, a different gene from the same organism, or even of the same gene as the promoter, provided that the downstream sequence has been modified, usually in vitro. Such modification may be an insertion, deletion or substitution, affecting the encoded protein and/or its entrance into the secretory pathway, and/or its post-translational processing, and/or its codon usage.

The strong transcription promoter according to the invention must be in operable linkage with the heterologous downstream sequence in order to allow the transcriptional and translational machinery to recognise the starting signals. The regions upstream of open reading frames of highly expressed Phaffia genes contain TATA-like structures which are positioned at 26 to about 40 nucleotides upstream of the cap-site; the latter roughly corresponds with the transcriptional start site. Thus in order to allow transcription of the heterologous downstream sequence to start at the right location similar distances are to be respected. It is common knowledge, however, that there is a certain tolerance in the location of the TATA-signal relative to the transcription start site. Typically, mRNAs of the eukaryotic type contain a 5'-untranslated leader sequence (5'-utl), which is the region spanning the transcription start site to the start of translation; this region may vary from 30 to more than 200 nucleotides. Neither the length nor the origin of the 5'-utl is very critical; preferably it will be between 30 and 200 nucleotides. It may be from the same gene as the promoter, or it may be from the gene coding for the heterologous protein. It is well known that eukaryotic genes contain signals for the termination of transcription and/or polyadenylation, downstream of the open reading frame. The location of the termination signal is variable, but will typically be between 10 and 200 nucleotides downstream from the translational stop site (the end of the open reading frame), more usually between 30 and 100 nucleotides downstream from the translational stop site. Although the choice of the transcription terminator is not critical, it is found, that the when the terminator is selected from a region downstream of a Phaffia gene, preferably of a highly expressed Phaffia gene, more preferably from the GAPDH-encoding gene, the level of expression, as well as the frequency of transformation is improved.

It was found that significant numbers of clones were obtained which could grow on very high G418 concentrations (up to, and over, 1 mg/ml). Transcription promoters according to the invention are said to be from highly expressed genes, when they can serve to allow growth of transformed Phaffia cells, when linked to a G418 resistance gene as disclosed in the Examples, in the presence of at least 200 µm/ml, preferably more than 400, even more preferably more than 600, still more preferably more than 800 µg/ml of G418 in the growth medium. Examples of such promoters are, in addition to the promoter upstream from the GAPDH-gene in Phaffia, the promoters from Phaffia genes which are homologous to highly expressed genes from other yeasts, such as Pichia, Saccharomyces, Kluyveromyces, or fungi, such as Trichoderma, Aspergillus, and the like. Promoters which fulfill the requirements according to the invention, may be isolated from genomic DNA using molecular biological techniques which are, as such, all available to the person skilled in the art. The present invention provides a novel strategy for isolating strong promoters from Phaffia as follows. A cDNA-library is made from Phaffia mRNA, using known methods. Then for a number of clones with a cDNA insert, the DNA fragment (which represents the cDNA complement of the expressed mRNA) is sequenced. As a rule all fragments represent expressed genes from Phaffia. Moreover, genes that are abundantly expressed (such as the glycolytic promoters) are overrepresented in the mRNA population. Thus, the number of DNA-fragments to be sequenced in order to find a highly expressed gene, is limited to less than 100, probably even less than 50. The sequencing as such is routine, and should not take more than a couple of weeks. The nucleotide sequences obtained from this limited number of fragments, is subsequently compared to the known sequences stored in electronic databases such as EMBL or Geneseq. If a fragment shows homology of more than 50% over a given length (preferably more than 100 basepairs) the fragment is likely to represent the Phaffia equivalent of the gene found in the electronic database. In yeasts other than Phaffia, a number of highly expressed genes have been identified. These genes include the glycolytic pathway genes, phosphoglucoisomerase, phosphofructokinase, phosphotrioseisomerase, phosphoglucomutase, enolase, pyruvate kinase, alcohol dehydrogenase genes (EP 120 551, EP 0 164 556; Rosenberg S. et al., 1990, Meth. Enzymol.: 185, 341–351; Tuite M. F. 1982, EMBO J. 1, 603–608; Price V. et al., 1990, Meth. Enzymol. 185, 308–318) and the galactose regulon (Johnston, S. A. et al., 1987, Cell 50, 143–146). Accordingly, those Phaffia cDNA fragments that are significantly homologous to the highly expressed yeast genes (more than 40%, preferably more than 50% identity in a best match comparison over a range of more than 50, preferably more than 100 nucleotides) should be used to screen a genomic library from Phaffia, to find the corresponding gene. Employing this method, 14 higly expressed mRNAs from *Phaffia rhodozyma* have been copied into DNA, sequenced, and their (putative), open reading frames compared to a nucleic acid and amino amino acid sequence databases. It turned out that 13 out of these fourteen cDNAs coded for ribosomal protein genes, of which one coded simultaneously to ubiquitin; one cDNA codes for a glucose-repressed gene. The isolation of the genes and the promoters usually found upstream of the coding regions of these genes is now underway, and it is anticipated that each of these transcription promoters may advantageously be used to express heterologous genes, such as carotenoid biosynthesis genes. Among the genes and transcription promoters especially preferred according to this invention are the promoter found upstream of the ubiquitin-ribosomal 40S protein corresponding to the cDNA represented in SEQIDNO:10, the glucose-repressed cDNA represented in SEQIDNO:26, the 40S ribosomal protein S27 encoding cDNA represented in SEQIDNO:28, the 60S ribosomal protein Pla encoding cDNA represented by SEQIDNO:30, the 60S ribosomal protein L37e encoding cDNA represented in SEQIDNO:32, the 60S ribosomal protein L27a encoding cDNA represented in SEQIDNO:34, the 60S ribosomal protein L25 encoding cDNA represented in SEQIDNO:36, the 60S ribosomal protein P2 encoding cDNA represented in SEQIDNO:38, the 40S ribosomal protein S17A/B encoding cDNA represented in SEQIDNO:40, the 40S ribosomal protein S31 encoding cDNA represented in SEQIDNO:42, the 40S ribosomal protein S10 encoding cDNA represented in SEQIDNO:44, the 60S ribosomal protein L37A encoding cDNA represented in SEQIDNO:46, the 60S ribosomal protein L34 encoding cDNA represented in SEQIDNO:48, or the 40S ribosomal protein S16 encoding cDNA represented in SEQIDNO:50.

Promoters from these or other highly expressed genes can be picked up by the method according to the invention using only routine skills of (a) making a cDNA library on mRNA isolated from a Phaffia strain grown under desired conditions, (b) determining (part of) the nucleotide sequence of the (partial) cDNAs obtained in step (a), (c) comparing the obtained sequence data in step (b) to known sequence data, such as that stored in electronic databases, (d) cloning putative promoter fragments of the gene located either directly upstream of the open reading frame or directly upstream of the transcription start site of the gene corresponding to the expressed cDNA, and (e) verifying whether promoter sequences have been obtained by expressing a suitable marker, such as the G418 resistance gene, or a suitable non-selectable "reporter" sequence downstream from a fragment obtained in (d), transforming the DNA into a *Phaffia rhodozyma* strain and determining the level of expression of the marker gene or reporter sequence of transformants. A transcriptional promoter is said to be of a highly expressed gene if it is capable of making *Phaffia rhodozyma* cells transformed with a DNA construct comprising the said promoter linked uptream of the G418 resistance marker resistant to G418 in concentrations exceeding 200 µg per liter culture medium, preferably at least 400, more prefereably more than 600 µg/l. Especially preferred promoters are those conferring resistance against more than 800 µg/ml G418 in the growth medium.

Optionally, the transcriptional start site may be determined of the gene corresponding to the cDNA corresponding to a highly expressed gene, prior to cloning the putative promoter sequences; this may serve to locate the transcriptional initiation site more precisely, and moreover, helps to determine the length of the 5'-non-translated leader of the gene. To determine the location of the transcription start site, reverse primer extension, or classical S1-mapping may be performed, based on the knowledge of the cDNA sequence. Thus the exact location of the transcription promoter can be determined without undue burden, and the isolation of a fragment upstream of the transcription start site and containing the promoter, from a hybridising genomic clone (for example a phage or cosmid) is routine. Cloning the putative promoter fragment in front (upstream) of the coding region of, for example the G418-resistance gene, and transforming the gene cassette to Phaffia in order to evaluate the level of G418 resistance, and hence the level of expression of the G418-resistance gene as a consequence of the presence of the promoter is routine.

In a manner essentially as described for the isolation of other strong promoters, above, a transcription terminator may be isolated, with the proviso, that the terminator is located downstream from the open reading frame. The transcription stop site can be determined using procedures which are essentially the same as for the determination of the transcription start site. All these procedures are well known to those of skill in the art. A useful handbook is Nucleic Acid Hybridisation, Edited by B. D. Hames & S. J. Higgins, IRL Press Ltd., 1985; or Sambrook, sub. However, it is not critical that the transcription terminator is isolated from a highly expressed Phaffia gene, as long as it is from an expressed gene.

Using recombinant DNA according to the invention wherein the open reading frame codes for reduced sensitivity against G418, a transformation frequency was obtained up to 160 transformants per µg of linear DNA, at a G418 concentration in the medium of 40 µg/ml.

About 10 to 20 times as much transformed colonies were obtained with the vector according to the invention (pPR2) than with the prior art vector pGB-Ph9, disclosed in EP 0 590 707 A1 ( see Table 2; in the experiment of Example 7, the improvement is even more striking).

The method according to the invention calls for conditions conducive to uptake of the recombinant DNA. Such conditions have been disclosed in EP 509 707. They include but are not limited to the preparation of protoplasts using standard procedures known to those of skill in the art, and subsequent incubation with the recombinant DNA. Alternatively, Phaffia cells may be incubated overnight in the presence of LiAc and recombinant DNA. Still further alternative methods involve the use of particle acceleration. According to a preferred embodiment, the conditions conducive to uptake involve electroporation of recombinant DNA into Phaffia cells, such as described by Faber et al., (1994, Current Genetics 25, 305–310). Especially preferred conditions comprise electroporation, wherein the recombinant DNA comprises Phaffia ribosomal DNA, said recombinant DNA being in the linear form, most preferably by cleaving said recombinant DNA in the said ribosomal region. Still further preferred conditions, comprise the use of recombinant DNA in amounts of between 1 and 10 µg per $10^8$ cells, more preferably about 5 µg recombinant DNA is used per $2\times10^8$ cells, which are cultivated for 16 h at 21° C.

Once cells have been transformed according to the method, identification of transformed cells may take place using any suitable technique. Thus, identification may be done by hybridisation techniques, DNA amplification techniques such a polymerase chain reaction using primers based on the recombinant DNA used, and the like. A preferred method of identifying transformed cells is one which employs selection for the recombinant DNA that comprises a gene coding for reduced sensitivity against a selective agent. A useful selective agent is G418, hygromycin, phleomycin and amdS. Genes that code for reduced sensitivity against these selective agents are well known in the art. The open reading frames of these genes may be used as the heterologous downstream sequence according to the invention, allowing selective enrichment of transformed cells, prior to identification of transformed cells. Once transformed cells have been identified they may used for further manipulation, or used directly in the production of valuable compounds, preferably in large scale fermentors.

It will be clear, that a very efficient method for transforming Phaffia strains has been disclosed. Moreover, not only the frequency of transformation is high, the expression levels of the transforming DNA is very high as well, as is illustrated by the exceptionally high resistance against G418 of the transformed Phaffia cells when the open reading frame of the G418-resistance gene was fused to a promoter according to the invention when compared to the G418 resistance gene under control of the actin promoter in pGB-Ph9. It is concluded, therefore, that the GAPDH-promoter is a high-level transcriptional promoter that can be suitably used in conjunction with any heterologous DNA sequence, in order to reach high expression levels thereof in Phaffia strains.

It will be clear that the availability of new expression tools, in the form of the recombinant DNA according to the invention, creates a wealth of possibilities for producing new and valuable biomolecules in Phaffia.

Preferably, the downstream sequence comprises an open reading frame coding for proteins of interest. For example genes already present in Phaffia, such as those involved in the carotenoid pathway, may be manipulated by cloning them under control of the high-level promoters according to the invention. Increased expression may change the accumulation of intermediates and/or end-products or change the pathway of β-carotene, cantaxanthin, astaxanthin and the like. The overexpression of the crtB gene from *Erwinia uredovora* will likely increase astaxanthin levels, as the product of this gene is involved in the rate limiting step. The expression of a protein of interest may also give rise to xanthophylls not known to be naturally produced in Phaffia, such as zeaxanthin. An open reading frame that may be suitably employed in such a method includes but is not limited to the one encoding the protein producing zeaxanthin (crtZ gene) obtained from *Erwinia uredovora* (Misawa et al.1990. J.Bacteriol. 172: 6704–6712). Other carotenoid synthesis genes can be obtained for example from Flavobacterium (a gram-positive bacterium), Synechococcus (a cyanobacterium) or Chlamydomonas or Dunaliella (algae).

Obviously, carotenoid synthesis genes of a Phaffia strain, once the genes have been isolated and cloned, are suitably cloned into a recombinant DNA according to the invention and used to modify the carotenoid content of Phaffia strains. Examples of cloned carotenoid genes that can suitably be overexpressed in Phaffia, are those mentioned in FIG. 8. Particularly useful is crtE from *Phycomyces blakesleanus*, encoding Geranylgeranyl Diphosphate Synthase, and crtB, encoding phytoene synthase, as this step appears to be the rate-limiting step in carotenoid synthesis in *Thermus thermophylus* (Hoshino T. et al., 1994, Journal of Fermentation and Bioengineering 77. No. 4, 423–424). Especially preferred sources to isolate carotenoid biosynthetic genes or cDNAs from are the fungi *Neurospora crassa, Blakeslea trispora*. Other yeasts shown to possess cross-hybrising species of carotenoid biosynthetic genes are *Cystofylobasidium*, e.g. *bisporidii* and *capitatum*.

Carotenoid biosynthesis genes have also been identified in plants; these plant cDNAs or genes from plants may be used as well. Optionally, the codon usage of the Phaffia genes or cDNAs may be adapted to the preferred use in the host organism.

Of special interest according to the present invention, are the DNA sequences coding for four different enzymes in the carotenoid biosynthesis pathway of *Phaffia rhodozyma*, represented in the sequence listing. It will be clear to those having ordinary skill in the art, that once these DNA sequences have been made available it will be possible to bring about slight modifications to the DNA sequence without modifying the amino acid sequence. Such modifications are possible due to the degeneracy of the genetic code. Such modifications are encompassed in the present invention. However, also modifications in the coding sequences are envisaged that create modifications in the amino acid sequence of the enzyme. It is well known to those of skill in the art that minor modifications are perfectly permissible in terms of enzymatic activity. Most changes, such as deletions, additions or amino acid substitutions do not affect enzymatic activity, at least not dramatically. Such variants as comprise one or more amino acid deletions, additions or substitutions can readily be tested using the complementation test disclosed in the specification. The skilled person is also familiar with the term "conservative amino acid substitutions", meaning substitutions of amino acids by similar amino acids residing in the same group. The skilled person is also familiar with the term "allelic variant", meaning naturally occurring variants of one particular enzyme. These conservative substitutions and allelic enzyme variants do not depart from the invention.

As stated, at the DNA level considerable variation is acceptable. Although the invention discloses four DNA sequences, as represented in SEQIDNO: 12, SEQIDNO: 14, SEQIDNO: 16, SEQIDNO: 18, SEQIDNO:20, or SEQIDNO: 22, in detail also isocoding variants of the DNA sequence represented in SEQIDNO: 12, SEQIDNO: 14, SEQIDNO: 16, SEQIDNO: 18, SEQIDNO: 20, or SEQIDNO: 22, are encompassed by the present invention. Those of skill in the art would have no difficulty in adapting the nucleic acid sequence in order to optimize codon usage in a host other than *P. rhodozyma*. Those of skill in the art would know how to isolate allelic variants of a DNA sequence as represented in SEQIDNO: 12, SEQIDNO: 14, SEQIDNO: 16, SEQIDNO, 11, SEQIDNO: 20, or SEQIDNO: 22 from related Phaffia strains. Such allelic variants clearly do not deviate from the present invention.

Furthermore, using the DNA sequences disclosed in the sequence listing, notably SEQIDNO: 12, SEQIDNO: 14, SEQIDNO: 16 or SEQIDNO: 18, as a probe, it will be possible to isolate corresponding genes form other strains, or other microbial species, or even more remote eukaryotic species if desired, provided that there is enough sequence homology, to detect the same using hybridisation or amplification techniques known in the art.

Typically, procedures to obtain similar DNA fragments involve the screening of bacteria or bacteriophage plaques transformed with recombinant plasmids containing DNA fragments from an organism known or expected to produce enzymes according to the invention. After in situ replication of the DNA, the DNA is released from the cells or plaques, and immobilised onto filters (generally nitro-cellulose). The filters may then be screened for complementary DNA fragments using a labeled nucleic acid probe based on any of the sequences represented in the sequence listing. Dependent on whether or not the organism to be screened for is distantly or closely related, the hybridisation and washing conditions should be adapted in order to pick up true positives and reduce the amount of false positives. A typical procedure for the hybridisation of filter-immobilised DNA is described in Chapter 5, Table 3, pp. 120 and 121 in: *Nucleic acid hybridisation—a practical approach*, B. D. Hames & S. J. Higgins Eds., 1985, IRL Press, Oxford). Although the optimal conditions are usually determined empirically, a few useful rules of thumb can be given for closely and less closely related sequences.

In order to identify DNA fragments very closely related to the probe, the hybridisation is performed as described in Table 3 of Hames & Higgins, supra, (the essentials of which are reproduced below) with a final washing step at high stringency in 0.1*SET buffer (20 times SET 3M NaCl, 20 mM EDTA, 0.4 M Tris-HCl, pH 7.8), 0.1% SDS at 68° Celsius).

To identify sequences with limited homology to the probe the procedure to be followed is as in Table 3 of Hames & Higgins, supra, but with reduced temperature of hybridisation and washing. A final wash at 2*SET buffer, 50° C. for example should allow the identification of sequences having about 75% homology. As is well known to the person having ordinary skill in the art, the exact relationship between homology and hybridisation conditions depend on the length of the probe, the base composition (% of G+C) and the distribution of the mismatches; a random distribution has a stronger decreasing effect on $T_m$ then a non-random or clustered pattern of mismatches.

The essentials of the procedure described in Table 3, Chapter 3 of Hames & Higgins are as follows:
(1) prehybridisation of the filters in the absence of probe, (2) hybridisation at a temperature between 50 and 68° C. in between 0.1 and 4*SET buffer (depending on the stringency), 10*Denhardt's solution (100*Denhardt's solution contains 2% bovine serum albumin, 2% Ficoll, 2% polyvinylpyrrolidone), 0.1% SDS, 0.1% sodiumpyrophosphate, 50 µg/ml salmon sperm DNA (from a stock obtainable by dissolving 1 mg/ml of salmon sperm DNA, sonicated to a length of 200 to 500 bp, allowed to stand in a water bath for 20 min., and diluted with water to a final concentration of 1 mg/ml); hybridisation time is not too critical and may be anywhere between 1 and 24 hours, preferably about 16 hours (o/n); the probe is typically labeled by nick-translation using $^{32}P$ as radioactive label to a specific activity of between $5*10^7$ and $5*10^8$ c.p.m./µg; (3) (repeated) washing of the filter with 3*SET, 0.1% SDS, 0.1% sodiumpyrophosphate at 68° C. at a temperature between 50C and 68° C. (dependent on the stringency desired), repeated washing while lowering the SET concentration to 0.1%., wash once for 20 min. in 4*SET at room temperature, drying filters on 3MM paper, exposure of filters to X-ray film in a cassette at −70° C. for between 1 hour and 96 hours, and developing the film.

Generally, volumina of prehybridisation and hybridisation mixes should be kept at a minimum. All "wet" steps may be carried out in little sealed bags in a pre-heated water bath.

The above procedure serves to define the DNA fragments said to hybridise according to the invention. Obviously, numerous modifications may be made to the procedure to identify and isolate DNA fragments according to the invention. It is to be understood, that the DNA fragments so obtained fall under the terms of the claims whenever they can be detected following the above procedure, irrespective of whether they have actually been identified and/or isolated using this procedure.

Numerous protocols, which can suitably be used to identify and isolate DNA fragments according to the invention, have been described in the literature and in handbooks, including the quoted Hames & Higgins, supra).

With the advent of new DNA amplification techniques, such as direct or inverted PCR, it is also possible to clone DNA fragments in vitro once sequences of the coding region are known.

Also encompassed by the claims is a DNA sequence capable, when bound to nitrocellulose filter and after incubation under hybridising conditions and subsequent washing, of specifically hybridising to a radio-labelled DNA fragment having the sequence represented in SEQIDNO: 12, SEQIDNO: 14, SEQIDNO: 16 or SEQIDNO: 18, as detectable by autoradiography of the filter after incubation and washing, wherein said incubation under hybridising conditions and subsequent washing is performed by incubating the filter-bound DNA at a temperature of at least 50° C., preferably at least 55° C., more preferably at least 60° C. in the presence of a solution of the said radio-labeled DNA in 0.3 M NaCl, 40 mM Tris-HCl, 2 mM EDTA, 0.1% SDS, pH 7.8 for at least one hour, whereafter the filter is washed at least twice for about 20 minutes in 0.3 M NaCl, 40 mM Tris-HCl, 2 mM EDTA, 0.1% SDS, pH 7.8, at a temperature of 50° C., preferably at least 55° C., more preferably at least 60° C., prior to autoradiography.

The heterologous DNA sequence according to the invention may comprise any open reading lo frame coding for valuable proteins or their precursors, like pharmaceutical proteins such as human serum albumin, IL-3, insulin, factor VIII, tPA, EPO, α-interferon, and the like, detergent enzymes, such as proteases and lipases and the like, cell wall degrading enzymes, such as xylanases, pectinases, cellulases, glucanases, polygalacturonases, and the like, and other enzymes which may be useful as additives for food or feed (e.g. chymosin, phytases, phospholipases, and the like). Such genes may be expressed for the purpose of recovering the protein in question prior to subsequent use, but sometimes this may not be necessary as the protein may be added to a product or process in an unpurified form, for example as a culture filtrate or encapsulated inside the Phaffia cells.

The yeast cells containing the carotenoids can be used as such or in dried form as additives to animal feed. Furthermore, the yeasts can be mixed with other compounds such as proteins, carbohydrates or oils.

Valuable substances, such as proteins or pigments produced by virtue of the recombinant DNA of the invention may be extracted. Carotenoids can also be isolated for example as described by Johnson et al. (Appl. Environm. Microbiol. 35: 1155–1159 (1978)).

Purified carotenoids can be used as colorants in food and/or feed. It is also possible to apply the carotenoids in cosmetics or in pharmaceutical compositions.

The heterologous downstream sequence may also comprise an open reading frame coding for reduced sensitivity against a selective agent. The open reading frame coding for an enzyme giving G418 resistance was used satisfactorily in the method according to the invention, but the invention is not limited to this selection marker. Other useful selection markers, such as the phleomycin resistance gone may be used, as disclosed in EP 590 707. Each of these genes is advantageously expressed under the control of a strong promoter according to the invention, such as the GAPDH-promoter.

The invention is now being illustrated in greater detail by the following non-limitative examples.

EXPERIMENTAL

Strains:
  E. coli DH5α: supE44lacU169 (80lacZM15) hsdR17 recA1 endA1 gyrA96 thi-1 relA1
  E. coli LE392: supE44 supF58 hsdR514 galK2 galT22 metB1 trpR55 lacY1
  P. rhodozyma CBS6938
Plasmids:
  pUC19 (Gibco BRL)
  pTZ19R
  PUC-G418
  pGB-Ph9 (Gist-brocades)
  pMT6 (1987, Breter H.-J., Gene 53, 181–190))
Media:
  LB: 10 g/l bacto tryptone, 5 g/l yeast extract, 10 g/l NaCl. Plates; +20 g/l bacto agar. When appropriate 50 μg/ml ampicillin.
  YePD: 10 g/l yeast extract, 20 g/l bacto peptone, 20 g/l glucose. Plates; +20 g/l bacto agar. When appropriate 50 g/ml Geneticin (G418).
Methods
  All molecular cloning techniques were essentially carried out as described by Sambrook et al. in Molecular Cloning: a Laboratory Manual, 2nd Edition (1989; Cold Spring Harbor Laboratory Press).

Enzyme incubations were performed following instructions described by the manufacturer. These incubations include restriction enzyme digestion, dephosphorylation and ligation (Gibco BRL).

Isolation of chromosomal DNA from *Phaffia rhodozyma* as described in example 3 of patent Gist-brocades; EP 0 590 707 A1. Chromosomal DNA from *K. lactis* and *S.cerevisiae* was isolated as described by Cryer et al.(Methods in Cell Biology 12: 39, Prescott D. M. (ed.) Academic Press, New York).

Isolation of large (>0.5-kb) DNA fragments from agarose was performed using the Geneclean II Kit whereas small (<0.5-kb) and DNA fragments or fragments from PCR mixtures were isolated using Wizard™ DNA, Clean-Up System (Promega).

Transformation of *E. coli* was performed according to the CaCl$_2$ method described by Sambrook et al. Packaging of cosmid ligations and transfection to *E. coli* LE392 was carried out using the Packagene Lambda DNA Packaging System (Promega), following the Promega protocols.

Isolation of plasmid DNA from *E. coli* was performed using the QIAGEN (Westburg B. V. NL).

Transformation of Phaffia CBS6938 was done according to the method for *H. polymorpha* described by Faber et al., supra;

Inoculate 30 ml of YePD with 1 CBS6938 colony
Grow 1–2 days at 21° C., 300 rpm (pre-culture)
Inoculate 200 ml of YePD with pre-culture to $OD_{600}=$ between 0 and 1 (if above 1 dilute with water)
Grown o/n at 21° C., 300 rpm until $OD_{600}=1.2$ (dilute before measuring)
Centrifuge at 5 min. 8000 rpm, room temperature. Remove supernatant thoroughly
Resuspend pellet in 25 ml 50 mM KPi pH 7.0, 25 mM DTT (freshly made) Transfer suspension to a fresh sterile 30 ml centrifuge tube and incubate for 15 min. at room temperature
Centrifuge 5 min. at 8000 rpm 4° C., remove supernatant thoroughly
Resuspend pellet in 25 ml of ice cold STM (270 mM sucrose, 10 mM Tris pH 7.5, 1 mM $MgCl_2$)
Centrifuge 5 min. at 8000 rpm, 4° C.
Repeat washing step
Resuspend cells in 0.5 ml of ice cold STM ($3*10^9$ cells/ml). Keep on ice!
Transfer 60 μl of cell suspension to pre-cooled Eppendorf tubes containing 5 μg transforming DNA (use precooled tips!), Keep on ice
Transfer Cell/DNA mix to precooled electroporation cuvettes (top to bottom)
Pulse: 1.5 kV, 400Ω, 25 μF
Immediately add 0.5 ml of ice cold YePD. Transfer back to ep using a sterile Pasteur pipette
Incubate 2.5 hrs at 21° C.
Plate 100 μl onto YePD-plates containing 40 μg/ml G418
Incubate at 21° C. until colonies appear.

Pulsed Field Electrophoresis was performed using a GENE Navigator+accessories (Pharmacia). Conditions: 0.15*TBE, 450 V, pulse time 0.5 s, 1.2% agarose, run time 2 h.

Polymerase Chain Reaction (PCR) experiments were performed in mixtures having the following composition:
   5 ng of plasmid DNA or 1 μg chromosomal DNA
   0.5 μg of oligo nucleotides (5 μg degenerated oligo's in combination with chromosomal DNA)
   10 nm of each dNTP
   2.5 m KCl
   0.5 μm Tris pH 8.0
   0.1 μm MgCl2
   0.5 μg gelatin
   1.3 U Taq polymerase (5 U in combination with chromosomal DNA)
   $H_2O$ was added to a total volume of 50 μl Reactions were carried out in an automated thermal cycler (Perkin-Elmer). Conditions: 5 min. 95° C., followed by 25 repeated cycli; 2' 94° C., 2' 45° C. 3' 72° C. Ending; 10 min. 72° C.

Fusion PCR reactions were performed as described above, except that 2 DNA fragments with compatible ends were added as a template in equimolar amounts.

Oligo nucleotide sequences were as follows:
3005: CGGGATCCAA(A/G)CTNACNGGNATGGC (SEQIDNO: 1);
3006: CGGGATCC(A/G)TAICC(C/A/G)(C/T)A(T/C)TC(A/G)TT(A/G)TC(A/G)TACCA (SEQIDNO: 2);
4206: GCGTGACTTCTGGCCAGCCACGATAGC (SEQIDNO: 3);
5126: TTCAATCCACATGATGGTAAGAGTGTTAGAGA (SEQIDNO: 4);
5127: CTTACCATCATGTGGATTGAACAAGATGGAT (SEQIDNO: 5);
AAGCTCTCGAGGTACCTGGTGGGTGCATGTATGTAC (SEQIDNO: 6);
CCAAGGCCTAAAACGGATCCCTCCAAACCC (SEQIDNO: 7);
G C C AAGCTTCTCGAGCTTGATCAGATAAAGATAGAGAT (SEQIDNO: 8);

EXAMPLE 1

G-418 Resistance of Phaffia Transformant G418-1

To determine the expression of the G418 resistance gene in pGB-Ph9, transformant G418-1 (EP0 590 707 A1) was exposed to increasing concentrations of G418. Two dilutions of a G418-1 culture were plated onto YepD agar containing 0–1000 jig/ml G418 (Table 1).

TABLE 1

Survival of Phaffia transformant G418-1 on YepD agar medium containing increasing concentrations of G418.

| [G418] μg/ml | Phaffia G418-1 Dil. = $10^{-4}$ ($OD_{600}$ = 7) | Phaffia G418-1 Dil. = $10^{-5}$ ($OD_{600}$ = 7) | Phaffia (CBS6938) Dil. = 0 ($OD_{600}$ = 5) |
|---|---|---|---|
| 0 | >300 | 74 | >300 |
| 200 | >300 | 70 | 0 |
| 300 | >300 | 61 | 0 |
| 400 | 212 | 13 | 0 |
| 500 | 10 | 2 | 0 |
| 600 | 0 | 0 | 0 |
| 700 | 0 | 0 | 0 |
| 800 | 0 | 0 | 0 |
| 900 | 0 | 0 | 0 |
| 1000 | 0 | 0 | 0 |

At a concentration of 600 μg/ml G418 less than 1% of the plated cells survived. It can be concluded that despite multicopy integration of pGB-Ph9, G418-1 shows a rather weak resistance to G418 (Scorer et al, 1994, Bio/Technology 12, p. 181 et seq., Jimenez and Davies, 1980, Nature 187 p. 869 et seq.), most probably due to a weak action of the Phaffia actin promoter in the plasmid. The results that the Phaffia actin promoter works poorly, prompted us to isolate promoter sequences of Phaffia with strong promoter activity.

EXAMPLE 2

Synthesis of Specific Probes of Glycolytic Genes from *Phaffia rhodozyma* by PCR The polymerase chain reaction (PCR) technique was used in an attempt to synthesize a homologous probe of the genes encoding glyceraldehyde-3-phosphate dehydrogenase (GAPDH), phosphoglycerate kinase (PGK) and the triose phosphate isomerase (TPI) of *Phaffia rhodozyma*.

A set of degenerated oligonucleotides was designed based on the conserved regions in the GAPDH-gene (Michels et al., 1986. EMBO J. 5: 1049–1056), PGK-gene (Osinga et al., 1985. EMBO J. 4: 3811–3817) and the TPI-gene (Swinkels et al., 1986. EMBO J. 5: 1291–1298).

All possible oligo combinations were used to synthesize a PCR-fragment with chromosomal DNA of *Phaffia rhodozyma* (strain CBS6938) as template. Chromosomal DNA of *Saccharomyces cerevisiae* and *Kluyveromyces lactis* as template was used to monitor the specificity of the amplification. The PCR was perfomed as described above, the PCR conditions were 1' 95° C., 2' annealing temperature ($T_a$), in 5' from annealing temperature to 72° C., 2' 72° C., for 5 cycli followed by 1' 95° C., 2' 55° C. and 2' 72° C. for 25 cycli and another elongation step for 10' 72° C. Three different $T_a$ were used 40° C., 45° C. and 50° C.

Under these conditions, only one primer combination produced a fragment of the expected size on chromosomal DNA of Phaffia as template. Using the oligo combination no: 3005 and 3006 and a $T_a$ of 45° C. a 0.3-kb fragment was found. Specifically, the GAPDH oligonucleotides correspond with amino acids 241–246 and 331–338 of the published S. cerevisiae sequence. (It was concluded that to isolate the promoters corresponding to the PGK- and TPI-genes from Phaffia, further optimization of the PCR-conditions is required, or homologous primers should be used. Another alternative method for isolating high level promoters is disclosed in the detailed description, supra.

The amplified fragment was purified from the PCR reaction and was digested with BamHI and ligated into the dephosphorylated BamHI site of pTZ19R. The ligation mixture was transformed to competent E. coli DH5α cells prepared by the $CaCl_2$-method and the cell were plated on LB-plates with 50 μg/ml Amp and 0.1 mM IPTG/50 μg/ml X-gal. Plasmid DNA was isolated from the white colonies. The pTZ19R clone with the right insert, called pPRGDH1, was subsequently used for sequence analysis of the insert. The cloned sequence encoded for the carboxy terminal fragment of GAPDH of Phaffia as shown by comparison with the GAPDH-gene sequence of S. cerevisiae (Holland and Holland, 1979. J. of Biol. Chem. 254: 9839–9845).

EXAMPLE 3

Isolation of the GAPDH-gene of Phaffia

To obtain the complete GAPDH-gene including expression signals the 0.3-kb BamHI fragment of pPRGDH1 was used to screen a cosmid library of Phaffia.
Preparation of the Vector for Cosmid Cloning Vector preparation was simplified, because of the presence of a double cos-site in pMT6. pMT6 was digested to completion with blunt end cutter PvuII to release the cos-sites. Digestion efficiency was checked by transformation to E. coli DH5α and found to be >99%.

The PvuII digested pMT6 was purified by phenol:chloroform extraction and ethanol precipitation and finally solved in 30 μl TE at a concentration of 2 μg/μl. The vector was subsequently digested with cloning enzyme BamHI and the vector arms were purified as described above ("Experimental").
Preparation of Target DNA Isolation of genomic DNA of Phaffia strain CBS6938 was performed as described in the part named "Experimental". The cosmid pMT6 containing inserts of 25–38-kb are most efficiently packaged. Therefore genomic DNA was subjected to partial digestion with the restriction enzyme Sau3A. Target DNA was incubated with different amounts of enzyme. Immediately after digestion the reactions were stopped by the extraction of DNA from the restriction mixture with phenol-chloroform. The DNA was Is precipitated by using the ethanol method and the pelleted DNA after centrifugation was dissolved in a small volume of TE. Contour clamped homogeneous electric field (CHEF) electrophoresis was used to estimate the concentration and size of the fragments (Dawkins, 1989, J. of Chromatography 492, pp.
Construction of Genomic Cosmid Library Ligation of approximately 0.5 μg of vector arm DNA and 0.5 μg of target DNA was performed in a total volume of 10 μl in the presence of 5 mM ATP (to prevent blunt end ligation). Packaging in phage heads and transfection to E. coli LE 392 as described in Experimental. The primary library consisted of 7582 transfectants with an average insert of 28-kb as determined by restriction analysis. The library represents 3.5 times the genome with a probability of the presence of all genes in the library of 0.97 as calculated according to Sambrook (supra). For library amplification the transfectants were pooled by resuspending in 8 ml LB-broth. Additional 4.8 ml glycerol was added. The transfectants mixture was divided into 16 samples of 800 μl each and stored at −80° C. This amplified library consisted of $2.9*10^9$ transfectants.
Screening of the Cosmid Library A 100 μl sample was taken from this library and further diluted (106) in LB-broth and 200 μl was plated onto 10 LB-plates containing ampicillin. The plates were incubated overnight at 37° C. Each plate contained 300–400 colonies and filters were prepared. These filters were screened with the GAPDH-probe using hybridization and washing conditions as described above ("Experimental"). After 16 hours exposure, 3 strong hybridization signals were found on the autoradiogram. Cosmid DNA isolated from these positive colonies was called pPRGDHcos1, pPRGDHcos2 and pPRGDH cos3.

Chromosomal DNA isolated from Phaffia rhodozyma strain CBS 6938 and cosmid pPRGDHcos1 was digested with several restriction enzymes. The DNA fragments were separated, blotted and hybridized as described before. The autoradiograph was exposed for different time periods at −80° C. The film showed DNA fragments of different length digested by different restriction enzymes which hybridize with the GAPDH-probe (FIG. 1).

Furthermore, from Southern analysis of the genomic DNA of Phaffia using the GAPDH fragment as probe, it was concluded that the GAPDH-encoding gene is present as a single copy gene in Phaffia rhodozyma, whereas in Saccaromyces cerevisiae GAPDH is encoded by three closely related but unlinked genes (Boucherie et al., 1995. FEMS Microb. Letters 135:127–134).

Figure 2:
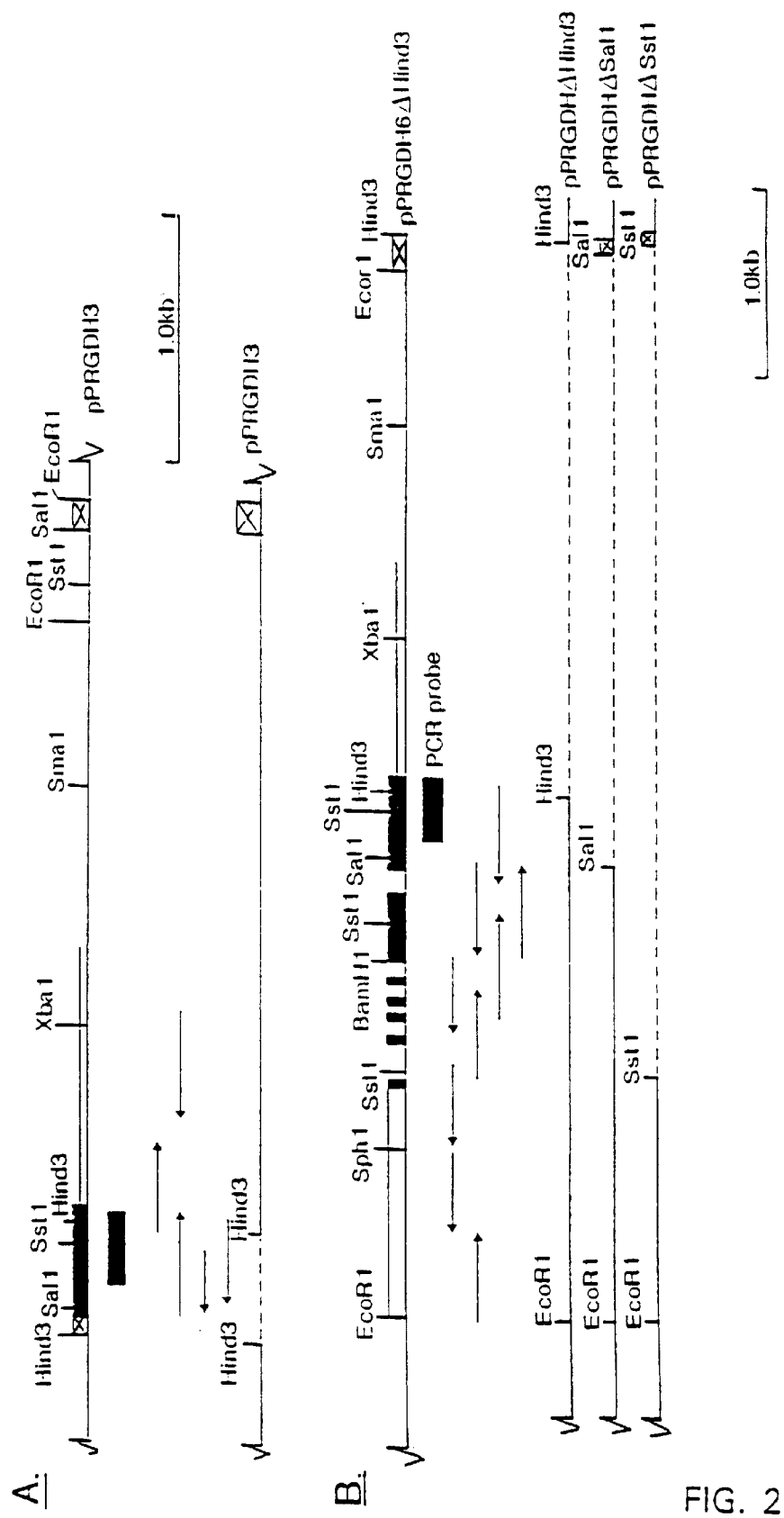
FIGS. 2A and 2B. The organisation of two subclones; pPRGDH3 and derivative (A) and pPRGDH6 and derivatives (B) containing (a part of) the GAPDH gene of *Phaffia rhodozyma*. The PCR probe is indicated by a solid box. The direction and extent of the sequence determination is indicated by arrows. solid boxes: GAPDH4 coding sequence open box: 5' upstream and promoter region of GAPDH open box: 3' non-coding *Phaffia rhodozyma* GAPDH sequence solid line: GAPDH intron hatched box: Poly-linker containing sites for different restriction enzymes dotted line: deleted fragments FIG. 3. Cloning diagram of Phaffia transformation vector; pPR2. solid box: 5' upstream and promoter sequence of GAPDH hatched box: G418 solid line: pUC19 open box: ribosomal DNA of *Phaffia rhodozyma* Only restriction sites used for cloning are indicated.

Hybridizing fragments of pPRGDHcos1 for which a fragment of the same length in the chromosomal DNA digested with the same enzyme was found, were isolated from an agarose gel. The fragments were ligated into the corresponding sites in pUC19. The ligation mixtures were transformed to competent E. coli cells. The plasmids with a 3.3-kb Sa/I insert and a 5.5-kb EcoRI insert were called pPRGDH3 and pPRGDH6, respectively. The restriction map of pPRGDH3 and pPRGDH6 is shown in FIG. 2. Analysis of the sequence data of the insert in pPRGDH1 showed us that there was a HindIII site at the C-terminal part of the GAPDH-gene. From this data it was suggested that the insert in pPRGDH6 should contain the complete coding sequence of GAPDH including promoter and terminator sequences.

EXAMPLE 4

Characterization of the GAPDH-gene

In order to carry out sequence analysis without the need to synthesize a number of specific sequence primers a number of deletion constructs of plasmids pPRGDH3 and pPRGDH6 were made using convenient restriction sites in or near the putative coding region of GAPDH gene.

The plasmids were digested and after incubation a sample of the restriction mixture was analyzed by gel electrophoresis to monitor complete digestion. After extraction with phenol-chloroform the DNA was precipitated by ethanol. After incubation at −20° C. for 30' the DNA is pelleted by centrifugation, dried and dissolved in a large volume (0.1 ng/μl) of TE. After ligation the mixtures were transformed to E. coli. Plasmid DNA isolated from these transformants was analyzed by restriction analysis to reveal the right constructs. In this way the deletion constructs pPRGDH3δHIII, pPRGDH6δBamHI, pPRGDH6δSstI and pPRGDH6δSalI (FIG. 1).

In addition to this, the 0.6-kb and 0.8-kb SstI fragments derived from pPRGDH6 were subcloned in the corresponding site of pUC 19. Sequence analysis was carried out using pUC/M3 forward and reverse primers (Promega). The sequencing stategy is shown in FIG. 2 (see arrows).

On the basis of homology with the GAPDH-gene sequence of S. cerevisiae (Holland and Holland, 1979. J. of Biol. Chem. 254: 9839–9845) and K. lactis (Shuster, 1990. Nucl. Acids Res. 18, 4271) and the known splice site concensus J. L. Woolford. 1989. Yeast 5: 439–457), the introns and the possible ATG start were postulated.

The GAPDH gene has 6 introns (FIG. 1) and encodes a polypeptide of 339 amino acids. This was completely unexpected considering the genomic organisation of the GAPDH genes of K. lactis and S. cerevisiae which have no introns and both consist of 332 amino acids. The homology on the amino acid level between the GAPDH gene of Phaffia and K. lactis and S. cerevisiae is 63% and 61%, respectively. Most of the introns in the GAPDH gene are situated at the 5' part of the gene. Except intron III all introns contain a conserved branch-site sequence 5'-CTPuAPy-3' found for S. cerevisiae and S. pombe.

By computer analysis of the upstream sequence using PC-gene 2 putative eukaryotic promoter elements, TATA-box (position 249–263 in SEQIDNO: 11) and a number of putative Cap signal (between position 287 and 302 in SEQIDNO: 11) were identified.

EXAMPLE 5

Cloning of the GAPDH Promoter Fused to G418 in pUCG418

In order to construct a transcription fusion between the GAPDH promoter and the gene encoding G418 resistence the fusion PCR technique was used. Using plasmid pPRGDH6 the GAPDH promoter could be amplified by standard PCR protocols ("Experimental").

In the PCR mix pPRGDH6 and oligo's No. 5177 and 5126 (Sequences in "Experimental") were used. A 416 bp DNA fragment was generated containing the entire GAPDH promoter sequence. In addition this fragment also contains a HindIII, XhoI and a KpnI restriction site at it's 5'end and 12 nt overlap with the 5' end of the gene encoding G418 resistance.

The 217 bp portion of the 5' end of the G418 coding sequence was also amplified by PCR using pUC-G418 and oligo's 4206 and 5127. A 226 bp DNA fragment was obtained containing the 217 bp 5' end of G418 and having a 9 nucleotides overlap with the 3' end of the earlier generated GAPDH promoter fragment. It also contained a MscI site at it's 3end.

The PCR fragments were purified from the PCR mixture using the WIZARD Kit. Approximately 1 μg of the GAPDH promoter fragment and 1 μg of the G418 PCR fragment were used together with oligo's 5177 and 4206 in a fusion PCR experiment (Experimental). A 621 bp DNA fragment was generated, containing the GAPDH promoter directly fused to the 5' portion of G418. After purification the DNA fragment was digested with MscI and KpnI. The 3.4 Kb MscI-KpnI fragment of pUC-G418, containing pUC sequences and the 3' portion of G418, was used as a vector. The ligation mixture was transformed to competent E. coli DH5 α cells. Transformant colonies containing the fusion PCR DNA inserted were identified by digestion with different restriction enzymes.

Thus, placid pPR1 was obtained containing the GAPDH promoter directly fused to the G418 marker gene. Three pPR1 vectors isolated from independent transformants were used in further cloning experiments.

Figure 3:
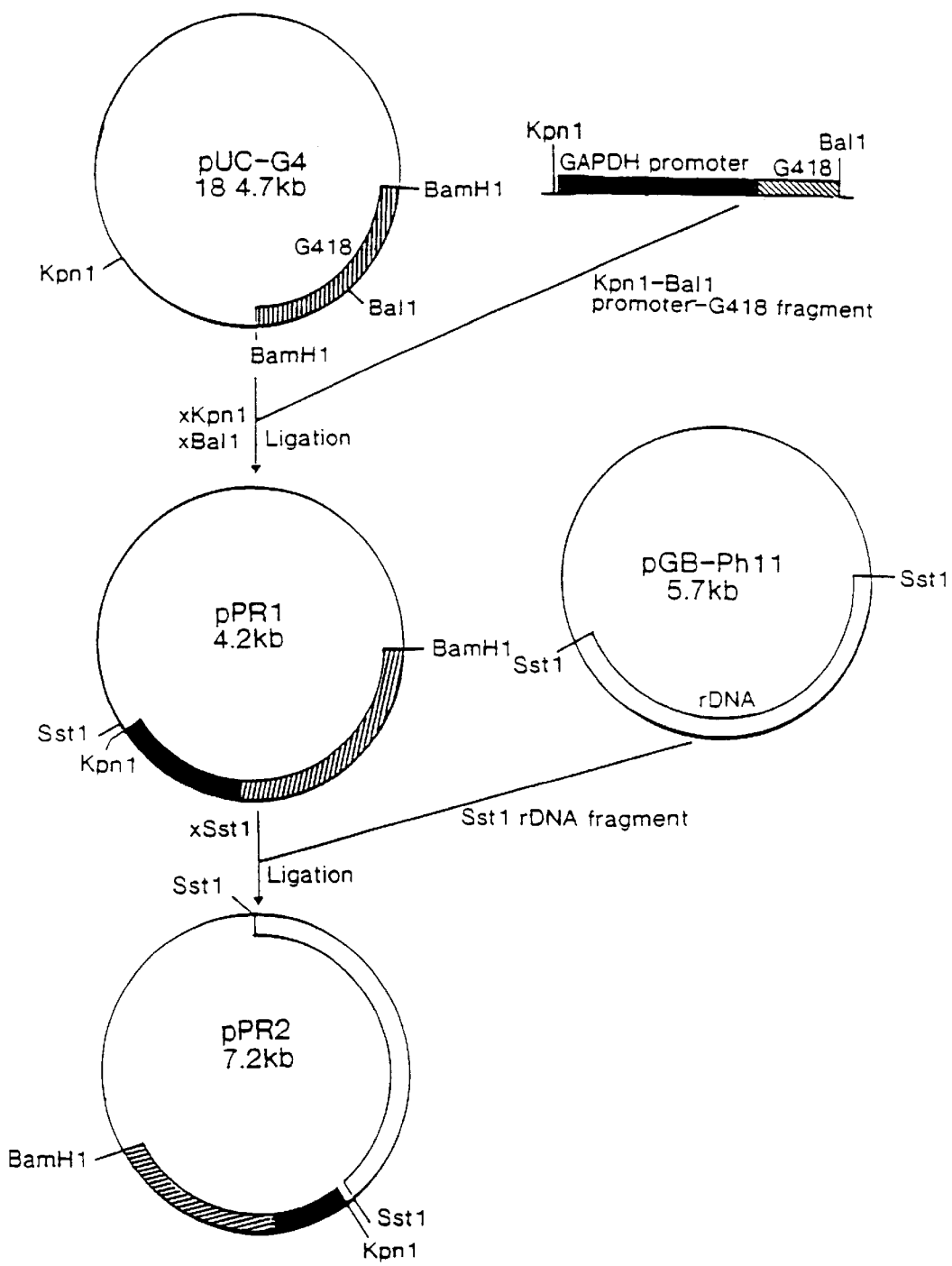
Figure 4:
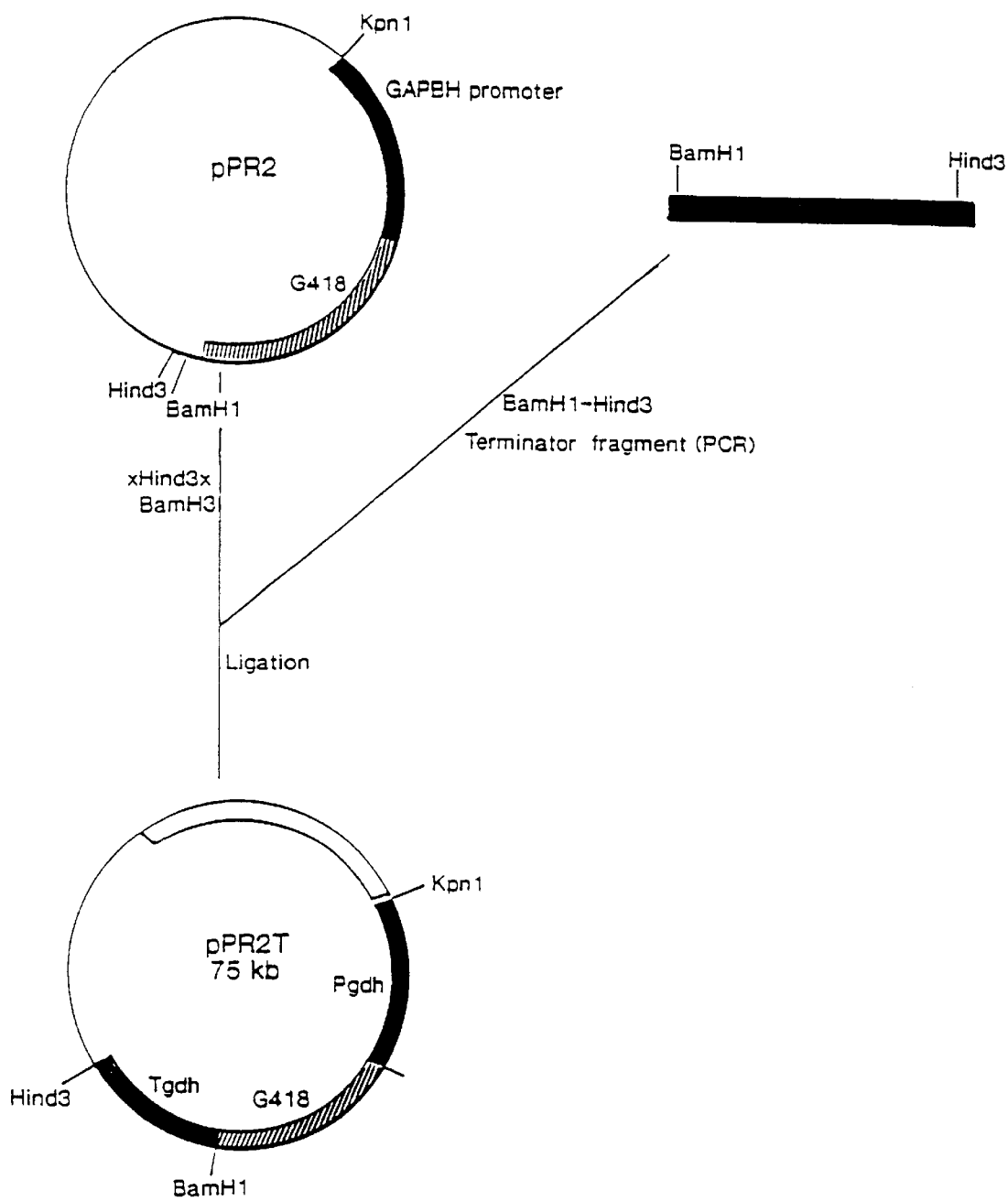
FIG. 4. Construction of pPR2T from pPR2T. Solid box (BamHI-HindIII fragment): GAPDH transcription terminator from Phaffia. All other boxes and lines are as in FIG. 3. Only relevant details have been depicted.
Figure 5:
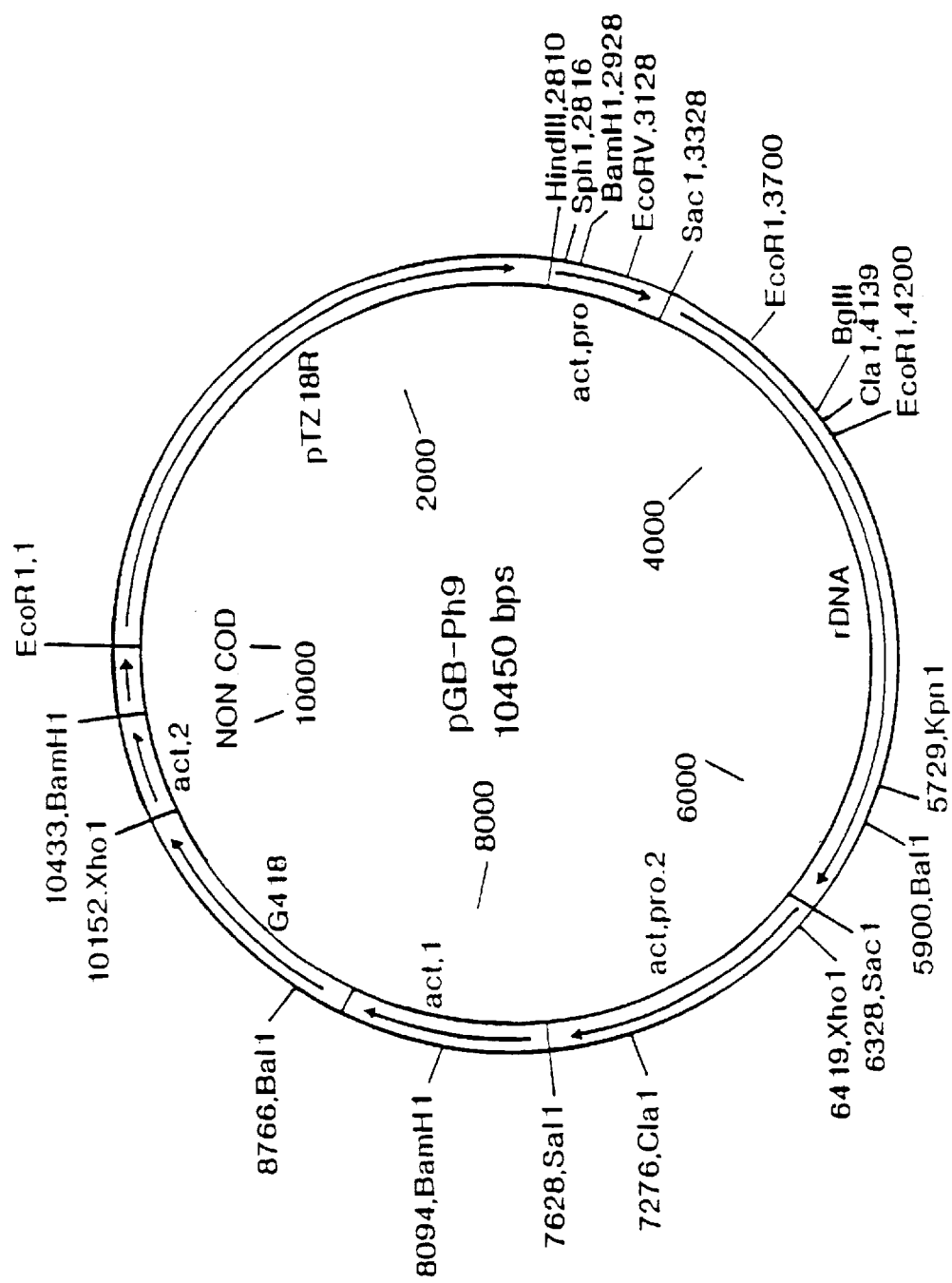
FIG. 5. Detailed physical map of pGB-Ph9. bps=basepairs; rDNA ribosomal DNA locus of Phaffia; act.pro 2=actin transcription promoter; act.1 5' non-translated and aminoterminal region of the open reading frame; NON COD.=non-coding region downstream of G418-gene.
Figure 6:
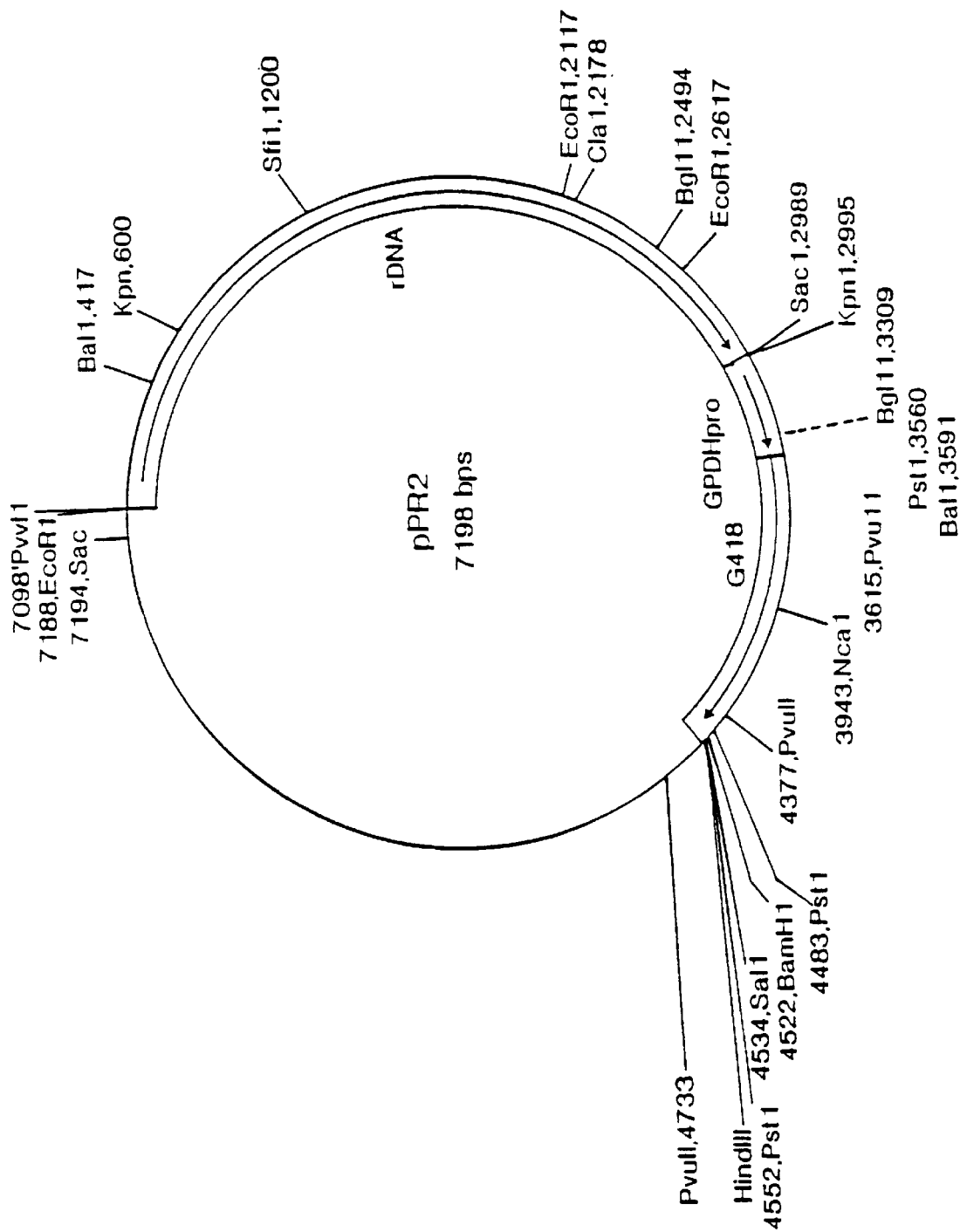
FIG. 6. Detailed physical map of pPR2. GPDHpro=GAPDH transcription promoter region from Phaffia. Other acronyms as in FIG. 5.
Figure 7:
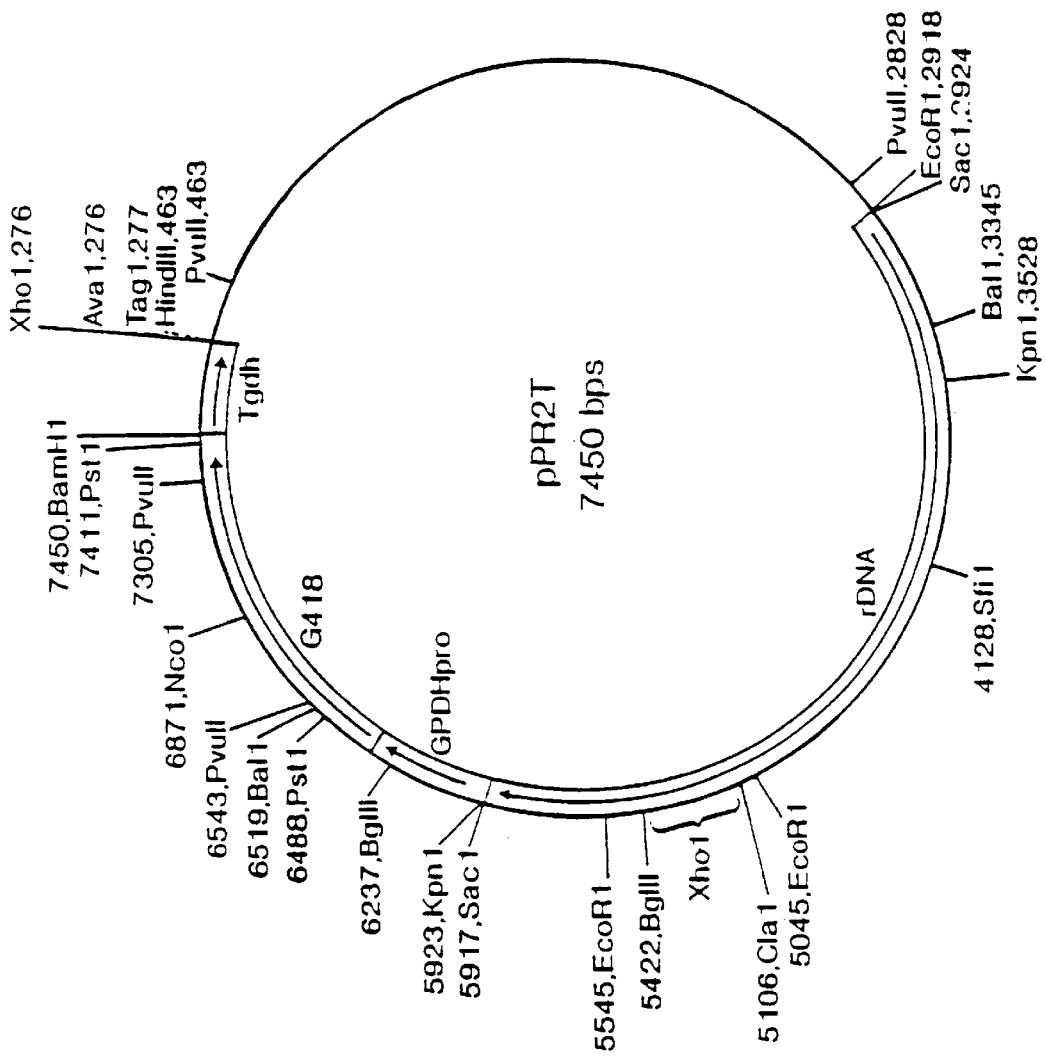
FIG. 7. Detailed physical map of pPR2T. Tgdh=GAPDH transcription terminator of Phaffia. All other acronyms as in FIGS. 5 and 6.

To target the plasmid, after transformation, to a specific integration site a 3.0-kb SstI1 fragment containing a part of the ribosomal DNA of Phaffia was cloned in pPR1. The ribosomal DNA fragment was isolated from an agarose gel after digestion with Sst1 of plasmid pGB-Ph11 (EP 590 707 A1). This fragment was ligated in the dephosphorylated Sst1 site of pPR1. The ligation mixture was transformed to competent E. coli cells. Plasmid DNA was isolated and using restriction analysis it was shown that several colonies contain the expected plasmid pPR2. The complete cloning strategy is shown in FIG. 3.

EXAMPLE 6

Transformation of Phaffia with pPR2

Transformation of Phaffia strain 6938 was performed using an electroporation procedure as previously described by Faber et al. (1994, Curr. Genet. 1994: 2,305–310) with the following modifications:

Electropulsing was performed using the Bio-rad Gene Pulser with Pulse Controller and with Bio-rad 2 mm cuvettes.

Phaffia was cultivated for 16 h at 21° C.

Per transformation $2\times10^8$ cells were used together with 5 μg of linearized vector. Linearization was done in the rDNA sequence using ClaI to enable integration at the rDNA locus in the Phaffia genome. Following the electric pulse (7.5 kV/cm, 400Ω and 25 μF) 0.5 ml YePD medium was added to the cell/DNA mixture. The mixture was incubated for 2.5 h at 21° C. and subsequently spread on 5 selective YEDP agar plates containing 40 μg/ml G(418.

As shown in Table 2 we were able to generate transformants with 115 transformants per μg DNA; the average transformation frequency was 50 transformants/g pPR2 as judged over a number of experiments. Transformation of the closed circular of pPR2 did not result in transformation suggesting that there is no autonomously replicating sequence present within the vector sequences. Using pPR2 a 10 to 50-fold increase in transformation frequency was found compared to a previous constructed transformation vector for Phaffia, called pGB-Ph9. In this latter vector a translation fusion was made between the 5' part of the actin gene of Phaffia and G418.

In order to analyze the level of resistance of transformants the mixture or DNA/cells was plated onto selective plates containing different amounts of G418. Although the total number of transformants decreases with the increasing amounts of G418, we were still able to obtain a considerable number of transformants (table 3).

In another experiment 30 transformants obtained under standard selection conditions (40 μl/ml) were transferred to plates containing 50, 200 or 1000 μg/ml . After incubation of the plates at 21° C. for 4–5 days, 23 transformants out of 30 tested were able to grow on plates containing 200 μg/ml G418. One transformant was able to grow on plates containing upto and above 1000 μg/ml G418.

TABLE 2

Transformation frequency of pGB-Ph9 and pPR2.

|  | Exp. 1 | Exp. 2 |
|---|---|---|
| — | 69 | 8 |
| pGB-Ph9xBg/II | 46 | 7 |
| pPR2 ccc | n.d | n.d |
| pPR2(A)xClaI | 714 | 56 |
| (B) | 639 | 124 |

Total number of transformants (<1 mm) in different transformation experiments after 4–5 days incubation.

TABLE 3

Comparison of G418 sensitivity as a result of two different G418-resistance genes in pGB-Ph9 and pPR2

| concentration G418 ($\mu$g/ml) | Number of transformants pPR2xClaI | PGB-Ph9xBg/II (=pYac4) |
|---|---|---|
| 40 | 480 | 2 |
| 50 | 346 | — |
| 60 | 155 | — |
| 70 | 61 | — |
| 80 | 141 | — |
| 90 | 72 | — |
| 100 | 64 | — |

Analysis of pPR2 Transformants

To analyse the integration event and the number of integrated vector copies total genomic DNA from six independent transformants was isolated. Therefore these transformants were cultivated under selective conditions, i.e. YePD+50 $\mu$g/ml G418. Chromosomal DNA was digested with ClaI. The DNA framgments were separated by gel electrophoresis and transfered to nitrocellulose and the Southern blot was probed with Phaffia DNA.

Besides the rDNA band of 9.1 kb an additional band of 7.1 kb of similar fluorescing intensity was observed in the transformants. This band corresponds to the linearised form of pPR2. From the intensity of these bands it was concluded that the copy number was about 100–140 copies of pPR2. These results are similar to those observed for pGB-Ph9, ruling out that the improved G418-resistance is due to differences in copy number of integrated vectors alone. It is not known whether the multiple copy event is caused by multiple copy integration of pPR2 or by the amplification of a single copy in the rDNA or a combination of both events.

EXAMPLE 7

Construction of pPR2T by Cloning the GAPDH-terminator into pPR2

Eukaryotic mRNAs contain modified terminal sequences, specificaly the 3' terminal poly(A). As the prokaryotic gene encoding G418 resistance lacers eukaryotic termination signals, which might effect proper transcription termination and mRNA stability (1994, Raue, H. A., TIBTECH 12: 444–449), a part of the 3' non-coding sequence of GAPDH was introduced. To that end, a 307 bp fragment, consisting of 281 bp of the 3' non-coding region of GAPDH and other additional cloning sequences, was amplified by PCR using the oligo's 5137 and 5138 ("Experimental"). The upstream oligo 5137 consists of the last 14 nucleotide& of the coding and 17 nucleotides of the 3' non-coding region of GAPDH. By base substitutions of the 5th (T→A) and 8th (T→C) nucleotide of the non-coding sequence a BamHI restriction site was introduced. In addition this fragment contains a XhoI and a HindIII restriction site at its 3' end.

The PCR fragment was purified from the PCR mixture using the WIZARD Purification Kit and digested with BamHI and HindIII. A 288 bp fragment was isolated and cloned into the corresponding sites of the previously constructed Phaffia transformation vector pPR2, yielding pPR2T.

Upon transformation of Phaffia, using G418 as selective agent, the transformation frequencies (number of transformants per jig of DNA) obtained with the improved construct pPR2T was approximately 5 to 10 times higher than the transformation frequency of pPR2 (i.e. without a Phaffia homologous transcription termination signal). The results of a typical experiment are given in Table 4.

TABLE 4

Transformation frequency at 50 $\mu$g/ml G418 for PGB-Ph9 pPR2 and pPR2T

| Vector | transformants | transformants/$\mu$g DNA |
|---|---|---|
| pGB-Ph9 (ccc) | — | — |
| pGB-Ph9 (xBg/II) | 60 | 1 |
| pPR2 (ccc) | 1 | — |
| pPR2 (xClaI) | 3000–9600 | 50–160 |
| pPR2T (ccc) | — | — |
| pPR2T (xClaI) | 45600 | 760 |
| pPR2T (xSfiI) | 1080 | 18 |

Phaffia cells transformed with pPR2T were tested for their ability to grow on high levels of G418. The level of G418 on which growth is still possible was taken as a measure of the expression level of the G418 resistance gene in transformants, as a result of the presence of the Phaffia promoter, and/or terminator. Preliminary results indicate that the number of transformants able to grow on high levels of G418 are significantly higher than without terminator.

In Summary

From the above results, it was concluded, that the presence of the GAPDH-promoter (pPR2) resulted in a considerable increase of the transformation frequency (from 1 to at least 50 per $\mu$g of DNA) when compared to the vector containing the actin-promoter (pGB-Ph9). These results are in line with the results obtained with the G418 sensitivity test (Table 3 and 4) which indicate superior expression levels under the control of the GAPDH promoter. The possibility that the difference in transformation frequency could be due solely to the difference in linearising the vectors, (BglII, ClaI and SfiI all cut inside the ribosomal DNA locus, but at different positions), was ruled out by comparison of pPR2 (xSfiI) with pGB-Ph9(xSfiI). The difference in transformation frequency between the two pPR2 and pGB-Ph9, linearised with SfiI is still considerable. However, it is concluded that the choice of the linearisation site does have effect on the transformation frequency; linearisation with ClaI is preferred.

The improvements obtained by using a high-level promoter, such as GAPDH, are irrespective of whether a homologous terminator is used (pPR2 (without homologous terminator) performs far better than pGB-Ph9, both in G418 sensitivity tests, as well as in terms of transformation frequency).

The presence of a homologous terminator results in both higher transformation frequencies and higher expression levels; this result is concluded to be independent of the promoter used. Preliminary results indicate that considerable improvements are obtained when the pGB-Ph9 construct is completed with a transcription terminator, such as the GAPDH-terminator used in pPR2T.

The following Examples illustrate the isolation of DNA encoding enzymes involved in the carotenoid biosynthesis pathway of *Phaffia rhodozyma*. These DNA sequences can suitably be used for a variety of purposes; for example to detect and isolate DNA sequences encoding similar enzymes in other organisms, such as yeast by routine hybridisation procedures, to isolate the transcription promoters and/or terminators, which can be used to construct expression vectors for both heterologous as well as homologous downstream sequences to be expressed. The DNA sequences encoding carotenoid biosynthesis genes can suitably be used to study the over-expression, either under the control of their own promoters or heterologous promoters, such as the glycolytic pathway promoters illustrated above. For example transformation of *Phaffia rhodozyma* with carotenoid encoding DNA sequences according to the invention effectively results in amplification of the gene with respect to the wild-type situation, and as a consequence, thereof to overexpression of the encoded enzyme. Hence, the effect of over-expression of one or more genes encoding carotenoid biosynthesis genes can thus be studied. It is envisaged that mutant Phaffia strains can be obtained producing higher amounts of valuable carotenoids, such as B-carotene, cantaxanthin, zeaxanthin and/or astaxanthin. Similarly, the DNA sequences encoding enzymes involved in the carotenoid biosynthesis pathway can be introduced into other hosts, such as bacteria, for example *E. coli*, yeasts, for example species of Saccharomyces, Kluyveromyces, Rhodosporidium, Candida, Yarrowia, Phycomyces, Hansenula, Picchia, fungi, such as Aspergillus, Fusarium, and plants such as carrot, tomato, and the like. The procedures of transformation and expression requirements are well known to persons skilled in these arts.

Strains:
  *E. coli* XL-Blue-MRF'Δ(mcrA)183α(mcrCB-hsdSMR-mrr) 173 endA1 supE44 thi-1 recA1 gyrA96 relA1 lac[F' proAB laq$^q$ZΔM15 Tn10 (Tet$^r$)]
    ExAssist™ interference-resistant helper phage (Stategene®)
  *P. rhodozyma* CBS6938 or
  *P. rhodozyma* asta 1043-3
Plasmids used for Cloning:
  pUC19 Ap$^r$ (Gibco BRL)
  Uni-ZAP™ XR vector (lambda ZAP®II vector digested with EcoRI-XhoI, CIAP treated;Strategene®)
Media:
  LB: 10 g/l bacto tryptone, 5 g/l yeast extract, 10 g/l NaCl. Plates: +20 g/l bacto agar.
    When appropriate 50–100 μg/ml ampicillin (Ap), 30 μg/ml chloramphenicol (Cm) and 1 mM isopropyl-1-thio-β-D-galactopyranoside (IPTG) was added.
  YePD: 10 g/l yeast extract, 20 g/l bacto peptone, 20 g/l glucose. Plates: +20 g/l bacto agar.

All molecular cloning techniques were essentially carried out as described by Sambrook et al. in Molecular Cloning: a Laboratory Manual, 2nd Edition (1989; Cold Spring Harbor Laboratory Press). Transformation of *E. coli* was performed according to the CaCl$_2$ method described by Sambrook et al.

Enzyme incubations were performed following instructions described by the manufacturer. These incubations include restriction enzyme digestion, dephosphorylation and ligation (Gibco BRL). Isolation of plasmid DNA from *E. coli* was performed using-the QIAGEN (Westburg B. V. NL).

For sequence analysis deletions constructs and oligonucleotides were made to sequence the complete sequence using a Taq DYE Primer Cycle Sequencing kit (Applied Biosystems).

EXAMPLE 8

Description of Plasmids

Figure 8:
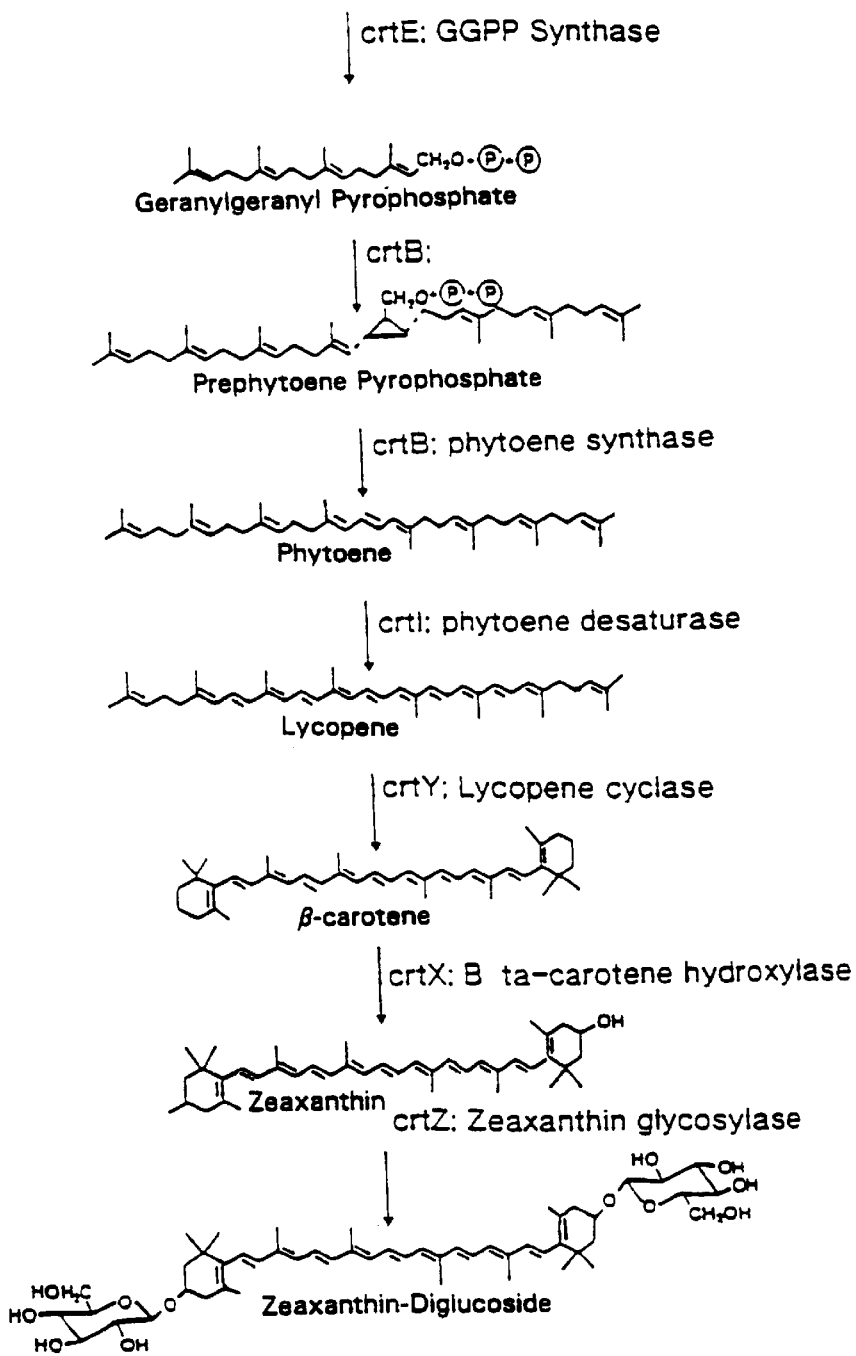
FIG. 8. Overview of the carotenoid biosynthetic pathway of *Erwinia uredovora*.
Figure 9:
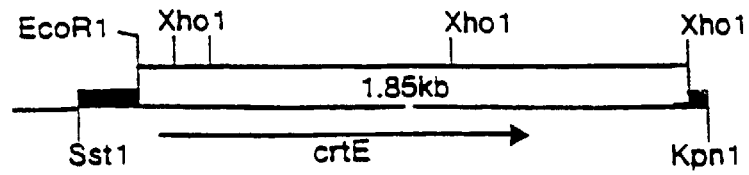
FIGS. 9a–9c. Representation of cDNA fragments and a restriction enzyme map of the plasmids pPRcrtE (A); pPR-crtB (B), pPRcrtI (C) and pPRcrtY (B).
Figure 9:
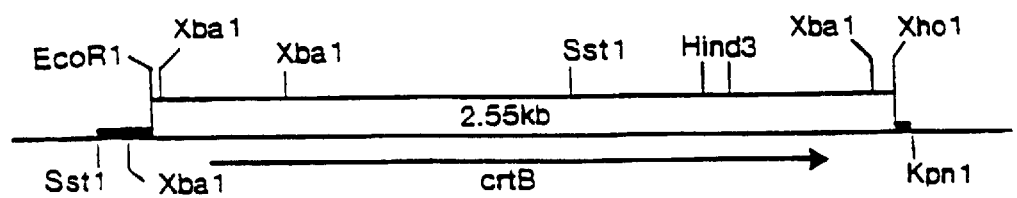
Figure 9:
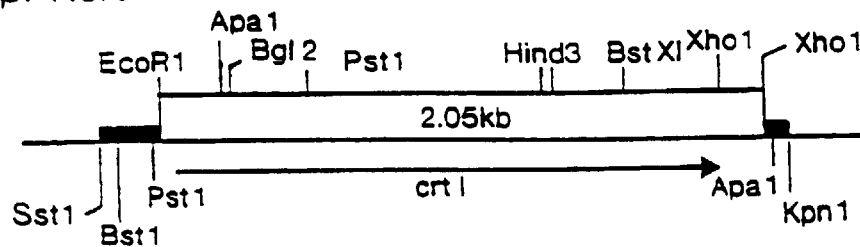

Plasmids (pACCAR25ΔcrtE, pACCAR25ΔcrtB, pACCRT-EIB, pACCAR16ΔcrtX and pACCAR25ΔcrtX), which contain different combinations of genes involved in the biosynthesis of carotenoid in *Erwinia uredovora* were gifts from Prof. Misawa; Kirin Brewery co., LTD.; Japan). The biosynthetic route of carotenoid synthesis in *Erwinia uredovora* is shown in FIG. 8.

In addition a derivative of pACCAR25ΔcrtX, designated pACCAR25ΔcrtXΔcrtX, was made in our laboratory. By the introduction of a frameshift in the BamHI restriction Site the ertl gene was inactivated. *E. coli* strains harboring this plasmid acummulate phytoene which can be monitored by the red phenotype of the colony.

All plasmids are derivatives of plasmid pACYC184 (Rose RE; Nucl. Acids Res. 16 (1992) 355), which contains a marker conferring chloramphenicol-resistance. Furthermore these plasmids and derivatives thereof contain a replication origin that is compatible to vectors such as pUC and pBluescript. Each plasmid contain a get of carotenoid biosynthetic genes of *Erwinia uredovora* mediating the formation of different carotenoid in *E. coli*. The complete list of plasmid used in this study is shown in Table 5.

TABLE 5

Summary of carotenoid producing *E. coli* strains used in this study.

| PLASMID: | GENOTYPE: | CAROTENOID ACCUMULATED: | COLOR PHENOTYPE: |
|---|---|---|---|
| pACCAR25ΔcrtE | crtB; crtI; crtY; crtX; crtZ | farnesyl pyrophosphate/iso-pentenyl pyrophosphate | white |
| pACCAR25ΔcrtB | crtE; crtI; crtY; crtX; crtZ | geranylgeranyl pyrophosphate | white |
| pACCAR25ΔcrtX ΔcrtI | crtE; crtB; crtY; crtZ | phytoene | white |
| pACCRT-EIB | crtE; crtB; crtI | lycopene | red |
| pACCAR16ΔcrtX | crtE; crtB; crtI crtY | β-carotene | yellow |
| pACCAR25ΔcrtX | crtE; crtB; crtI; crtY; crtZ | zeaxanthin | yellow/ orange |

Genes encoding: crtE, geranylgeranyl pyrophosphate synthase; crtB, Phytoene synthase; crtI, phytoene desaturase; crtY, lycopene cyclase; crtX, β-carotene hydroxylase; crtZ, zeaxanthin glycosylase

EXAMPLE 9

Construction of cDNA Library of *Phaffia rhodozyma* a) Isolation of Total RNA from *Phaffia rhodozyma*

All solutions were made in DEPC-treated distilled water and all equipments were soaked overnight in 0.1% DEPC and then autoclaved.

A 300 ml Erlemeyer containing 60 ml YePD culture medium was inoculated with *Phaffia rhodozyma* strain CBS6938/1043-3 from a preculture to a final OD$_{600}$ of 0.1. This culture was incubated at 21° C. (300 rpm) until the OD$_{600}$ had reached 3–4.

The cells were harvest by centrifugation (4° C., 8000 rpm, 5 min) and were resuspended in 12 ml of ice-cold extraction-buffer (0.1 M Tris-HCl, pH 7.5; 0.1 M LiCl; 0.1 mM EDTA). After centrifugation cells were resuspended in 2 ml of ice-cold extraction-buffer, 4 g of glassbeads (0.25 mm) and 2 ml phenol were added.

The mixture was vortexed 5 times at maximum speed for 30 s with 30 s cooling incubation intervals on ice.

The cell/glassbeads/phenol mixture was centrifuged (5 min, 15.300 rpm, 4° C.) and tho aqueous phase (sup 1) was transferred to a fresh tube and was kept on ice.

The phenolic phase was retracted by adding an additional volume of 1 ml extraction buffer and 2 ml phenol.

After centrifugation (5 min, 15.300 rpm, 4° C.). the aqueous phase was transferred to sup 1 and extracted with an equal volume phenol:chloroform.

After centrifugation (5 min, 15.300 rpm, 4° C.), the aquaous phase was transferred to a fresh tube and 0.1 volume of 3 M NaAc; pH5.5 and 2. 5 volumes of EtOH was added to precipitate RNA (incubation overnight −20° C.).

The precipitate was collected by centrifugation (10 min. 15.300 rpm, 4° C.) and drained off excess liquid and the RNA pellet was washed with 70% icecold EtOH.

After removing excess liquid the RNA was resuspended in 200–800 $\mu$l DEPC-treated water. RNA was stored at −70° C. A 60 ml culture yielded 400–1500 $\mu$g total RNA. The integrity of total RNA was checked by formaldehyde RNA gel electrophoresis.

b) Selection of poly(A)$^+$RNA

Isolation of poly(A)$^+$ from total RNA was carried out essential as described by Sambrook et al., 1989 (Molecular cloning, a laboratory manual, second edition) using the following solutions. All solutions were prepared in DEPC-treated water and autoclaved.

RNA denaturation buffer; 1 M NaCl; 18% (v/v) DMSO.
Column-loading buffer (HEND): 10 mM Hepes, pH 7.6; 1 mM EDTA; 0.5 M Na Cl; 9% (v/v) DMSO.
Elution buffer (HE): 10 mM Hepes, pH 7.6; 1 mM EDTA.
Oligo(dT)-cellulose Type 7 was supplied by Pharmacia Biotech. 0.1 g (dry weight) of oligo(dT)-cellulose was add to 1 ml HEND and the suspension was gently shaked for 1 h at 4° C. Total RNA (1.5 mg dissolved in 500 $\mu$l) and 1 ml 1 M NaCl; 18%/ (v/v) DMSO was heated to 65° C. for 5 min. Then 600 $\mu$l NaCl/DMSO was added to the RNA, mixed and placed on ice for 5 min. The poly(A)$^+$ isolation was carried out be two cycles of purification. The final yield was about 45 $\mu$g poly(A)$^+$ RNA.

c) cDNA Synthesis cDNAs were synthesized from 7.5 $\mu$g poly(A)$^+$-RNAs using the cDNA Synthesis Kit (#200401;

Strategene®). Synthesis was carried out according to the instruction manual with some minor modification.

SuperScript™ II RNase H$^-$ Reverse Transcriptase (Gibco BRL) was used in the first strand reaction instead of MMLV-RT.

The following reagents were add in a microcentrifuge:

3 $\mu$l of poly(A)$^+$ RNAs

2 $\mu$l of linker-primer 23.5 $\mu$l DMQ

Incubate 10 min 70° C., spin quickly in microcentrifuge and add,

10 $\mu$l of 5×First Strand Buffer (provided by Gibco BRL)

5 $\mu$l of 0.1 M DTT (provided by Gibco BRL)

3 $\mu$l of first strand methyl nucleotide mixture

1 $\mu$l of RNase Block Ribonuclease Inhibitor (40 U/$\mu$l)

Annealling of template and primers by incubation the mixture at 25° C. for 10 min followed by 2 min at 42° C. and finally add;

2.5 $\mu$l SuperScript™ II RNase H$^-$ Reverse Transcriptase First-strand reaction was carried out at 42° C. for 1 h.

Size fractionation was carried out using Geneclean® II kit (supplied BIO 101, Inc.). The volume of the cDNA mixture obtained after XhoI digestion was brought up by adding DMQ to a final volume of 200 $\mu$l. Three volumes of NaI was added and the microcentrifuge tube was placed on ice for 5 min. The pellet of glassmilk was washed three times using 500 l New Wash. Finally the cDNA was eluted in 20 $\mu$l DMQ.

The yield of cDNA was about 1 $\mu$g using these conditions.

d) cDNA Cloning cDNA library was constructed in the Uni-ZAP™ XR vector using 100 ng cDNAs. Ligation was performed two times overnight incubation at 12° C. The cDNA library was packaged using the Packagene® lambda DNA packaging system (Promega) according to the instruction manual. The calculated titer of the cDNA library was 3.5 10$^6$ pfu.

e) Mass excission

Mass excision was carried out described in the protocol using derivatives of *E. coli* XL-Blue-MRF' as acceptor strain (see Table 5). Dilution of cell mixtures were plated onto 145 mm LB agar plates containing ampicillin, chloramphenicol and IPTG, yielding 250–7000 colonies on each plate. The plates were incubatied overnight at 37° C. and further incubated one or two more days at room temperature.

EXAMPLE 10

Cloning of the Geranylgeranyl Pyrophosphate Synthase Gene (crtE) of *Phaffia rhodozyma* a) Isolation of cDNA Clone

The entire library was excised into a farnesylpyrophosphate/isopentenyl pyrophosphate accumulating cells of *E. coli* XL-Blue-MRF, which carries the plasmid pACCAR25ΔcrtE (further indicated as XL-Blue-MRF'[pACCAR25ΔcrtE]). The screening for the crtE gene was based on the color of the transformants. Introduction of the crtB gene in a genetic background of XL-Blue-MRF' [pACCAR25ΔcrtE] would result in a restoration of the complete route for the biosynthesis of zeaxanthin-diglucoside, which could be monitored by the presence of a yellow/orange pigmented colony. About 8.000 colonies were spread on LB agar plates containing appropriate antibiotics and IPTG. One colonie was found to have changed to a yellow/orange color.

b) Characterization of Complementing cDNA Clone

These colonies were streaked on LB-ampicillin agar plates. Plasmid DNA was isolated from this yellow colonies and found to include a 1.85 kb fragment (FIG. 2A). The resulting plasmid, designated pPRcrtE, was used for retransformation experiments (Table 6). Only the transformation of XL-Blue-MRF'[pACCAR25ΔcrtE] with pPRcrtE resulted in a white to yellow color change in phenotype. To test whether the color change was due to complemention and not caused by cDNA alone pPRcrtE was transformed into XL-Blue-MRF'. Selection of transformants on LB-ampicillin agar plate containing IPTG did not result in color changes of the colonies (Table 6). Therefore we tentatively concluded, that we have cloned a cDNA of *P. rhodozyma* encoding GPPP synthase which is involved in the conversion of IPP and FPP to GGPP.

TABLE 6

Color phenotype of carotenoid producing *E. coli* strains transformed with pPRcrtE.

| | pUCI9 (control) | pPRcrtE |
|---|---|---|
| XL-Blue-MRF' (Ap, IPTG) | white | white |
| XL-Blue-MRF' [pACCAR25ΔcrtE] (Ap, Cm, IPTG) | white | yellow/orange |
| XL-Blue-MRF' [pACCAR25ΔcrtB] (Ap, Cm, IPTG) | white | white |

Transformation: 10 ng of each plasmid was mixed to CaCl, competent *E. coli* cells. Transforment cells were selected by plating 1/10 and 1/100 volume of the DNA/cell mixture on LB agar-medium containing the appropriate antibiotics (in brackets).

c) Sequence Analysis of cDNA Fragment

Plasmid pPRcrtE was used to determine the nucleotide sequence of the 1.85 kb cDNA.

The sequence comprised 1830 nucleotides and a 31 bp poly(A) tail. An open reading frame (ORF) of 375 amino acids was predicted. The nucleotide sequence and deduced amino acid sequence are shown as SEQIDNO NO: 14 and 15, respectively. A search in SWISS-PROT protein sequence data bases using the Blitz amino acid sequence alignment program indicated amino acid homology (52% in 132 aa overlap; *Neurospora crassa*) especially to the conserved domain I in geranylgeranyl-PPi synthase enzymes of different organisms (Botella et al., Eur. J. Biochem. (1995) 233; 238–248).

EXAMPLE 11

Cloning of the Phytoene Synthase Gene (crtB) of *Phaffia rhodozyma*

Isolation of cDNA Clone

The entire library was excised into a geranylgeranylpyrophosphate accumulating cells of *E. coli* XL-Blue-MRF', which carries the plasmid pACCAR25ΔcrtB (further indicated as XL-Blue-MRF'[pACCAR25ΔcrtB]). The screening for the crtB gene was based on the color of the transformants.

Introduction of the crtB gene in a genetic background of XL-Blue-MRF'[pACCAR25ΔcrtB] would result in a restoration of the complete route for the biosynthesis of zeaxanthin-diglucoside, which could be monitored by the presence of a yellow/orange pigmented colony.

About 25.000 colonies were incubated on LB agar plates containing appropriate antibiotics and IPTG. Three colonies were found to have changed to a yellow/orange color.

b) Characterization of Complementing cDNA Clone

These colonies were streaked on LB-ampicillin agar plates. Plasmid DNA, designated pPRcrtB1 to 3, was isolated from these yellow colonies and found to include a 2.5 kb fragment (FIG. 2B). One of the resulting plasmids, pPRcrtB1 was used for retransformation experiments (Table 7). Only the transformation of XL-Blue-MRF' [pACCAR25ΔcrtB] with pPRcrtB resulted in a white to yellow color change in phenotype. Therefore we tentative conclude that we have cloned a cDNA of *P. rhodozyma* encoding phytoene synthase which is involved in the conversion of 2 GGPP molecules via prephytoene pyrophosphate into phytoene.

TABLE 7

Color phenotype of carotenoid producing *E. coli* strains transformed with pPRcrtB.

| | pUC19 (control) | pPRcrtB |
|---|---|---|
| XL-Blue-MRF' (Ap, IPTG) | white | white |
| XL-Blue-MRF' [pACCA25ΔcrtB (Ap, Cm, IPTG) | white | yellow/orange |
| XL-Blue-MRF' [pACCA25ΔcrtE (Ap, Cm, IPTG) | white | white |

Legend: see Table 6.

c) Sequence Analysis of cDNA Fragment

Plasmid pPRcrtB2, which contains the longest cDNA insert, was used to determine the nucleotide sequence of the 2.5 kb cDNA. The sequence comprised 2483 nucleotides and a 20 bp poly(A) tail. An open reading frame (ORF) of 684 amino acids was predicted. The nucleotide sequence and deduced amino acid sequence are shown in SEQIDNOs: 12 and 11, respectively. A search in SWISS-PROT protein sequence data bases using the Blitz amino acid sequence alignment program Data indicated some amino acid homology (26% identity in 441 aa overlap of crtB gene of *Neurospora crassa*) with crtB genes of other organisms.

EXAMPLE 12

Cloning of the Phytoene Desaturase Gene (crtI) of *Phaffia rhodozyma* a) Isolation of cDNA Clone

The entire library was excised into a phytoene accumulating cells of *E. coli* XL-Blue-MRF', which carries the plasmid pACCAR25ΔcrtXΔcrtI (further indicated as XL-Blue-MRF'[pACCAR25ΔcrtXΔcrtI]). The screening for the crtI gene was based on the color of the transformants. Introduction of the crtI gene in a genetic background of XL-Blue-MRF'[pACCAR25ΔcrtXΔcrtI] would result in a restoration of the complete route for the biosynthesis of zeaxanthin, which could be monitored by the presence of a yellow/orange pigmented colony.

About 14.000 colonies were incubated on LB agar plates containing appropriate antibiotics and IPTG. Two colonies were found to have changed to a yellow/orange color.

b) Characterization of Complementing cDNA Clones

These colonies were streaked on LB-ampicillin agar plates. Plasmid DNA, designated pPRcrtI.1 and pPRcrtI.2, was isolated from these yellow colonies and found to include a 2.0 kb fragment (FIG. 2C). One of the resulting plasmids, pPRcrtI.1 was used for retransformation experiments (Table 8). Only the transformation of XL-Blue-MRF' [pACCAR25ΔcrtXΔcrtI] with pPRcrtI resulted in a white to yellow color change in phenotype. Therefore we tentative conclude that we have cloned a cDNA of *P. rhodozyma* encoding phytoene desaturase which is involved in the conversion of phytoene to lycopene.

TABLE 8

Color phenotype of carotenoid producing *E. coli* strains transformed with pPRcrtI.

| | pUCI9 | pPRcrtI |
|---|---|---|
| XL-Blue-MRF' (Ap, IPTG) | white | white |

TABLE 8-continued

Color phenotype of carotenoid producing E. coli strains transformed with pPRcrtI.

|  | pUCl9 | pPRcrtI |
|---|---|---|
| XL-Blue-MRF' [pACCA25ΔcrtX ΔcrtI] (Ap, Cm, IPTG) | white | yellow/orange |
| XL-Blue-MRF' [pACCA25ΔcrtB] (Ap, Cm, IPTG) | white | white |

Legend: see Table 6.

c) Sequence Analysis of cDNA Fragment

One of the plasmid pPRcrtI was used to determine the nucleotide sequence of the 2.0 kb cDNA. The sequence comprised 2038 nucleotides and a 20 bp poly(A) tail. An open reading frame (ORF) of 582 amino acids was predicted. The nucleotide sequence and deduced amino acid sequence are shown in SEQIDNOs: 16 and 17, respectively. A search in SWISS-PROT protein sequence data bases using the Blitz amino acid sequence alignment program Data indicated amino acid homology to phytoene desaturase gene of *N. crassa* (53% identity in 529 aa overlap).

EXAMPLE 13

Cloning of the Lycopene Cyclase Gene (crtY) of *Phaffia rhodozyma* a) Isolation of cDNA Clone

The entire library was excised into a lycopene accumulating cells of *E. coli* XL-Blue-MRF', which carries the plasmid pACCRT-EIB (further indicated as XL-Blue-MRF' [pACCRT-EIB]). The screening for the crtY gene was based on the color of the transformant. Introduction of the crtY gene in a genetic background of XL-Blue-MRF'[pACCRT-EIB] would result in a restoration of the complete route for the biosynthesis of β-carotene, which could be monitored by the presence of a yellow pigmented colony. About 8.000 colonies were incubated on LB agar plates containing appropriate antibiotics and IPTG. One colony was found to have changed to a yellow color.

b) Characterization of Complementing cDNA Clone

This colony was streaked on LB-ampicillin agar plates. Plasmid DNA was isolated from this yellow colony and found to include a 2.5 kb fragment (FIG. 2B). The resulting plasmid, designated pPRcrtY, was used for retransformation experiments (Table 9. Surprisingly, not only transformation of XL-Blue-MRF'[pACCRT-EIB] but also transformation of XL-Blue-MRF'[pACCAR25ΔcrtB] with pPRcrtY resulted in a red to yellow color change in phenotype.

TABLE 9

Color phenotype of carotenoid producing E. coli strains transformed with pPRcrtY.

|  | pUC19 | pPRcrtB |
|---|---|---|
| XL-Blue-MRF' (Ap, IPTG) | white | white |
| XL-Blue-MRF' [pACCRT-EIB (Ap, Cm, IPTG) | red | yellow |

TABLE 9-continued

Color phenotype of carotenoid producing E. coli strains transformed with pPRcrtY.

|  | pUC19 | pPRcrtB |
|---|---|---|
| XL-Blue-MRF' [pACCA25ΔcrtB] (Ap, Cm, IPTG) | red | yellow |

Legend: see Table 6.

A second transformation experiment was carried out including the previously cloned cDNA of pPRcrtB. As shown in table 6 the cDNA previously (example 3) isolated as encoding phytoene synthase was able to complement the crtY deletion resulting in the biosynthesis of β-carotene in XL-Blue-MRF'[pACCRT-EIB].

Sequence analysis of the cDNA insert of pPRcrtY (SEQIDNOs: 18 and 19) showed that it was similar to the sequence of cDNA fragment of pPRcrtB.

From these data we tentative conclude that we have cloned a EDNA of *P. rhodozyma* encoding phytoene synthase and lycopene cyclase which is involved in the conversion of 2 GGPP molecules via prephytoene pyrophosphate into phytoene and lycopene to β-carotene, respectively. This is the first gene in a biosynthetic pathway of carotenoids synthesis that encodes two enzymatic activities.

TABLE 10

Color phenotype of carotenoid producing E. coli strains transformed with different cDNAs of Phaffia rhodozyma (Ap, Cm, IPTG).

|  | pUC19 | pPRcrtE | pPRcrtB | pPRcrtY |
|---|---|---|---|---|
| XL-Blue-MRF' (pACCAR25ΔcrtE] | white | yellow/orange | white | white |
| XL-Blue-MRF' [pACCA25ΔcrtB] | white | white | yellow/orange | yellow/orange |
| XL-Blue-MRF' [pACCRT-EIB] | red | red | yellow | yellow |

Legend: see Table 6

EXAMPLE 14

Cloning of the Isopentenyl Diphosphate (IPP) Isomerase Gene (idi) of *Phaffia rhodozyma* a) Isolation of cDNA Clone

The entire Phaffia cDNA library was excised into lycopene accumulating cells of *E. coli* XL-Blue-MRF', each carrying the plasmid pACCRT-EIB (further indicated as XL-Blue-MRF'[pACCRT-EIB]). About 15.000 colonies were incubated on LB agar plates containing appropriate antibiotics and IPTG. One colony was found to have a dark red colour phenotype.

b) Characterization of Complementing cDNA Clone

This colony was streaked on LB-ampicillin agar plates. Plasmid DNA was isolated from this yellow colony and found to include a 1.1 kb fragment. The resulting plasmid, designated pPRcrtX, was used for retransformation experiments (Table 11).

All colonies of XL-Blue-MRF'[pACCAR-EIB] transformed with pPRcrtX had a dark red phenotype. From these data we tentatively concluded, that we have cloned a cDNA of *P. rhodozyma* expression of which results in an increased lycopene production in a genetically engineered *E. coli* strain.

TABLE 11

Color phenotype of carotenoid producing *E. Coli* strains transformed with pPRcrtX.

|  | pUC19 | pPRcrtX |
|---|---|---|
| XL-Blue-MRF' (Ap, IPTG) | white | white |
| XL-Blue-MRF' [pACCRT-EIB (Ap Cm, IPTG) | red | dark red |

Legend: see Table 6 c) Sequence Analysis of cDNA Fragment

It order to resolve the nature of this gene the complete nucleotide sequence of the cDNA insert in pPRcrtX was determined. The nucleotide sequence consist of the 1144 bp. The sequence comprised 1126 nucleotides and a poly(A) tail of 18 nucleotides. An open reading frame (ORF) of 251 aminoacids with a molecular mass of 28.7 kDa was predicted. The nucleotide sequence and deduced amino acid sequence are shown in SEQIDNOs: 20 and 21, respectively.

A search in SWISS-PROT protein sequence data bases using the Blitz amino acid sequence alignment program Data indicated aminoacid homology to isopentenyldiphosphate (IPP) isomerase (idi) of *S. cerevisiae* (42.2% identity in 200 aminoacid overlap). IPP isomerase catalyzes an essential activation step in the isoprene biosynthetic pathway which synthesis the 5-carbon building block of carotenoids. In analogy to yeast the gene of Phaffia was called idi1. The cDNA clone carrying the genes was then called pPRidi.

EXAMPLE 15

Overexpression of the idi Gene of *P. rhodozyma* in a Carotenogenic *E. coli*

Lycopene accumulating cells of *E. coli* XL-Blue-MRF', which carry the plasmid pACCRT-EIB (further indicated as XL-Blue-MRF'[pACCRT-EIB]) were transformed with pUC19 and pPRidi and transformants were selected on solified LB-medium containing Amp and Cm. The transformants, called XL-Blue-MRF'[pACCRT-EIB/pUC19 and [pACCRT-EIB/pPRidi], were cultivated in 30 ml LB-medium containing Amp, Cm and IPTG at 3° C. at 250 rpm for 16 h. From these cultures 1 ml was used for carotenoid extraction and analysis. After centrifugation the cell pellet was dissolved in 200 µl aceton and incubated at 65°C. for 30 minutes. Fifty µl of the cell-free aceton fraction was then used for high-performance liquid chromatography (HPLC) analysis. The column (chrompack cat. 28265; packing nucleosil 100C18) was developed with water-acetonitrile-2-propanol (from 0 to 45 minutes 9:10:81 and after 45 minutes 2:18:80) at a flow rate of 0.4 ml per minute and recorded with a photodiode array detector at 470+/−20 nm. Lycopene was shown to have a retention time of about 23 minutes under these conditions. The peak area was used as the relative lycopene production (mAu*s). The relative lycopene production was 395 and 1165 for XL-Blue-MRF' [pACCRT-EIB/pUC19] and [pACCRT-EIB/pPRidi], respectively.

These data show the potentials of metabolic pathway engineering in Phaffia, as increased expression of the idi of *Phaffia rhodozyma* causes a 3-fold increase in carotenoid biosynthesis in *E. coli*.

This cDNA may be over-expressed in a transformed Phaffia cell with a view to enhance carotenoid and/or xanthophyll levels. The cDNA is suitably cloned under the control of a promoter active in Phaffia, such as a strong promoter according to his invention, for example a Phaffia glykolytic pathway promoter, such as the GAPDH-gene promoter disclosed herein, or a Phaffia ribosomal protein gene promoter according to the invention (vide sub). Optionally, the cDNA is cloned in front of a transcriptional terminator and/or polyadenylation site according to the invention, such as the GAPDH-gene terminator/polyadenylation site. The feasibility of this approach is illustrated in the next example, where the crtB gene from *Erwinia uredovora* is over-expressed in *Phaffia rhodozyma* by way of illustration.

EXAMPLE 16

Heterologous Expression of Carotenogenic Gene from *Erwinia uredovora* in *Phaffia rhodozyma*

The coding sequence encoding phytoene synthase (crtB) of *Erwinia uredovora (Misawa et al., 1990)* was cloned between the promoter and terminator sequences of the gpd (GAPDH-gene) of Phaffia by fusion PCR. In two separate PCR reactions the promoter sequence of gpd and the coding sequence of crtB were amplified. The former sequence was amplified using the primers 5177 and 5128 and pPR8 as template. This latter vector is a derivative of the Phaffia transformation vector pPR2 in which the promoter sequence has been enlarged and the BglII restriction site has been removed. The promoter sequence of gpd was amplified by PCR using the primers 5226 and 5307 and plasmid pPRgpd6 as template. The amplified promoter fragment was isolated, digested with KpnI and BamHI and cloned in the KpnI-BglII fragment of vector pPR2, yielding pPR8. The coding sequence of crtB was amplified using the primers 5131 and 5134 and pACCRT-EIB as template. In a second fusion PCR reaction, using the primers 5177 and 5134, 1 µg of the amplified promoter and crtB coding region fragment used as template yielding the fusion product Pgpd-crtB. The terminator sequence was amplified under standard PCR conditions using the primers 5137 and 5138 and the plasmid pPRgdh6 as template. Primer 5137 contains at the 5' end the last 11 nucleotides of the coding region of the crtB gene of *E. uredovora* and the first 16 nucleotides of the terminator sequence of gpd gene of *P. rhodozyma*. By a two basepair substitution a BamHI restriction site was introduced. The amplified fusion product (Pgpd-crtB) and the amplified terminator fragments were purified and digested with HindIII and BamHI and cloned in the dephosphorylated HindIII site of the cloning vector pMTL25. The vector with the construct Pgpd-crtB-Tgpd was named pPREX1.1.

The HindIII fragment containing the expression cassette Pgpd-crtB-Tgpd was isolated from pPREX1.1 and ligated in the dephosphorylated HindIII site of the Phaffia transformation vector pPR8. After transformation of the ligation mixture into *E. coli* a vector (pPR8crtB6.1) with the correct insert was chosen for Phaffia transformation experiments.

Phaffia strain CBS6938 was transformed with pPRacrtB6.1, carrying the expression cassette Pgpd-crtB-Tgpd, and transformants were selected on plates containing G418. The relative amount of astaxanthin per $OD_{600}$ in three G418-resistant transformants and the wild-type Phaffia strains was determined by HPLC analysis (Table 12). For carotenoid isolation from Phaffia the method of DMSO/hexane extraction described by Sedmak et al., (1990; Biotechn. Techniq. 4, 107–112) was used.

TABLE 12

The relative astaxanthin production in a Phaffia transformant carrying the crtB gene of *E. uredovora*.

| Strain: | Relative amount of astaxanthin (mAU*s/OD$_{660}$) |
|---|---|
| *P. rhodozyma* CBS6938 | 448 |
| *P. rhodozyma* CBS6938 | |
| [pPR8crtB6.1]#1 | 626 |
| [pPR8crtB6.1]#2 | 716 |
| [pPR8crtB6.1]#4 | 726 |

Primers used:
5128: 5' caactgccat*gatggtaagagtgttagag* 3'
5177: 5' ccc<u>aagctttctcgag</u>gtacctggtgggtgcatgtatgtac3'
5131: 5' ta<u>ccatc</u>atggcagttggctcgaaaag 3'
5134: 5' ccc<u>aagcttggatccgt</u>ctagagcgggcgctgcc3'
5137: 5' ccaaggcctaaacggatc<u>cc</u>tccaaacc 3'
5138: 5' gcc<u>aagcttctcgag</u>cttgatcagataaagatagagat3'
5307: 5' gttgaagaagggatc<u>c</u>ttgtggatga 3'

The gpd sequences are indicated in bold, the crtB sequences in italic, additional restriction sites for cloning are underlined and base substitution are indicated by double underlining.

EXAMPLE 17

Isolation and Characterization of the crtB Gene of Phaffia

It will also be possible to express the *Phaffia rhodozyma* gene corresponding to crtB and express it under the control of its own regulatory regions, or under the control of a promoter of a highly expressed gene according ot the invention. The Phaffia transformation procedure disclosed herein, invariably leads to stably integrated high copy numbers of the introduced DNA, and it is expected, that expression of the gene under the control of its own promoter will also lead to enhanced production of carotenoids, including astaxanthin. To illustrate the principle, a protocol is given for the cloning of the crtB genomic sequence, below.

To obtain the genomic crtB-gene including expression signals the 2.5 kb BamHI-XhoI fragment was isolated from the vector pPRcrtB and used as probe to screen a cosmid library of Phaffia. The construction and screening of the library was carried out as described in Example 3 using the crtB gene as probe instead of the gapdh-gene.

After the rounds of hybridization, 2-colonies were identified giving a strong hybridization signal on the autoradiogram after exposure. Cosmid DNA isolated from these colonies was called pPRgcrtB#1.1 and pPRgcrtB#7, respectively.

Chromosomal DNA isolated from *Phaffia rhodozyma* strain CBS 6938 and cosmid pPRgcrtB#7 was digested with several restriction enzymes. The DNA fragments were separated, blotted and hybridized with a amino-terminal specific probe (0.45 kb XbaI fragment) of crtB under conditions as described before. After exposure, the autoradiogram showed DNA fragments of different length digested by different restriction enzymes which hybridized with the crtB probe. On the basis that no EcoRI site is present in the cDNA clone a EcoRI fragment of about 4.5 kb was chosen for subcloning experiments in order to determine the sequence in the promoter region and to establish the presence of intron sequences in the crtB gene. A similar sized hybridizing fragment was also found in the chromosomal DNA digested with EcoRI, The fragment was isolated from an agarose gel and ligated into the corresponding site of pUC19. The ligation mixture was transformed to competent *E. coli* cells. Plasmids with the correct insert in both orientations, named pPR10.1 and pPR10.2, were isolated from the transformants. Comparison of the restriction patterns of pPR10.1/pPR10.2 and pPRcrtB digested with XbaI gave an indication for the presence of one or more introns as the internal 2.0 kb XbaI fragment in the cDNA clone was found to be larger in the former vectors. The subclone pPR10.1 was used for sequence analysis of the promoter region and the structural gene by the so-called primer walking approach. The partial sequence of the insert in show in SEQIDNO: 22. Comparison of the cDNA and the genomic sequence revealed the presence of 4 introns.

EXAMPLE 18

Isolation of Promoter Sequences with High Expression Levels

This example illustrates the the feasibility of the "cDNA sequencing method" referred to in the detailed description, in order to obtain transcription promoters from highly expressed genes.

For the isolation and identification of transcription promoter sequences from *Phaffia rhodozyma* genes exhibiting high expression levels, the cDNA library of *Phaffia rhodozyma* was analyzed by the following procedure.

The cDNA library was plated on solified LB-medium containing Amp and 96 colonies were randomly picked for plasmid isolation. The purified plasmid was digested with XhoI and XbaI and loaded on a agarose gel. The size of the cDNA inserts varied from 0.5 to 3.0 kb. Subsequently, these plasmids were used as template for a single sequence reaction using the T3 primer. For 17 cDNA clones; no sequence data were obtained. The sequences obtained were translated in all three reading frames. For cDNA sequence the longest deduced amino acid sequences were compared with the SwissProt protein database at EBI using the Blitz program. For 18 deduced amino acid sequences no homology to n proteins was found whereas six amino acid sequences showed significant homology to hypothetical proteins. Fifty-five amino acid sequences were found to have significant homology to proteins for which the function is known. About 50% (38/79) were found to encode ribosomal proteins os which 12 full-length sequences were obtained.

TABLE 13

Overview of expressed cDNAs, encoded proteins and reference to the Sequence Listing

| cDNA | coding for | SEQIDNO: |
|---|---|---|
| 10 | ubiquitin-40S | 24 |
| 11 | Glu-repr.gene | 26 |
| 18 | 40S rib.prot S27 | 28 |
| 35 | 60S rib.prot P1α | 30 |
| 38 | 60S rib.prot L37e | 32 |
| 46 | 60S rib.prot L27a | 34 |
| 64 | 60S rib.prot L25 | 36 |
| 68 | 60S rib.prot P2 | 38 |
| 73 | 40S rib.prot S17A/B | 40 |
| 76 | 40S rib.prot S31 | 42 |
| 78 | 40s rib.prot S10 | 44 |
| 85 | 60S rib.prot L37A | 46 |

TABLE 13-continued

Overview of expressed cDNAs, encoded proteins and reference to the Sequence Listing

| cDNA | coding for | SEQIDNO: |
|------|------------|----------|
| 87 | 60S rib.prot L34 | 48 |
| 95 | 60S rib.prot S16 | 50 |

By sequence homology it was concluded that in Phaffia the 40S ribisomal protein S37 is fused to ubiquitin as is found in other organisms as well. The nucleotide sequences and deduced amino acid sequences of the full length cDNA clones are listed in the sequence listing. Six ribosomal proteins were represented in the random pool by more than one individual cDNA clone. The 40S ribosomal proteins S10 (SEQIDNO:44), S37 (+ ubiquitin) (SEQIDNO:24) and S27 (SEQIDNO:28) were represented twice and 60S (acidic) ribosomal proteins P2 (SEQIDNO:38), L37 (SEQIDNO:46) and L25 (SEQIDNO:36) found three times. From these results we conclude, that these proteins are encoded by multiple genes or that these genes are highly expressed. Therefore isolation of these promoter sequences are new and promising target sequences to isolate high level expression signals from *Phaffia rhodozyma*. Furthermore, a cDNA clone was isolated which showed 50% homology to an abundant glucose-repressible gene from Neurospora crassa (Curr. genet. 14: 545–551 (1988)). The nucleotide sequence and the deduced amino acid sequence is shown in SEQIDNO:26. One of the advantages of such a promoter sequence is that it can be used to separated growth (biomass accumulation) and gene expression (product accumulation) in large scale Phaffia fermentation.

For the isolation of the promoter sequences of interest (as outlined above) a fragment from the corresponding cDNA clone can be used as probe to screen the genomic library of *Phaffia rhodozyma* following the approach as described for the GAPDH-gene promoter (Example 3, supra). Based on the determined nucleotide sequence of the promoter, specific oligonucleotides can be designed to construct a transcription fusion between the promoter and any gene of interest by the fusion PCR technique, following the procedure as outlined in Example 5 (supra).

EXAMPLE 19

Isolation of Carotenogenic Genes by Heterologous Hybridization

For the identification and isolation of corresponding carotenoid biosynthetic pathway genes from organisms related to *Phaffia rhodozyma* heterologous hybridization experiments were carried out under conditions of moderate stringency. In these experiments chromosomal DNA from two carotenogenic fungi (*Neurospora crassa* and *Blakeslea trispora*) and the yeasts *S. cerevisiae* and three yeast and fungal species from the genus Cystofylobasidium was used. These three carotenogenic yeasts are, based on phylogenetic studies, the ones most related to *P. rhodozyma*.

Chromosomal DNA from the yeast species *Cystofylobasidium infirmo-miniatum* (CBS 323), *C. bisporidii* (CBS 6346) and *C. capitatum* (CBS 6358) was isolated according the method as developed for *Phaffia rhodozyma*, described in example 3 of European patent application 0 590 707 A1; the relevant portions of which herein incorporated by reference. Isolation of chromosomal DNA from the fungi *Neurospora crassa* and *Blakeslea trispora* was essentially carried as described by Kolar et al. (Gene, 62: 127–134), the relevant parts of which are herein incorporated by reference.

Chromosomal DNA (5 µg) of *C. infirmo-miniatum, C. bisporidii, C. capitatum, S. cerevisiae, P. rhodozyma, N. crassa* and *B. trispora* was digested using EcoRI. The DNA fragments were separated on a 0.8% agarose gel, blotted and hybridized using the following conditions.

Hybridization was cared out at two temperatures (50° C. and 55° C.) using four different $^{32}$P labelled Phaffia probes. The probes were made using random primed hexanucleotide labellings reactions using the XhoI-XbaI fragment(s) from the cDNA clones pPRcrtE, pPRcrtB, pPRcrtI and pPRidi as template. Hybridization was carried out o/n (16 h) at the indicated temperatures. After hybridization the filters were washed 2 times for 30 min. at the hybridization temperatures using a solution of 3*SSC; 0.1% SDS; 0.05% sodiumpyrophosphate. Films were developed after exposure of the filters to X-ray films in a cassette at –80° C. for 20 h.

Using the cDNA clone of crtE of *P. rhodozyma* faint signals were obtained for *C. infirmo-miniatum, C. capitatum*. Using the cDNA clone of crtB of *P. rhodozyma* strong signals were obtained to the high molecular weight portion of DNA from *C. infirmo-miniatum* and *C. capitatum*. Furthermore a strong signal was obtained in the lane loaded with digested chromosomal DNA from *B. trispora*. Only a faint signal was obtained for *C. capitatum* at 50° C. using the cDNA clone of crtI of *P. rhodozyma*. Using the cDNA clone of idi of *P. rhodozyma* faint signals were obtained with chromosomal DNA from *C. infirmo-miniatum, C. bisporidii* and *C. capitatum* at both temperatures. A strong signal was obtained in the lane loaded with digested chromosomal DNA from *B. trispora*.

We conclude, that carotenoid biosynthesis cDNAs or genes, or idi cDNAs or genes, can be isolated from other organisms, in particular from other yeast species by cross-hybridisation with the cDNA fragment coding for *P. Rhodozyma* carotenoid biosynthesis enzymes, or isopentenyl pyrophosphate isomerase coding sequences respectively, using moderately stringent hybridisation and washing conditions (50° C. to 55° C., 3×SSC).

Deposited Microorganisms

*E. coli* containing pGB-Ph9 has been deposited at the Centraal Bureau voor Schimmelcultures, Oosterstraat 1, Baarn, The Netherlands, on Jun. 23, 1993, under accession number CBS 359.3. The following strains have been deposited under the Budapest Treaty at the Centraal Bureau voor Schimmelcultures, Oosterstraat 1, Baarn, The Netherlands, on Feb. 26, 1996:

| ID nr. | Organism | relevant feature | Deposit number |
|--------|----------|------------------|----------------|
| DS31855 | E. coli | crtY of P. rhodozyma | CBS 232.96 |
| DS31856 | E. coli | crtI of P. rhodozyma | CBS 233.96 |
| DS31857 | E. coli | crtE of P. rhodozyma | CBS 234.96 |
| DS31858 | E. coli | crtB of P. rhodozyma | CBS 235.96 |

What is claimed is:

1. Recombinant DNA comprising a transcription promoter and a downstream sequence to be expressed, in operable inkage therewith, wherein the transcription promoter comprises a region found upstream of the open readings frame of a highly expressed Phaffia gene is capable of making *Phaffia rhodozyma* transformed with a DNA construct having said promoter linked up front of the G418 resistance marker resistant to G-418 in concentrations exceeding 200 μg per liter culture medium, wherein said highly expressed Phaffia gene is a glyceraldehyde-3-phosphate dehydrogenase gene or a ribosomal protein encoding gene.

2. A microorganism harboring a recombinant DNA according to claim 1.

3. A microorganism according to claim 2, which is *Phaffia rhodozyma*.

4. A microorganism according to claim 3, having the recombinant DNA integrated into its genome in an amount of 50 copies or more.

5. Recombinant DNA of claim 1 wherein said open reading frame encodes one of the amino acid sequences depicted in any one of SEQ ID NOs: 24 to 50.

6. A recombinant DNA according to claim 1 wherein said downstream sequence to be expressed is heterologous with respect to the transcription promoter sequence.

7. A recombinant DNA according to claim 1, wherein the downstream sequence encodes a polypeptide responsible for reduced sensitivity against a selective agent.

8. A recombinant DNA according to claim 7, wherein said selective agent is G418.

9. A recombinant DNA according to claim 1, wherein the said downstream sequence to be expressed encodes an enzyme involved in the carotenoid biosynthesis pathway.

10. A recombinant DNA according to claim 9, wherein said downstream sequence to be expressed encodes an enzyme having an activity selected from the group consisting of isopentenyl pyrophosphate isomerase, geranylgeranyl pyrophosphate synthase, phytoene synthase, phytoene desaturase, and lycopene cyclase.

11. A recombinant DNA according to claim 10, wherein said downstream sequence to be expressed encodes an enzyme having an amino acid sequence selected from the group consisting of SEQ ID NO: 13, SEQ ID NO: 15, SEQ ID NO: 17, SEQ ID NO: 19, SEQ ID NO: 21 and SEQ ID NO: 23.

12. A recombinant DNA according to claim 1 wherein said recombinant DNA comprises further a transcription terminator downstream from the said DNA sequence to be expressed, in operable linkage therewith.

13. A recombinant DNA according to claim 12, wherein the terminator is a GAPDH-encoding gene terminator fragment.

14. A recombinant DNA according to claim 1 wherein the recombinant DNA is in the form of a vector capable of replication and/or integration in a host organism.

15. A recombinant DNA according to claim 14, further comprising DNA transcribed into Phaffia ribosomal RNA.

16. A recombinant DNA according to claim 15, which is linearized by cleaving inside the DNA transcribed into Phaffia ribosomal RNA.

17. A method for obtaining a transformed Phaffia strain, comprising the steps of
    (a) contacting cells or protoplasts of a Phaffia strain with the recombinant DNA of claim 1 under conditions conducive to uptake thereof, and
    (b) identifying *Phaffia rhodozyma* cells or protoplasts having obtained the said recombinant DNA in expressible form.

18. A method according to claim 17, comprising the additional step of providing an electropulse after contacting of Phaffia cells or protoplasts with the said recombinant DNA.

19. A transformed Phaffia strain obtainable by a method according to claim 17 wherein said strain, upon cultivation, expresses expression of the said downstream sequence.

20. A transformed Phaffia strain according to claim 19, wherein the said downstream sequence codes for a pharmaceutical protein.

21. A method for producing a pharmaceutical protein which method comprises culturing a transformed Phaffia strain according to claim 20 under conditions conducive to the production of the said protein.

22. A transformed Phaffia strain according to claim 19 wherein the said Phaffia strain contains at least 10 copies of the said recombinant DNA integrated into its genome.

23. An isolated DNA fragment comprising a Phaffia GAPDH-gene, or a functional fragment thereof including a promoter which is capable of making *Phaffia rhodozyma* transformed with a DNA construct having said promoter linked up front of the G418 resistance marker resistant to G-418 in concentrations exceeding 200 μg per liter culture medium.

24. A method to prepare a recombinant DNA construct which comprises ligating a functional fragment according to claim 23 into said construct.

25. The method according to claim 24, wherein said fragment is a regulatory region normally located upstream or downstream of the open reading frame coding for GAPDH in *Phaffia rhodozyma*.

26. A transformed *Phaffia rhodozyma* strain which overexpresses a nucleotide sequence encoding an enzyme involved in the carotenoid biosynthesis pathway, wherein the nucleotide sequence is operably linked to a promoter which is capable of making *Phaffia rhodozyma* transformed with a DNA construct having said promoter linked up front of the G418 resistance marker resistant to G-418 in concentrations exceeding 200 μg per liter culture medium.

27. A transformed *Phaffia rhodozyma* strain according to claim 26, which produces inreased amounts of astaxanthin relative to its untransformed ancestor.

28. An isolated DNA comprising a nucleotide sequence encoding an enzyme that has an activity in the carotenoid biosynthetic pathway operably linked to a promoter which is capable of making *Phaffia rhodozyma* transformed with a DNA construct having said promoter linked up front of the G418 resistance marker resistant to G-418 in concentrations exceeding 200 μg per liter culture medium.

29. An isolated DNA according to claim 28, wherein said activity is selected from isopentenyl pyrophosphate isomerase activity, geranylgeranyl pyrophosphate synthase activity, phytoene synthase activity, phytoene desaturase activity and lycopene cyclase activity.

30. The isolated DNA of claim 28 wherein said enzyme has an amino acid sequence selected from the group consisting of SEQ ID NO: 13, SEQ ID NO: 15, SEQ ID NO 17, SEQ ID NO: 19, SEQ ID NO: 21 and SEQ ID NO: 23.

31. The isolated DNA of claim 28, wherein the carotenoid biosynthetic pathway is one from *Phaffia rhodozyma*.

32. Recombinant DNA comprising the encoding nucleotide sequence according to claim 28.

33. Recombinant DNA according to claim 32 being in the form of a vector.

34. Recombinant DNA according to claim 32, wherein said encoding nucleotide sequence is operably linked to a transcription promoter which is expressed in a suitable host, said isolated DNA sequence optionally being linked to a transcription terminator functional in the said host.

35. Recombinant DNA according to claim 34, wherein said host is a Phaffia strain.

36. Recombinant DNA according to claim 34 wherein the transcription promoter is from a glycolytic pathway gene present in Phaffia.

37. Recombinant DNA according to claim 36, wherein said glycolytic pathway gene is a gene coding for Glyceraldehyde-3-Phosphate Dehydrogenase.

38. Recombinant DNA according to claim 34 wherein the transcription promoter is from a ribosomal protein encoding gene.

39. Recombinant DNA according to claim 34 wherein the transcription promoter comprises a region found upstream of the open reading frame encoding a protein as represented by one of the amino acid sequences depicted in any one of SEQ ID NOs: 24 to 50.

40. Recombinant DNA according to claim 34 wherein said recombinant DNA comprises further a transcription terminator downstream from the said encoding nucleotide sequence to be expressed, in operable linkage therewith, which terminator is a Phaffia transcription terminator.

41. A host modified to contain the recombinant DNA according to claim 32.

42. A host according to claim 41, which is a Phaffia strain.

43. A method for producing an enzyme involved in the carotenoid biosynthesis pathway, which method comprises culturing a host according to claim 41 under conditions conducive to the production of said enzyme.

44. A method for producing a carotenoid which method comprises cultivating a host according to claim 41 under conditions conducive to the production of a carotenoid.

45. A method according to claim 44, wherein the carotenoid is astaxanthin.

* * * * *

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (C) INDIVIDUAL ISOLATE: AB3005

(xi) SEQUENCE DESCRIPTION: SEQ ID NO:1:

CGGGATCCAA RCTNACNGGN ATGGC                                              25

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (C) INDIVIDUAL ISOLATE: AB3006

(ix) FEATURE:
      (A) NAME/KEY: misc_feature
      (B) LOCATION: one-of(12)
      (D) OTHER INFORMATION: /note= "N at position 12 is
         inosine"

(xi) SEQUENCE DESCRIPTION: SEQ ID NO:2:

CGGGATCCRT ANCCVYAYTC RTTRTCRTAC CA                                      32

(2) INFORMATION FOR SEQ ID NO:3:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (C) INDIVIDUAL ISOLATE: AB4206

(xi) SEQUENCE DESCRIPTION: SEQ ID NO:3:

GCGTGACTTC TGGCCAGCCA CGATAGC                                            27

(2) INFORMATION FOR SEQ ID NO:4:

(i) SEQUENCE CHARACTERISTICS:
      (A) LENGTH: 32 base pairs
      (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB5126

(xi) SEQUENCE DESCRIPTION: SEQ ID NO:4:

TTCAATCCAC ATGATGGTAA GAGTGTTAGA GA                                              32

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB5127

(xi) SEQUENCE DESCRIPTION: SEQ ID NO:5:

CTTACCATCA TGTGGATTGA ACAAGATGGA T                                               31

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB5177

(xi) SEQUENCE DESCRIPTION: SEQ ID NO:6:

CCCAAGCTTC TCGAGGTACC TGGTGGGTGC ATGTATGTAC                                      40

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB5137

(xi) SEQUENCE DESCRIPTION: SEQ ID NO:7:

CCAAGGCCTA AAACGGATCC CTCCAAACCC                                                 30
```

```
(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: AB5138

(xi) SEQUENCE DESCRIPTION: SEQ ID NO:8:

GCCAAGCTTC TCGAGCTTGA TCAGATAAAG ATAGAGAT                              38

(2) INFORMATION FOR SEQ ID NO:9:

(i) SEQUENCE CHARACTERISTICS:
        (A) LENGTH: 2309 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phaffia rhodozyma
        (B) STRAIN: CBS 6938

(ix) FEATURE:
        (A) NAME/KEY: exon
        (B) LOCATION: 300..330

(ix) FEATURE:
        (A) NAME/KEY: intron
        (B) LOCATION: 331..530

(ix) FEATURE:
        (A) NAME/KEY: exon
        (B) LOCATION: 531..578

(ix) FEATURE:
        (A) NAME/KEY: intron
        (B) LOCATION: 579..668

(ix) FEATURE:
        (A) NAME/KEY: exon
        (B) LOCATION: 669..690

(ix) FEATURE:
        (A) NAME/KEY: intron
        (B) LOCATION: 691..767

(ix) FEATURE:
        (A) NAME/KEY: exon
        (B) LOCATION: 768..805

(ix) FEATURE:
        (A) NAME/KEY: intron
        (B) LOCATION: 806..905

(ix) FEATURE:
        (A) NAME/KEY: exon
        (B) LOCATION: 906..923

(ix) FEATURE:
        (A) NAME/KEY: intron
        (B) LOCATION: 924..1030
```

-continued (ix) FEATURE:
  (A) NAME/KEY: exon
  (B) LOCATION: 1031..1378

(ix) FEATURE:
  (A) NAME/KEY: intron
  (B) LOCATION: 1379..1508

(ix) FEATURE:
  (A) NAME/KEY: exon
  (B) LOCATION: 1509..2020

(ix) FEATURE:
  (A) NAME/KEY: CDS
  (B) LOCATION: join(300..330, 531..578, 669..690, 768..805, 906
      ..923, 1031..1378, 1509..2020)

(xi) SEQUENCE DESCRIPTION: SEQ ID NO:9:

```
GCTATGAGCA AGCACAACTG GGCACCGAAC GAGAACAGTA ACTGTCGGTA TCTTCCCACC      60

GACACGAGGC GTCTCCCGGC GGCAACCGCC GGTGCCCCCC TCCGCTTACG TCAGCCACCC     120

AGTTTTCTTC CATCTCTTTC TCTCTCCTTC CAAAAGTCTT TCAGTTTTAA ACGGCCCCCA     180

AAAAAAGAAG AGGCGACTTT TTCTTTCCTT CTCCCCATCA TCCACAAAGA TCTCTCTTCT     240

TCAACAACAA CTACTACTAC TACCACTACC ACCACTACTT CTCTAACACT CTTACCATC      299

ATG GCT GTC AAG GTT GGA ATC AAC GGT TTC  G GTATGTGTTT GTTTTCTCT       350
Met Ala Val Lys Val Gly Ile Asn Gly Phe
 1               5                  10

TGAGCTCCCC CATCGGTTCT TTCGCTTGTC CATGTTTCTT TTTCCTTTCC TTTCCTTTTC     410

TTTTTTCTCC CCACTGCCTT TTTTTTTTCT ATTCTTTTTT TTTTCCTTTC CTCTCGCCTT     470

CATGCATCGC ACTAACACCA TCTCATCTCA TCTCACTCTG CCTCGTCTTA CCTCCTACAG     530

GA CGA ATC GGA CGA ATC GTC CTT CGA AAC GCT ATC ATC CAC GGT GAT  A    578
Gly Arg Ile Gly Arg Ile Val Leu Arg Asn Ala Ile Ile His Gly Asp
       15                  20                  25

GTCAGTATTT TTTTAATTTC TTTTTTTCCC CATCAATTTC CCTCTGCTCC TTTACTCATC     638

TCTTTCCATC TCTCTCCCAC TCTCCTACAG  TC GAT GTC GTC GCC ATC AAC  GA      690
                                  Ile Asp Val Val Ala Ile Asn  Asp
                                                   30

GTGCGTCTAG ATCGACCATC TCGTCGTCCG CCCAAACACC GTCTGACACC ATCCTGTTAA     750

CTTTTCTCTC CTCCAAG C CCT TTC ATC GAT CTT GAG TAC ATG GTC TAC ATG      801
                   Pro Phe Ile Asp Leu Glu Tyr Met Val Tyr Met
                    35                  40                  45

TTC  A GTAAGTCTCC CTCCCCCTCA AAAAGCCGAA ACAAAGCCGA ACAGAACCCG         855
Phe

ATCTAACCAT TCGTTCTTCT TCCCTTTCCT CTTCCGTCTC TCCCTCACAG  AG TAC         910
                                                        Lys Tyr
GAC TCC ACC CAC  G GTTCGTCCAT CCCTCTCTCT GTCCCGAACA TCTCCGACCG         963
Asp Ser Thr His
 50

GGCCTTTTCC ATCTCCTGAT CCGTTCGCGT ACTAACCCAT ACCGTACCCT TCGTCCCATC    1023

CCTTCAG  GT GTC TTC AAG GGA TCC GTC GAG ATC AAG GAC GGC AAG CTC      1071
        Gly Val Phe Lys Gly Ser Val Glu Ile Lys Asp Gly Lys Leu
             55                  60                  65

GTG ATC GAG GGC AAG CCC ATC GTC GTC TAC GGT GAG CGA GAC CCC GCC      1119
Val Ile Glu Gly Lys Pro Ile Val Val Tyr Gly Glu Arg Asp Pro Ala
 70                  75                  80
```

```
AAC ATC CAG TGG GGA GCT GCC GGT GCC GAC TAC GTC GTC GAG TCC ACC      1167
Asn Ile Gln Trp Gly Ala Ala Gly Ala Asp Tyr Val Val Glu Ser Thr
        85                  90                  95

GGT GTC TTC ACC ACC CAG GAG AAG GCC GAG CTC CAC CTC AAG GGA GGA      1215
Gly Val Phe Thr Thr Gln Glu Lys Ala Glu Leu His Leu Lys Gly Gly
100                 105                 110

GCC AAG AAG GTC GTC ATC TCT GCC CCT TCG GCC GAT GCC CCC ATG TTC      1263
Ala Lys Lys Val Val Ile Ser Ala Pro Ser Ala Asp Ala Pro Met Phe
115                 120                 125                 130

GTC TGC GGT GTT AAC CTC GAC AAG TAC GAC CCC AAG TAC ACC GTC GTC      1311
Val Cys Gly Val Asn Leu Asp Lys Tyr Asp Pro Lys Tyr Thr Val Val
            135                 140                 145

TCC AAC GCT TCG TGC ACC ACC AAC TGC TTG GCT CCC CTC GGC AAG GTC      1359
Ser Asn Ala Ser Cys Thr Thr Asn Cys Leu Ala Pro Leu Gly Lys Val
                150                 155                 160

ATC CAC GAC AAC TAC ACC  A GTCAGTCCTT TNCTTTGGAC TTGTCTGGCC          1408
Ile His Asp Asn Tyr Thr
            165

TTTTCTTTGT TGGTTCTTTT CCTTTTGTCA AACCATCCAT ACTCACCCTG TTTTTCACCT    1468

TCTTTTTCTT CATTCACGTA TTCCCCCTCC CGTCCACCAG  TT GTC GAG GGT CTC     1522
                                                Ile Val Glu Gly Leu
                                                            170

ATG ACC ACC GTC CAC GCC ACC ACC GCC ACC CAG AAG ACC GTC GAC GGT      1570
Met Thr Thr Val His Ala Thr Thr Ala Thr Gln Lys Thr Val Asp Gly
        175                 180                 185

CCT TCC AAC AAG GAC TGG CGA GGA GGT CGA GGA GCT GGT GCC AAC ATC      1618
Pro Ser Asn Lys Asp Trp Arg Gly Gly Arg Gly Ala Gly Ala Asn Ile
190                 195                 200                 205

ATT CCC TCC TCC ACC GGA GCC GCC AAG GCC GTC GGT AAG GTT ATC CCC      1666
Ile Pro Ser Ser Thr Gly Ala Ala Lys Ala Val Gly Lys Val Ile Pro
            210                 215                 220

TCC CTC AAC GGA AAG CTC ACC GGA ATG GCC TTC CGA GTG CCC ACC CCC      1714
Ser Leu Asn Gly Lys Leu Thr Gly Met Ala Phe Arg Val Pro Thr Pro
                225                 230                 235

GAT GTC TCC GTC GTC GAT CTT GTC GTC CGA ATC GAG AAG GGC GCC TCT      1762
Asp Val Ser Val Val Asp Leu Val Val Arg Ile Glu Lys Gly Ala Ser
                    240                 245                 250

TAC GAG GAG ATC AAG GAG ACC ATC AAG AAG GCC TCC CAG ACC CCT GAG      1810
Tyr Glu Glu Ile Lys Glu Thr Ile Lys Lys Ala Ser Gln Thr Pro Glu
        255                 260                 265

CTC AAG GGT ATC CTG AAC TAC ACC GAC GAC CAG GTC GTC TCC ACC GAT      1858
Leu Lys Gly Ile Leu Asn Tyr Thr Asp Asp Gln Val Val Ser Thr Asp
270                 275                 280                 285

TTC ACC GGT GAC TCT GCC TCC TCC ACC TTC GAC GCC CAG GGC GGT ATC      1906
Phe Thr Gly Asp Ser Ala Ser Ser Thr Phe Asp Ala Gln Gly Gly Ile
            290                 295                 300

TCC CTT AAC GGA AAC TTC GTC AAG CTT GTC TCC TGG TAC GAC AAC GAG      1954
Ser Leu Asn Gly Asn Phe Val Lys Leu Val Ser Trp Tyr Asp Asn Glu
                305                 310                 315

TGG GGA TAC TCT GCC CGA GTC TGC GAC CTT GTT TCT TAC ATC GCC GCC      2002
Trp Gly Tyr Ser Ala Arg Val Cys Asp Leu Val Ser Tyr Ile Ala Ala
                    320                 325                 330

CAG GAC GCC AAG GCC TAAACGGTTC TCTCCAAACC CTCTCCCCTT TTGCCCTGCC      2057
Gln Asp Ala Lys Ala
            335

CATTGAATTG ATTCCCTAAA TAGAATATCC CACTTTCTTT TATGCTCTAC CTATGATCAG    2117

TTTATCTGTC TTTTTCTTTG TGCGTGTCGG TTGTGCGACT GTACCCACCT CTTGAGGGAC    2177
```

-continued

```
AAGGCAAGAA GTGAGCAAGA TATGAACAAG AACAACAAAG AAAAAGAGAC AAAGAAAAAA      2237

AAAAGGAAAG AGAAAACAAT CCCCCCCCCC CCCCAAAAAA AAATCTCTAT CTTTATCTGA      2297

TCAAGAGATT AT                                                          2309
```

(2) INFORMATION FOR SEQ ID NO:10:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Val Lys Val Gly Ile Asn Gly Phe Gly Arg Ile Gly Arg Ile
 1               5                  10                  15

Val Leu Arg Asn Ala Ile Ile His Gly Asp Ile Asp Val Val Ala Ile
                20                  25                  30

Asn Asp Pro Phe Ile Asp Leu Glu Tyr Met Val Tyr Met Phe Lys Tyr
            35                  40                  45

Asp Ser Thr His Gly Val Phe Lys Gly Ser Val Glu Ile Lys Asp Gly
        50                  55                  60

Lys Leu Val Ile Glu Gly Lys Pro Ile Val Val Tyr Gly Glu Arg Asp
65                  70                  75                  80

Pro Ala Asn Ile Gln Trp Gly Ala Ala Gly Ala Asp Tyr Val Val Glu
                85                  90                  95

Ser Thr Gly Val Phe Thr Thr Gln Glu Lys Ala Glu Leu His Leu Lys
            100                 105                 110

Gly Gly Ala Lys Lys Val Val Ile Ser Ala Pro Ser Ala Asp Ala Pro
        115                 120                 125

Met Phe Val Cys Gly Val Asn Leu Asp Lys Tyr Asp Pro Lys Tyr Thr
    130                 135                 140

Val Val Ser Asn Ala Ser Cys Thr Thr Asn Cys Leu Ala Pro Leu Gly
145                 150                 155                 160

Lys Val Ile His Asp Asn Tyr Thr Ile Val Glu Gly Leu Met Thr Thr
                165                 170                 175

Val His Ala Thr Thr Ala Thr Gln Lys Thr Val Asp Gly Pro Ser Asn
            180                 185                 190

Lys Asp Trp Arg Gly Gly Arg Gly Ala Gly Ala Asn Ile Ile Pro Ser
        195                 200                 205

Ser Thr Gly Ala Ala Lys Ala Val Gly Lys Val Ile Pro Ser Leu Asn
    210                 215                 220

Gly Lys Leu Thr Gly Met Ala Phe Arg Val Pro Thr Pro Asp Val Ser
225                 230                 235                 240

Val Val Asp Leu Val Val Arg Ile Glu Lys Gly Ala Ser Tyr Glu Glu
                245                 250                 255

Ile Lys Glu Thr Ile Lys Lys Ala Ser Gln Thr Pro Glu Leu Lys Gly
            260                 265                 270

Ile Leu Asn Tyr Thr Asp Asp Gln Val Val Ser Thr Asp Phe Thr Gly
        275                 280                 285

Asp Ser Ala Ser Ser Thr Phe Asp Ala Gln Gly Ile Ser Leu Asn
    290                 295                 300

Gly Asn Phe Val Lys Leu Val Ser Trp Tyr Asp Asn Glu Trp Gly Tyr
305                 310                 315                 320
```

```
Ser Ala Arg Val Cys Asp Leu Val Ser Tyr Ile Ala Ala Gln Asp Ala
            325                 330                 335

Lys Ala (2) INFORMATION FOR SEQ ID NO: 11:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: promoter
        (B) LOCATION:1..385

(ix) FEATURE:
        (A) NAME/KEY: TATA_signal
        (B) LOCATION:249..263
        (D) OTHER INFORMATION:/label= putative (ix) FEATURE:
        (A) NAME/KEY: misc_signal
        (B) LOCATION:287..302
        (D) OTHER INFORMATION:/function= "cap-signal"
            /label= putative (ix) FEATURE:
        (A) NAME/KEY: misc_RNA
        (B) LOCATION:386..388
        (D) OTHER INFORMATION:/function= "start of CDS"

(ix) FEATURE:
        (A) NAME/KEY: misc_feature
        (B) LOCATION:85
        (D) OTHER INFORMATION:/note= "uncertain"

(xi) SEQUENCE DESCRIPTION: SEQ ID NO: 11:

TGGTGGGTGC ATGTATGTAC GTGAGTGAGT GCGGGGGAAA GGCGAGTACG TGTGTGTACG      60

CGCAAGGAAG AACAACGAAG CGCANGCTAT GAGCAAGCAC AACTGGGCAC CGAACGAGAA     120

CAGTAACTGT CGGTATCTTC CCACCGACAC GAGGCGTCTC CCGGCGGCAA CCGCCGGTGC     180

CCCCCTCCGC TTACGTCAGC CACCCAGTTT TCTTCCATCT CTTTCTCTCT CCTTCCAAAA     240

GTCTTTCAGT TTTAAACGGC CCCCAAAAAA AGAAGAGGCG ACTTTTTCTT TCCTTCTCTC     300

CCATCATCCA CAAAGATCTC TCTTCTTCAA CAACAACTAC TACTACTACC ACTACCACCA     360

CTACTTCTCT AACACTCTTA CCATCATG                                       388

(2) INFORMATION FOR SEQ ID NO:12:

(i) SEQUENCE CHARACTERISTICS:
        (A) LENGTH: 2546 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO
```

(vi) ORIGINAL SOURCE:
    (A) ORGANISM: Phaffia rhodozyma (ix) FEATURE:
    (A) NAME/KEY: CDS
    (B) LOCATION: 225..2246
    (D) OTHER INFORMATION: /product= "PRcrtB"

(xi) SEQUENCE DESCRIPTION: SEQ ID NO:12:

| | | |
|---|---|---|
| TCTAGAACTA GTGGATCCCC CGGGCTGCAG GAATTCGGCA CGAGCGGAAA CAAGAAGTGG | 60 |
| ACACAGAGAG ATCTTTGCTG AAGAGTTGTA TTCCAGAAAG GGAAAACAAA GGAAAGAAGC | 120 |
| GCCGAAGCAC ATCACCAACT TCAGCAAGCC GGTCCAGCCC GATCTCGGAT AGACATCATC | 180 |
| TTACCCAACT CGTATCATCC CCAACAGATA GAGTTTTTGT CGCA ATG ACG GCT CTC | 236 |

```
                                              Met Thr Ala Leu
                                                1
GCA TAT TAC CAG ATC CAT CTG ATC TAT ACT CTC CCA ATT CTT GGT CTT      284
Ala Tyr Tyr Gln Ile His Leu Ile Tyr Thr Leu Pro Ile Leu Gly Leu
  5              10                  15                  20

CTC GGC CTG CTC ACT TCC CCG ATT TTG ACA AAA TTT GAC ATC TAC AAA      332
Leu Gly Leu Leu Thr Ser Pro Ile Leu Thr Lys Phe Asp Ile Tyr Lys
             25                  30                  35

ATA TCG ATC CTC GTA TTT ATT GCG TTT AGT GCA ACC ACA CCA TGG GAC      380
Ile Ser Ile Leu Val Phe Ile Ala Phe Ser Ala Thr Thr Pro Trp Asp
         40                  45                  50

TCA TGG ATC ATC AGA AAT GGC GCA TGG ACA TAT CCA TCA GCG GAG AGT      428
Ser Trp Ile Ile Arg Asn Gly Ala Trp Thr Tyr Pro Ser Ala Glu Ser
     55                  60                  65

GGC CAA GGC GTG TTT GGA ACG TTT CTA GAT GTT CCA TAT GAA GAG TAC      476
Gly Gln Gly Val Phe Gly Thr Phe Leu Asp Val Pro Tyr Glu Glu Tyr
 70                  75                  80

GCT TTC TTT GTC ATT CAA ACC GTA ATC ACC GGC TTG GTC TAC GTC TTG      524
Ala Phe Phe Val Ile Gln Thr Val Ile Thr Gly Leu Val Tyr Val Leu
 85                  90                  95                 100

GCA ACT AGG CAC CTT CTC CCA TCT CTC GCG CTT CCC AAG ACT AGA TCG      572
Ala Thr Arg His Leu Leu Pro Ser Leu Ala Leu Pro Lys Thr Arg Ser
                105                 110                 115

TCC GCC CTT TCT CTC GCG CTC AAG GCG CTC ATC CCT CTG CCC ATT ATC      620
Ser Ala Leu Ser Leu Ala Leu Lys Ala Leu Ile Pro Leu Pro Ile Ile
            120                 125                 130

TAC CTA TTT ACC GCT CAC CCC AGC CCA TCG CCC GAC CCG CTC GTG ACA      668
Tyr Leu Phe Thr Ala His Pro Ser Pro Ser Pro Asp Pro Leu Val Thr
        135                 140                 145

GAT CAC TAC TTC TAC ATG CGG GCA CTC TCC TTA CTC ATC ACC CCA CCT      716
Asp His Tyr Phe Tyr Met Arg Ala Leu Ser Leu Leu Ile Thr Pro Pro
    150                 155                 160

ACC ATG CTC TTG GCA GCA TTA TCA GGC GAA TAT GCT TTC GAT TGG AAA      764
Thr Met Leu Leu Ala Ala Leu Ser Gly Glu Tyr Ala Phe Asp Trp Lys
165                 170                 175                 180

AGT GGC CGA GCA AAG TCA ACT ATT GCA GCA ATC ATG ATC CCG ACG GTG      812
Ser Gly Arg Ala Lys Ser Thr Ile Ala Ala Ile Met Ile Pro Thr Val
                185                 190                 195

TAT CTG ATT TGG GTA GAT TAT GTT GCT GTC GGT CAA GAC TCT TGG TCG      860
Tyr Leu Ile Trp Val Asp Tyr Val Ala Val Gly Gln Asp Ser Trp Ser
            200                 205                 210

ATC AAC GAT GAG AAG ATT GTA GGG TGG AGG CTT GGA GGT GTA CTA CCC      908
Ile Asn Asp Glu Lys Ile Val Gly Trp Arg Leu Gly Gly Val Leu Pro
        215                 220                 225
```

```
ATT GAG GAA GCT ATG TTC TTC TTA CTG ACG AAT CTA ATG ATT GTT CTG      956
Ile Glu Glu Ala Met Phe Phe Leu Leu Thr Asn Leu Met Ile Val Leu
    230                 235                 240

GGT CTG TCT GCC TGC GAT CAT ACT CAG GCC CTA TAC CTG CTA CAC GGT     1004
Gly Leu Ser Ala Cys Asp His Thr Gln Ala Leu Tyr Leu Leu His Gly
245                 250                 255                 260

CGA ACT ATT TAT GGC AAC AAA AAG ATG CCA TCT TCA TTT CCC CTC ATT     1052
Arg Thr Ile Tyr Gly Asn Lys Lys Met Pro Ser Ser Phe Pro Leu Ile
                265                 270                 275

ACA CCG CCT GTG CTC TCC CTG TTT TTT AGC AGC CGA CCA TAC TCT TCT     1100
Thr Pro Pro Val Leu Ser Leu Phe Phe Ser Ser Arg Pro Tyr Ser Ser
            280                 285                 290

CAG CCA AAA CGT GAC TTG GAA CTG GCA GTC AAG TTG TTG GAG AAA AAG     1148
Gln Pro Lys Arg Asp Leu Glu Leu Ala Val Lys Leu Leu Glu Lys Lys
        295                 300                 305

AGC CGG AGC TTT TTT GTT GCC TCG GCT GGA TTT CCT AGC GAA GTT AGG     1196
Ser Arg Ser Phe Phe Val Ala Ser Ala Gly Phe Pro Ser Glu Val Arg
    310                 315                 320

GAG AGG CTG GTT GGA CTA TAC GCA TTC TGC CGG GTG ACT GAT GAT CTT     1244
Glu Arg Leu Val Gly Leu Tyr Ala Phe Cys Arg Val Thr Asp Asp Leu
325                 330                 335                 340

ATC GAC TCT CCT GAA GTA TCT TCC AAC CCG CAT GCC ACA ATT GAC ATG     1292
Ile Asp Ser Pro Glu Val Ser Ser Asn Pro His Ala Thr Ile Asp Met
                345                 350                 355

GTC TCC GAT TTT CTT ACC CTA CTA TTT GGG CCC CCG CTA CAC CCT TCG     1340
Val Ser Asp Phe Leu Thr Leu Leu Phe Gly Pro Pro Leu His Pro Ser
            360                 365                 370

CAA CCT GAC AAG ATC CTT TCT TCG CCT TTA CTT CCT CCT TCG CAC CCT     1388
Gln Pro Asp Lys Ile Leu Ser Ser Pro Leu Leu Pro Pro Ser His Pro
        375                 380                 385

TCC CGA CCC ACG GGA ATG TAT CCC CTC CCG CCT CCT CCT TCG CTC TCG     1436
Ser Arg Pro Thr Gly Met Tyr Pro Leu Pro Pro Pro Pro Ser Leu Ser
    390                 395                 400

CCT GCC GAG CTC GTT CAA TTC CTT ACC GAA AGG GTT CCC GTT CAA TAC     1484
Pro Ala Glu Leu Val Gln Phe Leu Thr Glu Arg Val Pro Val Gln Tyr
405                 410                 415                 420

CAT TTC GCC TTC AGG TTG CTC GCT AAG TTG CAA GGG CTG ATC CCT CGA     1532
His Phe Ala Phe Arg Leu Leu Ala Lys Leu Gln Gly Leu Ile Pro Arg
                425                 430                 435

TAC CCA CTC GAC GAA CTC CTT AGA GGA TAC ACC ACT GAT CTT ATC TTT     1580
Tyr Pro Leu Asp Glu Leu Leu Arg Gly Tyr Thr Thr Asp Leu Ile Phe
            440                 445                 450

CCC TTA TCG ACA GAG GCA GTC CAG GCT CGG AAG ACG CCT ATC GAG ACC     1628
Pro Leu Ser Thr Glu Ala Val Gln Ala Arg Lys Thr Pro Ile Glu Thr
        455                 460                 465

ACA GCT GAC TTG CTG GAC TAT GGT CTA TGT GTA GCA GGC TCA GTC GCC     1676
Thr Ala Asp Leu Leu Asp Tyr Gly Leu Cys Val Ala Gly Ser Val Ala
    470                 475                 480

GAG CTA TTG GTC TAT GTC TCT TGG GCA AGT GCA CCA AGT CAG GTC CCT     1724
Glu Leu Leu Val Tyr Val Ser Trp Ala Ser Ala Pro Ser Gln Val Pro
485                 490                 495                 500

GCC ACC ATA GAA GAA AGA GAA GCT GTG TTA GTG GCA AGC CGA GAG ATG     1772
Ala Thr Ile Glu Glu Arg Glu Ala Val Leu Val Ala Ser Arg Glu Met
                505                 510                 515

GGA ACT GCC CTT CAG TTG GTG AAC ATT GCT AGG GAC ATT AAA GGG GAC     1820
Gly Thr Ala Leu Gln Leu Val Asn Ile Ala Arg Asp Ile Lys Gly Asp
            520                 525                 530

GCA ACA GAA GGG AGA TTT TAC CTA CCA CTC TCA TTC TTT GGT CTT CGG     1868
Ala Thr Glu Gly Arg Phe Tyr Leu Pro Leu Ser Phe Phe Gly Leu Arg
        535                 540                 545
```

```
GAT GAA TCA AAG CTT GCG ATC CCG ACT GAT TGG ACG GAA CCT CGG CCT         1916
Asp Glu Ser Lys Leu Ala Ile Pro Thr Asp Trp Thr Glu Pro Arg Pro
        550                 555                 560

CAA GAT TTC GAC AAA CTC CTC AGT CTA TCT CCT TCG TCC ACA TTA CCA         1964
Gln Asp Phe Asp Lys Leu Leu Ser Leu Ser Pro Ser Ser Thr Leu Pro
565                 570                 575                 580

TCT TCA AAC GCC TCA GAA AGC TTC CGG TTC GAA TGG AAG ACG TAC TCG         2012
Ser Ser Asn Ala Ser Glu Ser Phe Arg Phe Glu Trp Lys Thr Tyr Ser
                585                 590                 595

CTT CCA TTA GTC GCC TAC GCA GAG GAT CTT GCC AAA CAT TCT TAT AAG         2060
Leu Pro Leu Val Ala Tyr Ala Glu Asp Leu Ala Lys His Ser Tyr Lys
            600                 605                 610

GGA ATT GAC CGA CTT CCT ACC GAG GTT CAA GCG GGA ATG CGA GCG GCT         2108
Gly Ile Asp Arg Leu Pro Thr Glu Val Gln Ala Gly Met Arg Ala Ala
            615                 620                 625

TGC GCG AGC TAC CTA CTG ATC GGC CGA GAG ATC AAA GTC GTT TGG AAA         2156
Cys Ala Ser Tyr Leu Leu Ile Gly Arg Glu Ile Lys Val Val Trp Lys
            630                 635                 640

GGA GAC GTC GGA GAG AGA AGG ACA GTT GCC GGA TGG AGG AGA GTA CGG         2204
Gly Asp Val Gly Glu Arg Arg Thr Val Ala Gly Trp Arg Arg Val Arg
645                 650                 655                 660

AAA GTC TTG AGT GTG GTC ATG AGC GGA TGG GAA GGG CAG TAAGACAGCG          2253
Lys Val Leu Ser Val Val Met Ser Gly Trp Glu Gly Gln
                665                 670

GAAGAATACC GACAGACAAT GATGAGTGAG AATAAAATCA TCCTCAATCT TCTTTCTCTA       2313

GGTGCTCTTT TTTGTTTTCT ATTATGACCA ACTCTAAAGG AACTGGCCTT GCAGATATTT       2373

CTCTTCCCCC CATCTTCCTC CTTTCCATCG TTTGTTCTTT CCATTTTTGT CGGTTTACTA       2433

TGTCAATTCT TTTTCTTGCT TTTTCTTATC AATCTAGACA ATTCTATAGA TGTTTAGAAT       2493

TTATACATTG ACAGGTTATA GACCATAAAG ACTAAAAAAA AAAAAAAAAA AAA             2546

(2) INFORMATION FOR SEQ ID NO:13:

(i) SEQUENCE CHARACTERISTICS:
        (A) LENGTH: 673 amino acids
        (B) TYPE: amino acid
        (D) TOPOLOGY: linear (ii) MOLECULE TYPE: protein (xi) SEQUENCE DESCRIPTION: SEQ ID NO:13:

Met Thr Ala Leu Ala Tyr Tyr Gln Ile His Leu Ile Tyr Thr Leu Pro
 1               5                  10                  15

Ile Leu Gly Leu Leu Gly Leu Leu Thr Ser Pro Ile Leu Thr Lys Phe
            20                  25                  30

Asp Ile Tyr Lys Ile Ser Ile Leu Val Phe Ile Ala Phe Ser Ala Thr
        35                  40                  45

Thr Pro Trp Asp Ser Trp Ile Ile Arg Asn Gly Ala Trp Thr Tyr Pro
    50                  55                  60

Ser Ala Glu Ser Gly Gln Gly Val Phe Gly Thr Phe Leu Asp Val Pro
65                  70                  75                  80

Tyr Glu Glu Tyr Ala Phe Phe Val Ile Gln Thr Val Ile Thr Gly Leu
                85                  90                  95

Val Tyr Val Leu Ala Thr Arg His Leu Leu Pro Ser Leu Ala Leu Pro
            100                 105                 110

Lys Thr Arg Ser Ser Ala Leu Ser Leu Ala Leu Lys Ala Leu Ile Pro
        115                 120                 125
```

```
Leu Pro Ile Ile Tyr Leu Phe Thr Ala His Pro Ser Pro Ser Pro Asp
    130                 135                 140

Pro Leu Val Thr Asp His Tyr Phe Tyr Met Arg Ala Leu Ser Leu Leu
145                 150                 155                 160

Ile Thr Pro Pro Thr Met Leu Leu Ala Ala Leu Ser Gly Glu Tyr Ala
                    165                 170                 175

Phe Asp Trp Lys Ser Gly Arg Ala Lys Ser Thr Ile Ala Ala Ile Met
                180                 185                 190

Ile Pro Thr Val Tyr Leu Ile Trp Val Asp Tyr Val Ala Val Gly Gln
            195                 200                 205

Asp Ser Trp Ser Ile Asn Asp Glu Lys Ile Val Gly Trp Arg Leu Gly
    210                 215                 220

Gly Val Leu Pro Ile Glu Glu Ala Met Phe Phe Leu Leu Thr Asn Leu
225                 230                 235                 240

Met Ile Val Leu Gly Leu Ser Ala Cys Asp His Thr Gln Ala Leu Tyr
                    245                 250                 255

Leu Leu His Gly Arg Thr Ile Tyr Gly Asn Lys Lys Met Pro Ser Ser
                260                 265                 270

Phe Pro Leu Ile Thr Pro Pro Val Leu Ser Leu Phe Phe Ser Ser Arg
    275                 280                 285

Pro Tyr Ser Ser Gln Pro Lys Arg Asp Leu Glu Leu Ala Val Lys Leu
    290                 295                 300

Leu Glu Lys Lys Ser Arg Ser Phe Phe Val Ala Ser Ala Gly Phe Pro
305                 310                 315                 320

Ser Glu Val Arg Glu Arg Leu Val Gly Leu Tyr Ala Phe Cys Arg Val
                325                 330                 335

Thr Asp Asp Leu Ile Asp Ser Pro Glu Val Ser Ser Asn Pro His Ala
                340                 345                 350

Thr Ile Asp Met Val Ser Asp Phe Leu Thr Leu Leu Phe Gly Pro Pro
                355                 360                 365

Leu His Pro Ser Gln Pro Asp Lys Ile Leu Ser Ser Pro Leu Leu Pro
    370                 375                 380

Pro Ser His Pro Ser Arg Pro Thr Gly Met Tyr Pro Leu Pro Pro Pro
385                 390                 395                 400

Pro Ser Leu Ser Pro Ala Glu Leu Val Gln Phe Leu Thr Glu Arg Val
                405                 410                 415

Pro Val Gln Tyr His Phe Ala Phe Arg Leu Leu Ala Lys Leu Gln Gly
                420                 425                 430

Leu Ile Pro Arg Tyr Pro Leu Asp Glu Leu Leu Arg Gly Tyr Thr Thr
    435                 440                 445

Asp Leu Ile Phe Pro Leu Ser Thr Glu Ala Val Gln Ala Arg Lys Thr
    450                 455                 460

Pro Ile Glu Thr Thr Ala Asp Leu Leu Asp Tyr Gly Leu Cys Val Ala
465                 470                 475                 480

Gly Ser Val Ala Glu Leu Leu Val Tyr Val Ser Trp Ala Ser Ala Pro
                485                 490                 495

Ser Gln Val Pro Ala Thr Ile Glu Glu Arg Glu Ala Val Leu Val Ala
                500                 505                 510

Ser Arg Glu Met Gly Thr Ala Leu Gln Leu Val Asn Ile Ala Arg Asp
                515                 520                 525

Ile Lys Gly Asp Ala Thr Glu Gly Arg Phe Tyr Leu Pro Leu Ser Phe
    530                 535                 540
```

-continued

```
Phe Gly Leu Arg Asp Glu Ser Lys Leu Ala Ile Pro Thr Asp Trp Thr
545                 550                 555                 560

Glu Pro Arg Pro Gln Asp Phe Asp Lys Leu Leu Ser Leu Ser Pro Ser
                565                 570                 575

Ser Thr Leu Pro Ser Ser Asn Ala Ser Glu Ser Phe Arg Phe Glu Trp
                580                 585                 590

Lys Thr Tyr Ser Leu Pro Leu Val Ala Tyr Ala Glu Asp Leu Ala Lys
            595                 600                 605

His Ser Tyr Lys Gly Ile Asp Arg Leu Pro Thr Glu Val Gln Ala Gly
        610                 615                 620

Met Arg Ala Ala Cys Ala Ser Tyr Leu Leu Ile Gly Arg Glu Ile Lys
625                 630                 635                 640

Val Val Trp Lys Gly Asp Val Gly Glu Arg Arg Thr Val Ala Gly Trp
                645                 650                 655

Arg Arg Val Arg Lys Val Leu Ser Val Val Met Ser Gly Trp Glu Gly
                660                 665                 670

Gln
```

(2) INFORMATION FOR SEQ ID NO:14:

(i) SEQUENCE CHARACTERISTICS:
        (A) LENGTH: 1882 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 82..1212
        (D) OTHER INFORMATION: /product= "PRcrtE"

(xi) SEQUENCE DESCRIPTION: SEQ ID NO:14:

```
GGCACGAGCC AATTTAAAGT GCACTCAGCC ATAGCTAACA CACAGAACTA CACATACATA      60

CACTCATCCG AAACACATAG G ATG GAT TAC GCG AAC ATC CTC ACA GCA ATT       111
                         Met Asp Tyr Ala Asn Ile Leu Thr Ala Ile
                           1               5                  10

CCA CTC GAG TTT ACT CCT CAG GAT GAT ATC GTG CTC CTT GAA CCG TAT       159
Pro Leu Glu Phe Thr Pro Gln Asp Asp Ile Val Leu Leu Glu Pro Tyr
                 15                  20                  25

CAC TAC CTA GGA AAG AAC CCT GGA AAA GAA ATT CGA TCA CAA CTC ATC       207
His Tyr Leu Gly Lys Asn Pro Gly Lys Glu Ile Arg Ser Gln Leu Ile
         30                  35                  40

GAG GCT TTC AAC TAT TGG TTG GAT GTC AAG AAG GAG GAT CTC GAG GTC       255
Glu Ala Phe Asn Tyr Trp Leu Asp Val Lys Lys Glu Asp Leu Glu Val
     45                  50                  55

ATC CAG AAC GTT GTT GGC ATG CTA CAT ACC GCT AGC TTA TTA ATG GAC       303
Ile Gln Asn Val Val Gly Met Leu His Thr Ala Ser Leu Leu Met Asp
 60                  65                  70

GAT GTG GAG GAT TCA TCG GTC CTC AGG CGT GGG TCG CCT GTG GCC CAT       351
Asp Val Glu Asp Ser Ser Val Leu Arg Arg Gly Ser Pro Val Ala His
 75                  80                  85                  90
```

```
CTA ATT TAC GGG ATT CCG CAG ACA ATA AAC ACT GCA AAC TAC GTC TAC        399
Leu Ile Tyr Gly Ile Pro Gln Thr Ile Asn Thr Ala Asn Tyr Val Tyr
            95                  100                 105

TTT CTG GCT TAT CAA GAG ATC TTC AAG CTT CGC CCA ACA CCG ATA CCC        447
Phe Leu Ala Tyr Gln Glu Ile Phe Lys Leu Arg Pro Thr Pro Ile Pro
        110                 115                 120

ATG CCT GTA ATT CCT CCT TCA TCT GCT TCG CTT CAA TCA TCC GTC TCC        495
Met Pro Val Ile Pro Pro Ser Ser Ala Ser Leu Gln Ser Ser Val Ser
            125                 130                 135

TCT GCA TCC TCC TCC TCC TCG GCC TCG TCT GAA AAC GGG GGC ACG TCA        543
Ser Ala Ser Ser Ser Ser Ser Ala Ser Ser Glu Asn Gly Gly Thr Ser
        140                 145                 150

ACT CCT AAT TCG CAG ATT CCG TTC TCG AAA GAT ACG TAT CTT GAT AAA        591
Thr Pro Asn Ser Gln Ile Pro Phe Ser Lys Asp Thr Tyr Leu Asp Lys
155                 160                 165                 170

GTG ATC ACA GAC GAG ATG CTT TCC CTC CAT AGA GGG CAA GGC CTG GAG        639
Val Ile Thr Asp Glu Met Leu Ser Leu His Arg Gly Gln Gly Leu Glu
                175                 180                 185

CTA TTC TGG AGA GAT AGT CTG ACG TGT CCT AGC GAA GAG GAA TAT GTG        687
Leu Phe Trp Arg Asp Ser Leu Thr Cys Pro Ser Glu Glu Glu Tyr Val
            190                 195                 200

AAA ATG GTT CTT GGA AAG ACG GGA GGT TTG TTC CGT ATA GCG GTC AGA        735
Lys Met Val Leu Gly Lys Thr Gly Gly Leu Phe Arg Ile Ala Val Arg
        205                 210                 215

TTG ATG ATG GCA AAG TCA GAA TGT GAC ATA GAC TTT GTC CAG CTT GTC        783
Leu Met Met Ala Lys Ser Glu Cys Asp Ile Asp Phe Val Gln Leu Val
220                 225                 230

AAC TTG ATC TCA ATA TAC TTC CAG ATC AGG GAT GAC TAT ATG AAC CTT        831
Asn Leu Ile Ser Ile Tyr Phe Gln Ile Arg Asp Asp Tyr Met Asn Leu
235                 240                 245                 250

CAG TCT TCT GAG TAT GCC CAT AAT AAG AAT TTT GCA GAG GAC CTC ACA        879
Gln Ser Ser Glu Tyr Ala His Asn Lys Asn Phe Ala Glu Asp Leu Thr
                255                 260                 265

GAA GGG AAA TTC AGT TTT CCC ACT ATC CAC TCG ATT CAT GCC AAC CCC        927
Glu Gly Lys Phe Ser Phe Pro Thr Ile His Ser Ile His Ala Asn Pro
            270                 275                 280

TCA TCG AGA CTC GTC ATC AAT ACG TTG CAG AAG AAA TCG ACC TCT CCT        975
Ser Ser Arg Leu Val Ile Asn Thr Leu Gln Lys Lys Ser Thr Ser Pro
        285                 290                 295

GAG ATC CTT CAC CAC TGT GTA AAC TAC ATG CGC ACA GAA ACC CAC TCA       1023
Glu Ile Leu His His Cys Val Asn Tyr Met Arg Thr Glu Thr His Ser
300                 305                 310

TTC GAA TAT ACT CAG GAA GTC CTC AAC ACC TTG TCA GGT GCA CTC GAG       1071
Phe Glu Tyr Thr Gln Glu Val Leu Asn Thr Leu Ser Gly Ala Leu Glu
315                 320                 325                 330

AGA GAA CTA GGA AGG CTT CAA GGA GAG TTC GCA GAA GCT AAC TCA AGG       1119
Arg Glu Leu Gly Arg Leu Gln Gly Glu Phe Ala Glu Ala Asn Ser Arg
                335                 340                 345

ATG GAT CTT GGA GAC GTA GAT TCG GAA GGA AGA ACG GGG AAG AAC GTC       1167
Met Asp Leu Gly Asp Val Asp Ser Glu Gly Arg Thr Gly Lys Asn Val
            350                 355                 360

AAA TTG GAA GCG ATC CTG AAA AAG CTA GCC GAT ATC CCT CTG TGAAAGAACA    1219
Lys Leu Glu Ala Ile Leu Lys Lys Leu Ala Asp Ile Pro Leu
        365                 370                 375

TATTCTCTCT CTCGTCTGTC CGTTTCTATC AGGGTTTTAT AAGTTGTCTC TTTATTCCTA     1279

AGGGTTTGTC AGATGATTGG ACTTGATGTG CTCTATTGCC CGTTCATCTT TTTCACTTCG     1339

ACTTTTTTCT CTACCGTGCA TGCCCATTCG CATTCTCTTG TTCATCTTGT GTTTAATTTG     1399

TTCGACATAA CATTAATCAT CGTGTCTTCT TCTTTTCGAA GAAATCTCGT GACTTGTTGA     1459
```

-continued

```
ACTTCAACTA TAATTAATCA TATTCATATC TCAAAGTCTT CGTCTTCTCG CAATGTGATT    1519

CCTCCTTCCA GTTCCCTCTT TGATTTCCTT CTCATTGATC GGTTTCTTTT TCTTTTTTGC    1579

TCTCCTGTCT CTTCTTTATT CGCCTTCCGT CTCTCTGTCT CGTTTTCTCT TCACTTTTTT    1639

TTTTCATCTT CTCTCGGTCA ACTTGTCATT TAATCTCTCT AGGGTCTCAT GTCAACACGT    1699

GCCAAGCATG TCATACGTGT GCAGGGTGAT GTACAGTCAT TTTGCCATCC CTCTTCGCAG    1759

GGTCTCATCT ATCTTGTCTA TCGACTTTTC CTCTTTTTGA ATTTCCTCGG AGTTTTATCT    1819

TGGTATAAGC AATGGAGAAG AGCGCAAAAA AAAAAAAAAA AAAAAAAAAA AAAAAACTCG    1879

AGG                                                                   1882
```

(2) INFORMATION FOR SEQ ID NO:15:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asp Tyr Ala Asn Ile Leu Thr Ala Ile Pro Leu Glu Phe Thr Pro
  1               5                  10                  15

Gln Asp Asp Ile Val Leu Leu Glu Pro Tyr His Tyr Leu Gly Lys Asn
                 20                  25                  30

Pro Gly Lys Glu Ile Arg Ser Gln Leu Ile Glu Ala Phe Asn Tyr Trp
             35                  40                  45

Leu Asp Val Lys Lys Glu Asp Leu Glu Val Ile Gln Asn Val Val Gly
         50                  55                  60

Met Leu His Thr Ala Ser Leu Leu Met Asp Asp Val Glu Asp Ser Ser
 65                  70                  75                  80

Val Leu Arg Arg Gly Ser Pro Val Ala His Leu Ile Tyr Gly Ile Pro
                 85                  90                  95

Gln Thr Ile Asn Thr Ala Asn Tyr Val Tyr Phe Leu Ala Tyr Gln Glu
            100                 105                 110

Ile Phe Lys Leu Arg Pro Thr Pro Ile Pro Met Pro Val Ile Pro Pro
        115                 120                 125

Ser Ser Ala Ser Leu Gln Ser Ser Val Ser Ser Ala Ser Ser Ser Ser
    130                 135                 140

Ser Ala Ser Ser Glu Asn Gly Gly Thr Ser Thr Pro Asn Ser Gln Ile
145                 150                 155                 160

Pro Phe Ser Lys Asp Thr Tyr Leu Asp Lys Val Ile Thr Asp Glu Met
                165                 170                 175

Leu Ser Leu His Arg Gly Gln Gly Leu Glu Leu Phe Trp Arg Asp Ser
            180                 185                 190

Leu Thr Cys Pro Ser Glu Glu Tyr Val Lys Met Val Leu Gly Lys
        195                 200                 205

Thr Gly Gly Leu Phe Arg Ile Ala Val Arg Leu Met Met Ala Lys Ser
    210                 215                 220

Glu Cys Asp Ile Asp Phe Val Gln Leu Val Asn Leu Ile Ser Ile Tyr
225                 230                 235                 240

Phe Gln Ile Arg Asp Asp Tyr Met Asn Leu Gln Ser Ser Glu Tyr Ala
                245                 250                 255

His Asn Lys Asn Phe Ala Glu Asp Leu Thr Glu Gly Lys Phe Ser Phe
            260                 265                 270
```

```
Pro Thr Ile His Ser Ile His Ala Asn Pro Ser Ser Arg Leu Val Ile
        275                 280                 285

Asn Thr Leu Gln Lys Lys Ser Thr Ser Pro Glu Ile Leu His His Cys
        290                 295                 300

Val Asn Tyr Met Arg Thr Glu Thr His Ser Phe Glu Tyr Thr Gln Glu
305                 310                 315                 320

Val Leu Asn Thr Leu Ser Gly Ala Leu Glu Arg Glu Leu Gly Arg Leu
                325                 330                 335

Gln Gly Glu Phe Ala Glu Ala Asn Ser Arg Met Asp Leu Gly Asp Val
            340                 345                 350

Asp Ser Glu Gly Arg Thr Gly Lys Asn Val Lys Leu Glu Ala Ile Leu
        355                 360                 365

Lys Lys Leu Ala Asp Ile Pro Leu
        370                 375

(2) INFORMATION FOR SEQ ID NO:16:

(i) SEQUENCE CHARACTERISTICS:
        (A) LENGTH: 2058 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 46..1794
        (D) OTHER INFORMATION: /product= "PRcrtI"

(xi) SEQUENCE DESCRIPTION: SEQ ID NO:16:

CCTCGCCGAA TCTAACTTGA CACATAACTC TAGTATCTAT ACTCG ATG GGA AAA        54
                                                  Met Gly Lys
                                                    1

GAA CAA GAT CAG GAT AAA CCC ACA GCT ATC ATC GTG GGA TGT GGT ATC     102
Glu Gln Asp Gln Asp Lys Pro Thr Ala Ile Ile Val Gly Cys Gly Ile
  5                  10                  15

GGT GGA ATC GCC ACT GCC GCT CGT CTT GCT AAA GAA GGT TTC CAG GTC     150
Gly Gly Ile Ala Thr Ala Ala Arg Leu Ala Lys Glu Gly Phe Gln Val
 20                  25                  30                  35

ACG GTG TTC GAG AAG AAC GAC TAC TCC GGA GGT CGA TGC TCT TTA ATC     198
Thr Val Phe Glu Lys Asn Asp Tyr Ser Gly Gly Arg Cys Ser Leu Ile
                 40                  45                  50

GAG CGA GAT GGT TAT CGA TTC GAT CAG GGG CCC AGT TTG CTG CTC TTG     246
Glu Arg Asp Gly Tyr Arg Phe Asp Gln Gly Pro Ser Leu Leu Leu Leu
             55                  60                  65

CCA GAT CTC TTC AAG CAG ACA TTC GAA GAT TTG GGA GAG AAG ATG GAA     294
Pro Asp Leu Phe Lys Gln Thr Phe Glu Asp Leu Gly Glu Lys Met Glu
         70                  75                  80

GAT TGG GTC GAT CTC ATC AAG TGT GAA CCC AAC TAT GTT TGC CAC TTC     342
Asp Trp Val Asp Leu Ile Lys Cys Glu Pro Asn Tyr Val Cys His Phe
     85                  90                  95

CAC GAT GAA GAG ACT TTC ACT TTT TCA ACC GAC ATG GCG TTG CTC AAG     390
His Asp Glu Glu Thr Phe Thr Phe Ser Thr Asp Met Ala Leu Leu Lys
100                 105                 110                 115
```

-continued

| | | | | | | | | | | | | | | | |
|---|---|---|---|---|---|---|---|---|---|---|---|---|---|---|---|
| CGG | GAA | GTC | GAG | CGT | TTT | GAA | GGC | AAA | GAT | GGA | TTT | GAT | CGG | TTC | TTG | 438 |
| Arg | Glu | Val | Glu | Arg | Phe | Glu | Gly | Lys | Asp | Gly | Phe | Asp | Arg | Phe | Leu | |
| | | | 120 | | | | | 125 | | | | | 130 | | | |

| TCG | TTT | ATC | CAA | GAA | GCC | CAC | AGA | CAT | TAC | GAG | CTT | GCT | GTC | GTT | CAC | 486 |
| Ser | Phe | Ile | Gln | Glu | Ala | His | Arg | His | Tyr | Glu | Leu | Ala | Val | Val | His | |
| | | | 135 | | | | | 140 | | | | | 145 | | | |

| GTC | CTG | CAG | AAG | AAC | TTC | CCT | GGC | TTC | GCA | GCA | TTC | TTA | CGG | CTA | CAG | 534 |
| Val | Leu | Gln | Lys | Asn | Phe | Pro | Gly | Phe | Ala | Ala | Phe | Leu | Arg | Leu | Gln | |
| | | | 150 | | | | | 155 | | | | | 160 | | | |

| TTC | ATT | GGC | CAA | ATC | CTG | GCT | CTT | CAC | CCC | TTC | GAG | TCT | ATC | TGG | ACA | 582 |
| Phe | Ile | Gly | Gln | Ile | Leu | Ala | Leu | His | Pro | Phe | Glu | Ser | Ile | Trp | Thr | |
| | | | 165 | | | | | 170 | | | | | 175 | | | |

| AGA | GTT | TGT | CGA | TAT | TTC | AAG | ACC | GAC | AGA | TTA | CGA | AGA | GTC | TTC | TCG | 630 |
| Arg | Val | Cys | Arg | Tyr | Phe | Lys | Thr | Asp | Arg | Leu | Arg | Arg | Val | Phe | Ser | |
| 180 | | | | | 185 | | | | | 190 | | | | | 195 | |

| TTT | GCA | GTG | ATG | TAC | ATG | GGT | CAA | AGC | CCA | TAC | AGT | GCG | CCC | GGA | ACA | 678 |
| Phe | Ala | Val | Met | Tyr | Met | Gly | Gln | Ser | Pro | Tyr | Ser | Ala | Pro | Gly | Thr | |
| | | | | 200 | | | | | 205 | | | | | 210 | | |

| TAT | TCC | TTG | CTC | CAA | TAC | ACC | GAA | TTG | ACC | GAG | GGC | ATC | TGG | TAT | CCG | 726 |
| Tyr | Ser | Leu | Leu | Gln | Tyr | Thr | Glu | Leu | Thr | Glu | Gly | Ile | Trp | Tyr | Pro | |
| | | | 215 | | | | | 220 | | | | | 225 | | | |

| AGA | GGA | GGC | TTT | TGG | CAG | GTT | CCT | AAT | ACT | CTT | CTT | CAG | ATC | GTC | AAG | 774 |
| Arg | Gly | Gly | Phe | Trp | Gln | Val | Pro | Asn | Thr | Leu | Leu | Gln | Ile | Val | Lys | |
| | | | 230 | | | | | 235 | | | | | 240 | | | |

| CGC | AAC | AAT | CCC | TCA | GCC | AAG | TTC | AAT | TTC | AAC | GCT | CCA | GTT | TCC | CAG | 822 |
| Arg | Asn | Asn | Pro | Ser | Ala | Lys | Phe | Asn | Phe | Asn | Ala | Pro | Val | Ser | Gln | |
| | | | 245 | | | | | 250 | | | | | 255 | | | |

| GTT | CTT | CTC | TCT | CCT | GCC | AAG | GAC | CGA | GCG | ACT | GGT | GTT | CGA | CTT | GAA | 870 |
| Val | Leu | Leu | Ser | Pro | Ala | Lys | Asp | Arg | Ala | Thr | Gly | Val | Arg | Leu | Glu | |
| 260 | | | | | 265 | | | | | 270 | | | | | 275 | |

| TCC | GGC | GAG | GAA | CAT | CAC | GCC | GAT | GTT | GTG | ATT | GTC | AAT | GCT | GAC | CTC | 918 |
| Ser | Gly | Glu | Glu | His | His | Ala | Asp | Val | Val | Ile | Val | Asn | Ala | Asp | Leu | |
| | | | | 280 | | | | | 285 | | | | | 290 | | |

| GTT | TAC | GCC | TCC | GAG | CAC | TTG | ATT | CCT | GAC | GAT | GCC | AGA | AAC | AAG | ATT | 966 |
| Val | Tyr | Ala | Ser | Glu | His | Leu | Ile | Pro | Asp | Asp | Ala | Arg | Asn | Lys | Ile | |
| | | | 295 | | | | | 300 | | | | | 305 | | | |

| GGC | CAA | CTG | GGT | GAA | GTC | AAG | AGA | AGT | TGG | TGG | GCT | GAC | TTA | GTT | GGT | 1014 |
| Gly | Gln | Leu | Gly | Glu | Val | Lys | Arg | Ser | Trp | Trp | Ala | Asp | Leu | Val | Gly | |
| | | | 310 | | | | | 315 | | | | | 320 | | | |

| GGA | AAG | AAG | CTC | AAG | GGA | AGT | TGC | AGT | AGT | TTG | AGC | TTC | TAC | TGG | AGC | 1062 |
| Gly | Lys | Lys | Leu | Lys | Gly | Ser | Cys | Ser | Ser | Leu | Ser | Phe | Tyr | Trp | Ser | |
| | | | 325 | | | | | 330 | | | | | 335 | | | |

| ATG | GAC | CGA | ATC | GTG | GAC | GGT | CTG | GGC | GGA | CAC | AAT | ATC | TTC | TTG | GCC | 1110 |
| Met | Asp | Arg | Ile | Val | Asp | Gly | Leu | Gly | Gly | His | Asn | Ile | Phe | Leu | Ala | |
| 340 | | | | | 345 | | | | | 350 | | | | | 355 | |

| GAG | GAC | TTC | AAG | GGA | TCA | TTC | GAC | ACA | ATC | TTC | GAG | GAG | TTG | GGT | CTC | 1158 |
| Glu | Asp | Phe | Lys | Gly | Ser | Phe | Asp | Thr | Ile | Phe | Glu | Glu | Leu | Gly | Leu | |
| | | | | 360 | | | | | 365 | | | | | 370 | | |

| CCA | GCC | GAT | CCT | TCC | TTT | TAC | GTG | AAC | GTT | CCC | TCG | CGA | ATC | GAT | CCT | 1206 |
| Pro | Ala | Asp | Pro | Ser | Phe | Tyr | Val | Asn | Val | Pro | Ser | Arg | Ile | Asp | Pro | |
| | | | 375 | | | | | 380 | | | | | 385 | | | |

| TCT | GCC | GCT | CCC | GAA | GGC | AAA | GAT | GCT | ATC | GTC | ATT | CTT | GTG | CCG | TGT | 1254 |
| Ser | Ala | Ala | Pro | Glu | Gly | Lys | Asp | Ala | Ile | Val | Ile | Leu | Val | Pro | Cys | |
| | | | 390 | | | | | 395 | | | | | 400 | | | |

| GGC | CAT | ATC | GAC | GCT | TCG | AAC | CCT | CAA | GAT | TAC | AAC | AAG | CTT | GTT | GCT | 1302 |
| Gly | His | Ile | Asp | Ala | Ser | Asn | Pro | Gln | Asp | Tyr | Asn | Lys | Leu | Val | Ala | |
| | | | 405 | | | | | 410 | | | | | 415 | | | |

| CGG | GCA | AGG | AAG | TTT | GTG | ATC | CAA | ACG | CTT | TCC | GCC | AAG | CTT | GGA | CTT | 1350 |
| Arg | Ala | Arg | Lys | Phe | Val | Ile | Gln | Thr | Leu | Ser | Ala | Lys | Leu | Gly | Leu | |
| 420 | | | | | 425 | | | | | 430 | | | | | 435 | |

```
CCC GAC TTT GAA AAA ATG ATT GTG GCA GAG AAG GTT CAC GAT GCT CCC      1398
Pro Asp Phe Glu Lys Met Ile Val Ala Glu Lys Val His Asp Ala Pro
                440                 445                 450

TCT TGG GAG AAA GAA TTT AAC CTC AAG GAC GGA AGC ATC TTG GGA CTG      1446
Ser Trp Glu Lys Glu Phe Asn Leu Lys Asp Gly Ser Ile Leu Gly Leu
                455                 460                 465

GCT CAC AAC TTT ATG CAA GTT CTT GGT TTC AGG CCG AGC ACC AGA CAT      1494
Ala His Asn Phe Met Gln Val Leu Gly Phe Arg Pro Ser Thr Arg His
                470                 475                 480

CCC AAG TAT GAC AAG TTG TTC TTT GTC GGG GCT TCG ACT CAT CCC GGA      1542
Pro Lys Tyr Asp Lys Leu Phe Phe Val Gly Ala Ser Thr His Pro Gly
            485                 490                 495

ACT GGG GTT CCC ATC GTC TTG GCT GGA GCC AAG TTA ACT GCC AAC CAA      1590
Thr Gly Val Pro Ile Val Leu Ala Gly Ala Lys Leu Thr Ala Asn Gln
500                 505                 510                 515

GTT CTC GAA TCC TTT GAC CGA TCC CCA GCT CCA GAT CCC AAT ATG TCA      1638
Val Leu Glu Ser Phe Asp Arg Ser Pro Ala Pro Asp Pro Asn Met Ser
                520                 525                 530

CTC TCC GTA CCA TAT GGA AAA CCT CTC AAA TCA AAT GGA ACG GGT ATC      1686
Leu Ser Val Pro Tyr Gly Lys Pro Leu Lys Ser Asn Gly Thr Gly Ile
                535                 540                 545

GAT TCT CAG GTC CAG CTG AAG TTC ATG GAT TTG GAG AGA TGG GTA TAC      1734
Asp Ser Gln Val Gln Leu Lys Phe Met Asp Leu Glu Arg Trp Val Tyr
                550                 555                 560

CTT TTG GTG TTG TTG ATT GGG GCC GTG ATC GCT CGA TCC GTT GGT GTT      1782
Leu Leu Val Leu Leu Ile Gly Ala Val Ile Ala Arg Ser Val Gly Val
                565                 570                 575

CTT GCT TTC TGAAGCAAGA CAACGATCGT TTCTTAGAGT TTTTTTTAGT              1831
Leu Ala Phe
580

CTCTTCCTGT GTTCTCTCTA TATACATACT CTGCTCGTCT GTTCTCTTCT CGAGGGTTCC    1891

TCTTTACTTT GTGTCAGAGT CATACCCGGT CTCTCTCAAC GTCCGTTTGA GGGCTAGACA    1951

ATTGTTAGTC TCGAAATCTC CATCACCTCA AGTCTGATGT TCATCATCTT TTTTATTCGT    2011

TGCAATATAC ATGACTGTTA TGGACCGAAA AAAAAAAAAA AAAAAAA                  2058

(2) INFORMATION FOR SEQ ID NO:17:

(i) SEQUENCE CHARACTERISTICS:
        (A) LENGTH: 582 amino acids
        (B) TYPE: amino acid
        (D) TOPOLOGY: linear (ii) MOLECULE TYPE: protein (xi) SEQUENCE DESCRIPTION: SEQ ID NO:17:

Met Gly Lys Glu Gln Asp Gln Asp Lys Pro Thr Ala Ile Ile Val Gly
 1               5                  10                  15

Cys Gly Ile Gly Gly Ile Ala Thr Ala Ala Arg Leu Ala Lys Glu Gly
                20                  25                  30

Phe Gln Val Thr Val Phe Glu Lys Asn Asp Tyr Ser Gly Gly Arg Cys
            35                  40                  45

Ser Leu Ile Glu Arg Asp Gly Tyr Arg Phe Asp Gln Gly Pro Ser Leu
        50                  55                  60

Leu Leu Leu Pro Asp Leu Phe Lys Gln Thr Phe Glu Asp Leu Gly Glu
 65                 70                  75                  80

Lys Met Glu Asp Trp Val Asp Leu Ile Lys Cys Glu Pro Asn Tyr Val
                85                  90                  95
```

-continued

```
Cys His Phe His Asp Glu Glu Thr Phe Thr Phe Ser Thr Asp Met Ala
             100                 105                 110

Leu Leu Lys Arg Glu Val Glu Arg Phe Glu Gly Lys Asp Gly Phe Asp
        115                 120                 125

Arg Phe Leu Ser Phe Ile Gln Glu Ala His Arg His Tyr Glu Leu Ala
        130                 135                 140

Val Val His Val Leu Gln Lys Asn Phe Pro Gly Phe Ala Ala Phe Leu
145                 150                 155                 160

Arg Leu Gln Phe Ile Gly Gln Ile Leu Ala Leu His Pro Phe Glu Ser
                165                 170                 175

Ile Trp Thr Arg Val Cys Arg Tyr Phe Lys Thr Asp Arg Leu Arg Arg
                180                 185                 190

Val Phe Ser Phe Ala Val Met Tyr Met Gly Gln Ser Pro Tyr Ser Ala
                195                 200                 205

Pro Gly Thr Tyr Ser Leu Leu Gln Tyr Thr Glu Leu Thr Glu Gly Ile
        210                 215                 220

Trp Tyr Pro Arg Gly Gly Phe Trp Gln Val Pro Asn Thr Leu Leu Gln
225                 230                 235                 240

Ile Val Lys Arg Asn Asn Pro Ser Ala Lys Phe Asn Phe Asn Ala Pro
                245                 250                 255

Val Ser Gln Val Leu Leu Ser Pro Ala Lys Asp Arg Ala Thr Gly Val
                260                 265                 270

Arg Leu Glu Ser Gly Glu Glu His His Ala Asp Val Val Ile Val Asn
        275                 280                 285

Ala Asp Leu Val Tyr Ala Ser Glu His Leu Ile Pro Asp Asp Ala Arg
        290                 295                 300

Asn Lys Ile Gly Gln Leu Gly Glu Val Lys Arg Ser Trp Ala Asp
305                 310                 315                 320

Leu Val Gly Gly Lys Lys Leu Lys Gly Ser Cys Ser Ser Leu Ser Phe
                325                 330                 335

Tyr Trp Ser Met Asp Arg Ile Val Asp Gly Leu Gly Gly His Asn Ile
                340                 345                 350

Phe Leu Ala Glu Asp Phe Lys Gly Ser Phe Asp Thr Ile Phe Glu Glu
        355                 360                 365

Leu Gly Leu Pro Ala Asp Pro Ser Phe Tyr Val Asn Val Pro Ser Arg
        370                 375                 380

Ile Asp Pro Ser Ala Ala Pro Glu Gly Lys Asp Ala Ile Val Ile Leu
385                 390                 395                 400

Val Pro Cys Gly His Ile Asp Ala Ser Asn Pro Gln Asp Tyr Asn Lys
                405                 410                 415

Leu Val Ala Arg Ala Arg Lys Phe Val Ile Gln Thr Leu Ser Ala Lys
                420                 425                 430

Leu Gly Leu Pro Asp Phe Glu Lys Met Ile Val Ala Glu Lys Val His
        435                 440                 445

Asp Ala Pro Ser Trp Glu Lys Glu Phe Asn Leu Lys Asp Gly Ser Ile
        450                 455                 460

Leu Gly Leu Ala His Asn Phe Met Gln Val Leu Gly Phe Arg Pro Ser
465                 470                 475                 480

Thr Arg His Pro Lys Tyr Asp Lys Leu Phe Phe Val Gly Ala Ser Thr
                485                 490                 495

His Pro Gly Thr Gly Val Pro Ile Val Leu Ala Gly Ala Lys Leu Thr
        500                 505                 510
```

```
Ala Asn Gln Val Leu Glu Ser Phe Asp Arg Ser Pro Ala Pro Asp Pro
         515                 520                 525

Asn Met Ser Leu Ser Val Pro Tyr Gly Lys Pro Leu Lys Ser Asn Gly
         530                 535                 540

Thr Gly Ile Asp Ser Gln Val Gln Leu Lys Phe Met Asp Leu Glu Arg
545                 550                 555                 560

Trp Val Tyr Leu Val Leu Leu Ile Gly Ala Val Ile Ala Arg Ser
             565                 570                 575

Val Gly Val Leu Ala Phe
             580
```

(2) INFORMATION FOR SEQ ID NO:18:

(i) SEQUENCE CHARACTERISTICS:
        (A) LENGTH: 2470 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 177..2198
        (D) OTHER INFORMATION: /product= "PRcrtY"

(xi) SEQUENCE DESCRIPTION: SEQ ID NO:18:

```
AACAAGAAGT GGACACAGAG AGATCTTTGC TGAAGAGTTG TATTCCAGAA AGGGAAAACA    60

AAGGAAAGAA GCGCCGAAGC ACATCACCAA CTTCAGCAAG CCGGTCCAGC CCGATCTCGG   120

ATAGACATCA TCTTACCCAA CTCGTATCAT CCCCAACAGA TAGAGTTTTT GTCGCA       176

ATG ACG GCT CTC GCA TAT TAC CAG ATC CAT CTG ATC TAT ACT CTC CCA    224
Met Thr Ala Leu Ala Tyr Tyr Gln Ile His Leu Ile Tyr Thr Leu Pro
 1               5                  10                  15

ATT CTT GGT CTT CTC GGC CTG CTC ACT TCC CCG ATT TTG ACA AAA TTT    272
Ile Leu Gly Leu Leu Gly Leu Leu Thr Ser Pro Ile Leu Thr Lys Phe
             20                  25                  30

GAC ATC TAC AAA ATA TCG ATC CTC GTA TTT ATT GCG TTT AGT GCA ACC    320
Asp Ile Tyr Lys Ile Ser Ile Leu Val Phe Ile Ala Phe Ser Ala Thr
         35                  40                  45

ACA CCA TGG GAC TCA TGG ATC ATC AGA AAT GGC GCA TGG ACA TAT CCA    368
Thr Pro Trp Asp Ser Trp Ile Ile Arg Asn Gly Ala Trp Thr Tyr Pro
 50                  55                  60

TCA GCG GAG AGT GGC CAA GGC GTG TTT GGA ACG TTT CTA GAT GTT CCA    416
Ser Ala Glu Ser Gly Gln Gly Val Phe Gly Thr Phe Leu Asp Val Pro
 65                  70                  75                  80

TAT GAA GAG TAC GCT TTC TTT GTC ATT CAA ACC GTA ATC ACC GGC TTG    464
Tyr Glu Glu Tyr Ala Phe Phe Val Ile Gln Thr Val Ile Thr Gly Leu
                 85                  90                  95

GTC TAC GTC TTG GCA ACT AGG CAC CTT CTC CCA TCT CTC GCG CTT CCC    512
Val Tyr Val Leu Ala Thr Arg His Leu Leu Pro Ser Leu Ala Leu Pro
            100                 105                 110

AAG ACT AGA TCG TCC GCC CTT TCT CTC GCG CTC AAG GCG CTC ATC CCT    560
Lys Thr Arg Ser Ser Ala Leu Ser Leu Ala Leu Lys Ala Leu Ile Pro
        115                 120                 125
```

```
CTG CCC ATT ATC TAC CTA TTT ACC GCT CAC CCC AGC CCA TCG CCC GAC          608
Leu Pro Ile Ile Tyr Leu Phe Thr Ala His Pro Ser Pro Ser Pro Asp
    130                 135                 140

CCG CTC GTG ACA GAT CAC TAC TTC TAC ATG CGG GCA CTC TCC TTA CTC          656
Pro Leu Val Thr Asp His Tyr Phe Tyr Met Arg Ala Leu Ser Leu Leu
145                 150                 155                 160

ATC ACC CCA CCT ACC ATG CTC TTG GCA GCA TTA TCA GGC GAA TAT GCT          704
Ile Thr Pro Pro Thr Met Leu Leu Ala Ala Leu Ser Gly Glu Tyr Ala
                165                 170                 175

TTC GAT TGG AAA AGT GGC CGA GCA AAG TCA ACT ATT GCA GCA ATC ATG          752
Phe Asp Trp Lys Ser Gly Arg Ala Lys Ser Thr Ile Ala Ala Ile Met
            180                 185                 190

ATC CCG ACG GTG TAT CTG ATT TGG GTA GAT TAT GTT GCT GTC GGT CAA          800
Ile Pro Thr Val Tyr Leu Ile Trp Val Asp Tyr Val Ala Val Gly Gln
        195                 200                 205

GAC TCT TGG TCG ATC AAC GAT GAG AAG ATT GTA GGG TGG AGG CTT GGA          848
Asp Ser Trp Ser Ile Asn Asp Glu Lys Ile Val Gly Trp Arg Leu Gly
    210                 215                 220

GGT GTA CTA CCC ATT GAG GAA GCT ATG TTC TTC TTA CTG ACG AAT CTA          896
Gly Val Leu Pro Ile Glu Glu Ala Met Phe Phe Leu Leu Thr Asn Leu
225                 230                 235                 240

ATG ATT GTT CTG GGT CTG TCT GCC TGC GAT CAT ACT CAG GCC CTA TAC          944
Met Ile Val Leu Gly Leu Ser Ala Cys Asp His Thr Gln Ala Leu Tyr
                245                 250                 255

CTG CTA CAC GGT CGA ACT ATT TAT GGC AAC AAA AAG ATG CCA TCT TCA          992
Leu Leu His Gly Arg Thr Ile Tyr Gly Asn Lys Lys Met Pro Ser Ser
            260                 265                 270

TTT CCC CTC ATT ACA CCG CCT GTG CTC TCC CTG TTT TTT AGC AGC CGA         1040
Phe Pro Leu Ile Thr Pro Pro Val Leu Ser Leu Phe Phe Ser Ser Arg
        275                 280                 285

CCA TAC TCT TCT CAG CCA AAA CGT GAC TTG GAA CTG GCA GTC AAG TTG         1088
Pro Tyr Ser Ser Gln Pro Lys Arg Asp Leu Glu Leu Ala Val Lys Leu
    290                 295                 300

TTG GAG AAA AAG AGC CGG AGC TTT TTT GTT GCC TCG GCT GGA TTT CCT         1136
Leu Glu Lys Lys Ser Arg Ser Phe Phe Val Ala Ser Ala Gly Phe Pro
305                 310                 315                 320

AGC GAA GTT AGG GAG AGG CTG GTT GGA CTA TAC GCA TTC TGC CGG GTG         1184
Ser Glu Val Arg Glu Arg Leu Val Gly Leu Tyr Ala Phe Cys Arg Val
                325                 330                 335

ACT GAT GAT CTT ATC GAC TCT CCT GAA GTA TCT TCC AAC CCG CAT GCC         1232
Thr Asp Asp Leu Ile Asp Ser Pro Glu Val Ser Ser Asn Pro His Ala
            340                 345                 350

ACA ATT GAC ATG GTC TCC GAT TTT CTT ACC CTA CTA TTT GGG CCC CCG         1280
Thr Ile Asp Met Val Ser Asp Phe Leu Thr Leu Leu Phe Gly Pro Pro
        355                 360                 365

CTA CAC CCT TCG CAA CCT GAC AAG ATC CTT TCT TCG CCT TTA CTT CCT         1328
Leu His Pro Ser Gln Pro Asp Lys Ile Leu Ser Ser Pro Leu Leu Pro
    370                 375                 380

CCT TCG CAC CCT TCC CGA CCC ACG GGA ATG TAT CCC CTC CCG CCT CCT         1376
Pro Ser His Pro Ser Arg Pro Thr Gly Met Tyr Pro Leu Pro Pro Pro
385                 390                 395                 400

CCT TCG CTC TCG CCT GCC GAG CTC GTT CAA TTC CTT ACC GAA AGG GTT         1424
Pro Ser Leu Ser Pro Ala Glu Leu Val Gln Phe Leu Thr Glu Arg Val
                405                 410                 415

CCC GTT CAA TAC CAT TTC GCC TTC AGG TTG CTC GCT AAG TTG CAA GGG         1472
Pro Val Gln Tyr His Phe Ala Phe Arg Leu Leu Ala Lys Leu Gln Gly
            420                 425                 430

CTG ATC CCT CGA TAC CCA CTC GAC GAA CTC CTT AGA GGA TAC ACC ACT         1520
Leu Ile Pro Arg Tyr Pro Leu Asp Glu Leu Leu Arg Gly Tyr Thr Thr
        435                 440                 445
```

```
GAT CTT ATC TTT CCC TTA TCG ACA GAG GCA GTC CAG GCT CGG AAG ACG    1568
Asp Leu Ile Phe Pro Leu Ser Thr Glu Ala Val Gln Ala Arg Lys Thr
450                 455                 460

CCT ATC GAG ACC ACA GCT GAC TTG CTG GAC TAT GGT CTA TGT GTA GCA    1616
Pro Ile Glu Thr Thr Ala Asp Leu Leu Asp Tyr Gly Leu Cys Val Ala
465                 470                 475                 480

GGC TCA GTC GCC GAG CTA TTG GTC TAT GTC TCT TGG GCA AGT GCA CCA    1664
Gly Ser Val Ala Glu Leu Leu Val Tyr Val Ser Trp Ala Ser Ala Pro
                485                 490                 495

AGT CAG GTC CCT GCC ACC ATA GAA GAA AGA GAA GCT GTG TTA GTG GCA    1712
Ser Gln Val Pro Ala Thr Ile Glu Glu Arg Glu Ala Val Leu Val Ala
            500                 505                 510

AGC CGA GAG ATG GGA ACT GCC CTT CAG TTG GTG AAC ATT GCT AGG GAC    1760
Ser Arg Glu Met Gly Thr Ala Leu Gln Leu Val Asn Ile Ala Arg Asp
        515                 520                 525

ATT AAA GGG GAC GCA ACA GAA GGG AGA TTT TAC CTA CCA CTC TCA TTC    1808
Ile Lys Gly Asp Ala Thr Glu Gly Arg Phe Tyr Leu Pro Leu Ser Phe
    530                 535                 540

TTT GGT CTT CGG GAT GAA TCA AAG CTT GCG ATC CCG ACT GAT TGG ACG    1856
Phe Gly Leu Arg Asp Glu Ser Lys Leu Ala Ile Pro Thr Asp Trp Thr
545                 550                 555                 560

GAA CCT CGG CCT CAA GAT TTC GAC AAA CTC CTC AGT CTA TCT CCT TCG    1904
Glu Pro Arg Pro Gln Asp Phe Asp Lys Leu Leu Ser Leu Ser Pro Ser
                565                 570                 575

TCC ACA TTA CCA TCT TCA AAC GCC TCA GAA AGC TTC CGG TTC GAA TGG    1952
Ser Thr Leu Pro Ser Ser Asn Ala Ser Glu Ser Phe Arg Phe Glu Trp
            580                 585                 590

AAG ACG TAC TCG CTT CCA TTA GTC GCC TAC GCA GAG GAT CTT GCC AAA    2000
Lys Thr Tyr Ser Leu Pro Leu Val Ala Tyr Ala Glu Asp Leu Ala Lys
        595                 600                 605

CAT TCT TAT AAG GGA ATT GAC CGA CTT CCT ACC GAG GTT CAA GCG GGA    2048
His Ser Tyr Lys Gly Ile Asp Arg Leu Pro Thr Glu Val Gln Ala Gly
    610                 615                 620

ATG CGA GCG GCT TGC GCG AGC TAC CTA CTG ATC GGC CGA GAG ATC AAA    2096
Met Arg Ala Ala Cys Ala Ser Tyr Leu Leu Ile Gly Arg Glu Ile Lys
625                 630                 635                 640

GTC GTT TGG AAA GGA GAC GTC GGA GAG AGA AGG ACA GTT GCC GGA TGG    2144
Val Val Trp Lys Gly Asp Val Gly Glu Arg Arg Thr Val Ala Gly Trp
                645                 650                 655

AGG AGA GTA CGG AAA GTC TTG AGT GTG GTC ATG AGC GGA TGG GAA GGG    2192
Arg Arg Val Arg Lys Val Leu Ser Val Val Met Ser Gly Trp Glu Gly
            660                 665                 670

CAG TAAGACAGCG GAAGAATACC GACAGACAAT GATGAGTGAG AATAAAATCA         2245
Gln

TCCTCAATCT TCTTTCTCTA GGTGCTCTTT TTTGTTTTCT ATTATGACCA ACTCTAAAGG  2305

AACTGGCCTT GCAGATATTT CTCTTCCCCC CATCTTCCTC CTTTCCATCG TTTGTTCTTT  2365

CCATTTTTGT CGGTTTACTA TGTCAATTCT TTTTCTTGCT TTTTCTTATC AATCTAGACA  2425

ATTCTATAGA TGTTTAGAAT TTATACAAAA AAAAAAAAAA AAAAA                  2470

(2) INFORMATION FOR SEQ ID NO:19:

(i) SEQUENCE CHARACTERISTICS:
        (A) LENGTH: 673 amino acids
        (B) TYPE: amino acid
        (D) TOPOLOGY: linear
```

-continued (ii) MOLECULE TYPE: protein (xi) SEQUENCE DESCRIPTION: SEQ ID NO:19:

```
Met Thr Ala Leu Ala Tyr Tyr Gln Ile His Leu Ile Tyr Thr Leu Pro
 1               5                   10                  15

Ile Leu Gly Leu Leu Gly Leu Leu Thr Ser Pro Ile Leu Thr Lys Phe
            20                  25                  30

Asp Ile Tyr Lys Ile Ser Ile Leu Val Phe Ile Ala Phe Ser Ala Thr
                35                  40                  45

Thr Pro Trp Asp Ser Trp Ile Ile Arg Asn Gly Ala Trp Thr Tyr Pro
    50                  55                  60

Ser Ala Glu Ser Gly Gln Gly Val Phe Gly Thr Phe Leu Asp Val Pro
65                  70                  75                  80

Tyr Glu Glu Tyr Ala Phe Phe Val Ile Gln Thr Val Ile Thr Gly Leu
                85                  90                  95

Val Tyr Val Leu Ala Thr Arg His Leu Leu Pro Ser Leu Ala Leu Pro
            100                 105                 110

Lys Thr Arg Ser Ser Ala Leu Ser Leu Ala Leu Lys Ala Leu Ile Pro
        115                 120                 125

Leu Pro Ile Ile Tyr Leu Phe Thr Ala His Pro Ser Pro Ser Pro Asp
    130                 135                 140

Pro Leu Val Thr Asp His Tyr Phe Tyr Met Arg Ala Leu Ser Leu Leu
145                 150                 155                 160

Ile Thr Pro Pro Thr Met Leu Leu Ala Ala Leu Ser Gly Glu Tyr Ala
                165                 170                 175

Phe Asp Trp Lys Ser Gly Arg Ala Lys Ser Thr Ile Ala Ala Ile Met
            180                 185                 190

Ile Pro Thr Val Tyr Leu Ile Trp Val Asp Tyr Val Ala Val Gly Gln
        195                 200                 205

Asp Ser Trp Ser Ile Asn Asp Glu Lys Ile Val Gly Trp Arg Leu Gly
    210                 215                 220

Gly Val Leu Pro Ile Glu Glu Ala Met Phe Phe Leu Leu Thr Asn Leu
225                 230                 235                 240

Met Ile Val Leu Gly Leu Ser Ala Cys Asp His Thr Gln Ala Leu Tyr
                245                 250                 255

Leu Leu His Gly Arg Thr Ile Tyr Gly Asn Lys Lys Met Pro Ser Ser
            260                 265                 270

Phe Pro Leu Ile Thr Pro Pro Val Leu Ser Leu Phe Ser Ser Arg
        275                 280                 285

Pro Tyr Ser Ser Gln Pro Lys Arg Asp Leu Glu Leu Ala Val Lys Leu
    290                 295                 300

Leu Glu Lys Lys Ser Arg Ser Phe Phe Val Ala Ser Ala Gly Phe Pro
305                 310                 315                 320

Ser Glu Val Arg Glu Arg Leu Val Gly Leu Tyr Ala Phe Cys Arg Val
                325                 330                 335

Thr Asp Asp Leu Ile Asp Ser Pro Glu Val Ser Ser Asn Pro His Ala
            340                 345                 350

Thr Ile Asp Met Val Ser Asp Phe Leu Thr Leu Leu Phe Gly Pro Pro
        355                 360                 365

Leu His Pro Ser Gln Pro Asp Lys Ile Leu Ser Ser Pro Leu Leu Pro
    370                 375                 380

Pro Ser His Pro Ser Arg Pro Thr Gly Met Tyr Pro Leu Pro Pro Pro
385                 390                 395                 400
```

```
Pro Ser Leu Ser Pro Ala Glu Leu Val Gln Phe Leu Thr Glu Arg Val
                405                 410                 415
Pro Val Gln Tyr His Phe Ala Phe Arg Leu Leu Ala Lys Leu Gln Gly
                420                 425                 430
Leu Ile Pro Arg Tyr Pro Leu Asp Glu Leu Leu Arg Gly Tyr Thr Thr
                435                 440                 445
Asp Leu Ile Phe Pro Leu Ser Thr Glu Ala Val Gln Ala Arg Lys Thr
    450                 455                 460
Pro Ile Glu Thr Thr Ala Asp Leu Leu Asp Tyr Gly Leu Cys Val Ala
465                 470                 475                 480
Gly Ser Val Ala Glu Leu Leu Val Tyr Val Ser Trp Ala Ser Ala Pro
                485                 490                 495
Ser Gln Val Pro Ala Thr Ile Glu Glu Arg Glu Ala Val Leu Val Ala
                500                 505                 510
Ser Arg Glu Met Gly Thr Ala Leu Gln Leu Val Asn Ile Ala Arg Asp
                515                 520                 525
Ile Lys Gly Asp Ala Thr Glu Gly Arg Phe Tyr Leu Pro Leu Ser Phe
    530                 535                 540
Phe Gly Leu Arg Asp Glu Ser Lys Leu Ala Ile Pro Thr Asp Trp Thr
545                 550                 555                 560
Glu Pro Arg Pro Gln Asp Phe Asp Lys Leu Leu Ser Leu Ser Pro Ser
                565                 570                 575
Ser Thr Leu Pro Ser Ser Asn Ala Ser Glu Ser Phe Arg Phe Glu Trp
                580                 585                 590
Lys Thr Tyr Ser Leu Pro Leu Val Ala Tyr Ala Glu Asp Leu Ala Lys
                595                 600                 605
His Ser Tyr Lys Gly Ile Asp Arg Leu Pro Thr Glu Val Gln Ala Gly
    610                 615                 620
Met Arg Ala Ala Cys Ala Ser Tyr Leu Leu Ile Gly Arg Glu Ile Lys
625                 630                 635                 640
Val Val Trp Lys Gly Asp Val Gly Glu Arg Arg Thr Val Ala Gly Trp
                645                 650                 655
Arg Arg Val Arg Lys Val Leu Ser Val Val Met Ser Gly Trp Glu Gly
                660                 665                 670
Gln
```

(2) INFORMATION FOR SEQ ID NO:20:

(i) SEQUENCE CHARACTERISTICS:
        (A) LENGTH: 1165 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 141..896
        (D) OTHER INFORMATION: /product= "PRidi"

(xi) SEQUENCE DESCRIPTION: SEQ ID NO:20:

```
CTTCTCTTTC CTCGACCTCT TCGGCAGGCC GTTGAAGACT CGTTTACTCA TACCCCACAT     60
```

-continued

```
CTCGCATATA TCACTTTCCT CCTTCCAGAA CAAGTTCTGA GTCAACCGAA AGAAAGAAG        120

GCAGAAGAAA TATATTCTAG ATG TCC ATG CCC AAC ATT GTT CCC CCC GCC           170
                     Met Ser Met Pro Asn Ile Val Pro Pro Ala
                       1           5                      10

GAG GTC CGA ACC GAA GGA CTC AGT TTA GAA GAG TAC GAT GAG GAG CAG         218
Glu Val Arg Thr Glu Gly Leu Ser Leu Glu Glu Tyr Asp Glu Glu Gln
             15                  20                  25

GTC AGG CTG ATG GAG GAG CGA TGT ATT CTT GTT AAC CCG GAC GAT GTG         266
Val Arg Leu Met Glu Glu Arg Cys Ile Leu Val Asn Pro Asp Asp Val
         30                  35                  40

GCC TAT GGA GAG GCT TCG AAA AAG ACC TGC CAC TTG ATG TCC AAC ATC         314
Ala Tyr Gly Glu Ala Ser Lys Lys Thr Cys His Leu Met Ser Asn Ile
     45                  50                  55

AAC GCG CCC AAG GAC CTC CTC CAC CGA GCA TTC TCC GTG TTT CTC TTC         362
Asn Ala Pro Lys Asp Leu Leu His Arg Ala Phe Ser Val Phe Leu Phe
 60                  65                  70

CGC CCA TCG GAC GGA GCA CTC CTG CTT CAG CGA AGA GCG GAC GAG AAG         410
Arg Pro Ser Asp Gly Ala Leu Leu Leu Gln Arg Arg Ala Asp Glu Lys
 75                  80                  85                  90

ATT ACG TTC CCT GGA ATG TGG ACC AAC ACG TGT TGC AGT CAT CCT TTG         458
Ile Thr Phe Pro Gly Met Trp Thr Asn Thr Cys Cys Ser His Pro Leu
                 95                 100                 105

AGC ATC AAG GGC GAG GTT GAA GAG GAG AAC CAG ATC GGT GTT CGA CGA         506
Ser Ile Lys Gly Glu Val Glu Glu Glu Asn Gln Ile Gly Val Arg Arg
            110                 115                 120

GCT GCG TCC CGA AAG TTG GAG CAC GAG CTT GGC GTG CCT ACA TCG TCG         554
Ala Ala Ser Arg Lys Leu Glu His Glu Leu Gly Val Pro Thr Ser Ser
        125                 130                 135

ACT CCG CCC GAC TCG TTC ACC TAC CTC ACT AGG ATA CAT TAC CTC GCT         602
Thr Pro Pro Asp Ser Phe Thr Tyr Leu Thr Arg Ile His Tyr Leu Ala
    140                 145                 150

CCG AGT GAC GGA CTC TGG GGA GAA CAC GAG ATC GAC TAC ATT CTC TTC         650
Pro Ser Asp Gly Leu Trp Gly Glu His Glu Ile Asp Tyr Ile Leu Phe
155                 160                 165                 170

TCA ACC ACA CCT ACA GAA CAC ACT GGA AAC CCT AAC GAA GTC TCT GAC         698
Ser Thr Thr Pro Thr Glu His Thr Gly Asn Pro Asn Glu Val Ser Asp
                175                 180                 185

ACT CGA TAT GTC ACC AAG CCC GAG CTC CAG GCG ATG TTT GAG GAC GAG         746
Thr Arg Tyr Val Thr Lys Pro Glu Leu Gln Ala Met Phe Glu Asp Glu
            190                 195                 200

TCT AAC TCA TTT ACC CCT TGG TTC AAA TTG ATT GCC CGA GAC TTC CTG         794
Ser Asn Ser Phe Thr Pro Trp Phe Lys Leu Ile Ala Arg Asp Phe Leu
        205                 210                 215

TTT GGC TGG TGG GAT CAA CTT CTC GCC AGA CGA AAT GAA AAG GGT GAG         842
Phe Gly Trp Trp Asp Gln Leu Leu Ala Arg Arg Asn Glu Lys Gly Glu
    220                 225                 230

GTC GAT GCC AAA TCG TTG GAG GAT CTC TCG GAC AAC AAA GTC TGG AAG         890
Val Asp Ala Lys Ser Leu Glu Asp Leu Ser Asp Asn Lys Val Trp Lys
235                 240                 245                 250

ATG TAGTCGACCC TTCTTTCTGT ACAGTCATCT CAGTTCGCCT GTTGGTTGCT              943
Met

TGCTTCTTGC TCTTCTTTCT ATATATCTTT TTTCTTGCCT GGGTAGACTT GATCTTTCTA      1003

CATAGCATAC GCATACATAC ATAAACTCTA TTTCTTGTTC TTTATCTCTC TTCTAAGGGA      1063

ATCTTCAAGA TCAATTTCTT TTTGGGCTAC AACATTTCAG ATCAATATTG CTTTTCAGAC      1123

TACAAAAAAA AAAAAAAAAA ACTCGAGGGG GGGCCCGGTA CC                         1165
```

(2) INFORMATION FOR SEQ ID NO:21:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ser Met Pro Asn Ile Val Pro Pro Ala Glu Val Arg Thr Glu Gly
  1               5                  10                  15

Leu Ser Leu Glu Glu Tyr Asp Glu Glu Gln Val Arg Leu Met Glu Glu
                 20                  25                  30

Arg Cys Ile Leu Val Asn Pro Asp Asp Val Ala Tyr Gly Glu Ala Ser
             35                  40                  45

Lys Lys Thr Cys His Leu Met Ser Asn Ile Asn Ala Pro Lys Asp Leu
         50                  55                  60

Leu His Arg Ala Phe Ser Val Phe Leu Phe Arg Pro Ser Asp Gly Ala
 65                  70                  75                  80

Leu Leu Leu Gln Arg Arg Ala Asp Glu Lys Ile Thr Phe Pro Gly Met
                 85                  90                  95

Trp Thr Asn Thr Cys Cys Ser His Pro Leu Ser Ile Lys Gly Glu Val
                100                 105                 110

Glu Glu Glu Asn Gln Ile Gly Val Arg Arg Ala Ala Ser Arg Lys Leu
                115                 120                 125

Glu His Glu Leu Gly Val Pro Thr Ser Ser Thr Pro Pro Asp Ser Phe
130                 135                 140

Thr Tyr Leu Thr Arg Ile His Tyr Leu Ala Pro Ser Asp Gly Leu Trp
145                 150                 155                 160

Gly Glu His Glu Ile Asp Tyr Ile Leu Phe Ser Thr Thr Pro Thr Glu
                165                 170                 175

His Thr Gly Asn Pro Asn Glu Val Ser Asp Thr Arg Tyr Val Thr Lys
                180                 185                 190

Pro Glu Leu Gln Ala Met Phe Glu Asp Glu Ser Asn Ser Phe Thr Pro
                195                 200                 205

Trp Phe Lys Leu Ile Ala Arg Asp Phe Leu Phe Gly Trp Trp Asp Gln
210                 215                 220

Leu Leu Ala Arg Arg Asn Glu Lys Gly Val Asp Ala Lys Ser Leu
225                 230                 235                 240

Glu Asp Leu Ser Asp Asn Lys Val Trp Lys Met
                245                 250
```

(2) INFORMATION FOR SEQ ID NO:22:

(i) SEQUENCE CHARACTERISTICS:
        (A) LENGTH: 3550 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phaffia rhodozyma
        (B) STRAIN: CBS 6938

```
    (ix) FEATURE:
         (A) NAME/KEY: exon
         (B) LOCATION: 941..966

(ix) FEATURE:
         (A) NAME/KEY: intron
         (B) LOCATION: 967..1077

(ix) FEATURE:
         (A) NAME/KEY: exon
         (B) LOCATION: 1078..1284

(ix) FEATURE:
         (A) NAME/KEY: intron
         (B) LOCATION: 1285..1364

(ix) FEATURE:
         (A) NAME/KEY: exon
         (B) LOCATION: 1365..1877

(ix) FEATURE:
         (A) NAME/KEY: intron
         (B) LOCATION: 1878..1959

(ix) FEATURE:
         (A) NAME/KEY: exon
         (B) LOCATION: 1960..2202

(ix) FEATURE:
         (A) NAME/KEY: intron
         (B) LOCATION: 2203..2292

(ix) FEATURE:
         (A) NAME/KEY: exon
         (B) LOCATION: 2293..3325

(ix) FEATURE:
         (A) NAME/KEY: CDS
         (B) LOCATION: join(941..966, 1078..1284, 1365..1877, 1960..2202,
             2293..3325)
         (D) OTHER INFORMATION: /product= "PRGcrtB GB"

(xi) SEQUENCE DESCRIPTION: SEQ ID NO:22:

GGAATTCCAG TTTTGCCTTT GACGAGAAAG GACACTGGGT TGGAAAGAGA AGATGGTACG      60

TTCTTCTCCA CCTTGAATGT GTTGCTTACT AGACATGTTT GACACGCTAA TGCATTTCTT     120

TCCACTTTGA CTTTTGAACT ATGGTGGTTG GGCGATCCCC AAAATCATTA GCTTCTACTT     180

CAGCTCATTA CCTCGATCTC ATCTTACTAC CAGGTGTTGC ATTCTCACCT ACGGCCTCTT     240

CTTTGTTCTC TCGACTGGGC CATGGAAAAG GATATTACGA TAAATACATC ACTCAGTATC     300

GGTCGATCTG TGCAGGCAAG AATCGACCCG TCCGAAGCTG AGTACGCGTC TTCTCTTTTC     360

TCGATACCCA ACGGACGCTA TTTTGTGACA GAAGGATGAG ACTATCCAAC AGCTCAAACA     420

AACTAACGCT CTTGATTAAT CACCCGCTCA ACTTATTGCT CAACTCAGTT GGACTGGCGC     480

TGAAAGAACA GTTCTTAGAC AAAAACATGG TCCCTATAGG AGAATGGGAT GCGAATCTGG     540

ATGAAGTGTT GGTTGGAGAT CACGTGAGGA CATTATCCGA GGACAATTAA CTACTTAAGA     600

TATATACATG ATTTATGTCG ATCGGCATCC AGCCGGGGAT TGATCGGCTG ATGGCCGGAA     660

ATGTGATGAT GGTCGAAACT CGATCTCTCT TTTTTTGTTC ATCTTCTCAT CCCTCTTCTC     720

TCTTTCTACT GACATCCATC TCCAACTGTC TAGATCAGTT CGGAAACAAG AAGTGGACAC     780

AGAGAGATCT TTGCTGAAGA GTTGTATTCC AGAAAGGGAA AACAAAGGAA AGAAGCGCCG     840

AAGCACATCA CCAACTTCAG CAAGCCGGTC CAGCCCGATC TCGGATAGAC ATCATCTTAC     900

CCAACTCGTA TCATCCCCAA CAGATAGAGT TTTTGTCGCA ATG ACG GCT CTC GCA     955
                                                Met Thr Ala Leu Ala
                                                 1               5
```

```
TAT TAC CAG AT  GTTTGTCTCC ATACCTCTTC TTCGTTTTGC ACACCACTCA        1006
Tyr Tyr Gln Ile
TGTGTGCATA TGTGTGTGCG TCCTTCCAAA TCTTTCAATG ACTAACATCT TTACCGTGCT   1066
CTTCTTCTTA G C CAT CTG ATC TAT ACT CTC CCA ATT CTT GGT CTT CTC     1114
             His Leu Ile Tyr Thr Leu Pro Ile Leu Gly Leu Leu
                      10              15              20
GGC CTG CTC ACT TCC CCG ATT TTG ACA AAA TTT GAC ATC TAC AAA ATA    1162
Gly Leu Leu Thr Ser Pro Ile Leu Thr Lys Phe Asp Ile Tyr Lys Ile
             25              30              35
TCG ATC CTC GTA TTT ATT GCG TTT AGT GCA ACC ACA CCA TGG GAC TCA    1210
Ser Ile Leu Val Phe Ile Ala Phe Ser Ala Thr Thr Pro Trp Asp Ser
         40              45              50
TGG ATC ATC AGA AAT GGC GCA TGG ACA TAT CCA TCA GCG GAG AGT GGC    1258
Trp Ile Ile Arg Asn Gly Ala Trp Thr Tyr Pro Ser Ala Glu Ser Gly
     55              60              65
CAA GGC GTG TTT GGA ACG TTT CTA GA  GTTAGTCGAC CGTTAATACT          1304
Gln Gly Val Phe Gly Thr Phe Leu Asp
 70              75
CTTAGCCGCG CGTCGTTTCC GCGATTACAT TTAACATCTG AATTTATCCC TGATCAACAG  1364
T GTT CCA TAT GAA GAG TAC GCT TTC TTT GTC ATT CAA ACC GTA ATC      1410
  Val Pro Tyr Glu Glu Tyr Ala Phe Phe Val Ile Gln Thr Val Ile
           80              85              90
ACC GGC TTG GTC TAC GTC TTG GCA ACT AGG CAC CTT CTC CCA TCT CTC    1458
Thr Gly Leu Val Tyr Val Leu Ala Thr Arg His Leu Leu Pro Ser Leu
         95              100             105
GCG CTT CCC AAG ACT AGA TCG TCC GCC CTT TCT CTC GCG CTC AAG GCG    1506
Ala Leu Pro Lys Thr Arg Ser Ser Ala Leu Ser Leu Ala Leu Lys Ala
110             115             120             125
CTC ATC CCT CTG CCC ATT ATC TAC CTA TTT ACC GCT CAC CCC AGC CCA    1554
Leu Ile Pro Leu Pro Ile Ile Tyr Leu Phe Thr Ala His Pro Ser Pro
                 130             135             140
TCG CCC GAC CCG CTC GTG ACA GAT CAC TAC TTC TAC ATG CGG GCA CTC    1602
Ser Pro Asp Pro Leu Val Thr Asp His Tyr Phe Tyr Met Arg Ala Leu
             145             150             155
TCC TTA CTC ATC ACC CCA CCT ACC ATG CTC TTG GCA GCA TTA TCA GGC    1650
Ser Leu Leu Ile Thr Pro Pro Thr Met Leu Leu Ala Ala Leu Ser Gly
         160             165             170
GAA TAT GCT TTC GAT TGG AAA AGT GGC CGA GCA AAG TCA ACT ATT GCA    1698
Glu Tyr Ala Phe Asp Trp Lys Ser Gly Arg Ala Lys Ser Thr Ile Ala
     175             180             185
GCA ATC ATG ATC CCG ACG GTG TAT CTG ATT TGG GTA GAT TAT GTT GCT    1746
Ala Ile Met Ile Pro Thr Val Tyr Leu Ile Trp Val Asp Tyr Val Ala
190             195             200             205
GTC GGT CAA GAC TCT TGG TCG ATC AAC GAT GAG AAG ATT GTA GGG TGG    1794
Val Gly Gln Asp Ser Trp Ser Ile Asn Asp Glu Lys Ile Val Gly Trp
                 210             215             220
AGG CTT GGA GGT GTA CTA CCC ATT GAG GAA GCT ATG TTC TTC TTA CTG    1842
Arg Leu Gly Gly Val Leu Pro Ile Glu Glu Ala Met Phe Phe Leu Leu
             225             230             235
ACG AAT CTA ATG ATT GTT CTG GGT CTG TCT GCC    TG  GTAAGTTGAT      1887
Thr Asn Leu Met Ile Val Leu Gly Leu Ser Ala  Cys
         240             245
CTCATCCTCT CTTCCTTTGG TGAAAAAAGC TGTTTGGCTG ATTGCTGCGA ACTCACCCAT  1947
CGGAATCTGT AG C GAT CAT ACT CAG GCC CTA TAC CTG CTA CAC GGT CGA   1996
                Asp His Thr Gln Ala Leu Tyr Leu Leu His Gly Arg
                         250             255             260
```

-continued

```
ACT ATT TAT GGC AAC AAA AAG ATG CCA TCT TCA TTT CCC CTC ATT ACA          2044
Thr Ile Tyr Gly Asn Lys Lys Met Pro Ser Ser Phe Pro Leu Ile Thr
            265                 270                 275

CCG CCT GTG CTC TCC CTG TTT TTT AGC AGC CGA CCA TAC TCT TCT CAG          2092
Pro Pro Val Leu Ser Leu Phe Phe Ser Ser Arg Pro Tyr Ser Ser Gln
        280                 285                 290

CCA AAA CGT GAC TTG GAA CTG GCA GTC AAG TTG TTG GAG AAA AAG AGC          2140
Pro Lys Arg Asp Leu Glu Leu Ala Val Lys Leu Leu Glu Lys Lys Ser
295                 300                 305

CGG AGC TTT TTT GTT GCC TCG GCT GGA TTT CCT AGC GAA GTT AGG GAG          2188
Arg Ser Phe Phe Val Ala Ser Ala Gly Phe Pro Ser Glu Val Arg Glu
310                 315                 320                 325

AGG CTG GTT GGA CT  GTGAGCACGC ATTCTTTAGG TTTGTTCGGT CTTTCACCTT          2242
Arg Leu Val Gly Leu
                330

CATGTGCATT CGCTGATCAG TTTTCTTGGT GATCCGGGAC CTGCATACAG A TAC GCA         2299
                                                         Tyr Ala
TTC TGC CGG GTG ACT GAT GAT CTT ATC GAC TCT CCT GAA GTA TCT TCC          2347
Phe Cys Arg Val Thr Asp Asp Leu Ile Asp Ser Pro Glu Val Ser Ser
            335                 340                 345

AAC CCG CAT GCC ACA ATT GAC ATG GTC TCC GAT TTT CTT ACC CTA CTA          2395
Asn Pro His Ala Thr Ile Asp Met Val Ser Asp Phe Leu Thr Leu Leu
        350                 355                 360

TTT GGG CCC CCG CTA CAC CCT TCG CAA CCT GAC AAG ATC CTT TCT TCG          2443
Phe Gly Pro Pro Leu His Pro Ser Gln Pro Asp Lys Ile Leu Ser Ser
365                 370                 375                 380

CCT TTA CTT CCT CCT TCG CAC CCT TCC CGA CCC ACG GGA ATG TAT CCC          2491
Pro Leu Leu Pro Pro Ser His Pro Ser Arg Pro Thr Gly Met Tyr Pro
            385                 390                 395

CTC CCG CCT CCT CCT TCG CTC TCG CCT GCC GAG CTC GTT CAA TTC CTT          2539
Leu Pro Pro Pro Pro Ser Leu Ser Pro Ala Glu Leu Val Gln Phe Leu
        400                 405                 410

ACC GAA AGG GTT CCC GTT CAA TAC CAT TTC GCC TTC AGG TTG CTC GCT          2587
Thr Glu Arg Val Pro Val Gln Tyr His Phe Ala Phe Arg Leu Leu Ala
            415                 420                 425

AAG TTG CAA GGG CTG ATC CCT CGA TAC CCA CTC GAC GAA CTC CTT AGA          2635
Lys Leu Gln Gly Leu Ile Pro Arg Tyr Pro Leu Asp Glu Leu Leu Arg
        430                 435                 440

GGA TAC ACC ACT GAT CTT ATC TTT CCC TTA TCG ACA GAG GCA GTC CAG          2683
Gly Tyr Thr Thr Asp Leu Ile Phe Pro Leu Ser Thr Glu Ala Val Gln
445                 450                 455                 460

GCT CGG AAG ACG CCT ATC GAG ACC ACA GCT GAC TTG CTG GAC TAT GGT          2731
Ala Arg Lys Thr Pro Ile Glu Thr Thr Ala Asp Leu Leu Asp Tyr Gly
            465                 470                 475

CTA TGT GTA GCA GGC TCA GTC GCC GAG CTA TTG GTC TAT GTC TCT TGG          2779
Leu Cys Val Ala Gly Ser Val Ala Glu Leu Leu Val Tyr Val Ser Trp
        480                 485                 490

GCA AGT GCA CCA AGT CAG GTC CCT GCC ACC ATA GAA GAA AGA GAA GCT          2827
Ala Ser Ala Pro Ser Gln Val Pro Ala Thr Ile Glu Glu Arg Glu Ala
            495                 500                 505

GTG TTA GTG GCA AGC CGA GAG ATG GGA ACT GCC CTT CAG TTG GTG AAC          2875
Val Leu Val Ala Ser Arg Glu Met Gly Thr Ala Leu Gln Leu Val Asn
510                 515                 520

ATT GCT AGG GAC ATT AAA GGG GAC GCA ACA GAA GGG AGA TTT TAC CTA          2923
Ile Ala Arg Asp Ile Lys Gly Asp Ala Thr Glu Gly Arg Phe Tyr Leu
525                 530                 535                 540

CCA CTC TCA TTC TTT GGT CTT CGG GAT GAA TCA AAG CTT GCG ATC CCG          2971
Pro Leu Ser Phe Phe Gly Leu Arg Asp Glu Ser Lys Leu Ala Ile Pro
            545                 550                 555
```

```
ACT GAT TGG ACG GAA CCT CGG CCT CAA GAT TTC GAC AAA CTC CTC AGT     3019
Thr Asp Trp Thr Glu Pro Arg Pro Gln Asp Phe Asp Lys Leu Leu Ser
            560                 565                 570

CTA TCT CCT TCG TCC ACA TTA CCA TCT TCA AAC GCC TCA GAA AGC TTC     3067
Leu Ser Pro Ser Ser Thr Leu Pro Ser Ser Asn Ala Ser Glu Ser Phe
            575                 580                 585

CGG TTC GAA TGG AAG ACG TAC TCG CTT CCA TTA GTC GCC TAC GCA GAG     3115
Arg Phe Glu Trp Lys Thr Tyr Ser Leu Pro Leu Val Ala Tyr Ala Glu
            590                 595                 600

GAT CTT GCC AAA CAT TCT TAT AAG GGA ATT GAC CGA CTT CCT ACC GAG     3163
Asp Leu Ala Lys His Ser Tyr Lys Gly Ile Asp Arg Leu Pro Thr Glu
605                 610                 615                 620

GTT CAA GCG GGA ATG CGA GCG GCT TGC GCG AGC TAC CTA CTG ATC GGC     3211
Val Gln Ala Gly Met Arg Ala Ala Cys Ala Ser Tyr Leu Leu Ile Gly
                625                 630                 635

CGA GAG ATC AAA GTC GTT TGG AAA GGA GAC GTC GGA GAG AGA AGG ACA     3259
Arg Glu Ile Lys Val Val Trp Lys Gly Asp Val Gly Glu Arg Arg Thr
            640                 645                 650

GTT GCC GGA TGG AGG AGA GTA CGG AAA GTC TTG AGT GTG GTC ATG AGC     3307
Val Ala Gly Trp Arg Arg Val Arg Lys Val Leu Ser Val Val Met Ser
            655                 660                 665

GGA TGG GAA GGG CAG TAAGACAGCG GAAGAATACC GACAGACAAT GATGAGTGAG     3362
Gly Trp Glu Gly Gln
    670

AATAAAATCA TCCTCAATCT TCTTTCTCTA GGTGCTCTTT TTTGTTTTCT ATTATGACCA    3422

ACTCTAAAGG AACTGGCCTT GCAGATATTT CTCTTCCCCC CATCTTCCTC CTTTCCATCG    3482

TTTGTTCTTT CCATTTTTGT CGGTTTACTA TGTCAATTCT TTTTCTTGCT TTTTCTTATC    3542

AATCTAGA                                                             3550

(2) INFORMATION FOR SEQ ID NO:23:

(i) SEQUENCE CHARACTERISTICS:
        (A) LENGTH: 673 amino acids
        (B) TYPE: amino acid
        (D) TOPOLOGY: linear (ii) MOLECULE TYPE: protein (xi) SEQUENCE DESCRIPTION: SEQ ID NO:23:

Met Thr Ala Leu Ala Tyr Tyr Gln Ile His Leu Ile Tyr Thr Leu Pro
 1               5                  10                  15

Ile Leu Gly Leu Leu Gly Leu Leu Thr Ser Pro Ile Leu Thr Lys Phe
                20                  25                  30

Asp Ile Tyr Lys Ile Ser Ile Leu Val Phe Ile Ala Phe Ser Ala Thr
            35                  40                  45

Thr Pro Trp Asp Ser Trp Ile Ile Arg Asn Gly Ala Trp Thr Tyr Pro
        50                  55                  60

Ser Ala Glu Ser Gly Gln Gly Val Phe Gly Thr Phe Leu Asp Val Pro
65                  70                  75                  80

Tyr Glu Glu Tyr Ala Phe Phe Val Ile Gln Thr Val Ile Thr Gly Leu
                85                  90                  95

Val Tyr Val Leu Ala Thr Arg His Leu Leu Pro Ser Leu Ala Leu Pro
                100                 105                 110

Lys Thr Arg Ser Ser Ala Leu Ser Leu Ala Leu Lys Ala Leu Ile Pro
            115                 120                 125

Leu Pro Ile Ile Tyr Leu Phe Thr Ala His Pro Ser Pro Ser Pro Asp
        130                 135                 140
```

-continued

```
Pro Leu Val Thr Asp His Tyr Phe Tyr Met Arg Ala Leu Ser Leu Leu
145                 150                 155                 160

Ile Thr Pro Pro Thr Met Leu Leu Ala Ala Leu Ser Gly Glu Tyr Ala
            165                 170                 175

Phe Asp Trp Lys Ser Gly Arg Ala Lys Ser Thr Ile Ala Ala Ile Met
            180                 185                 190

Ile Pro Thr Val Tyr Leu Ile Trp Val Asp Tyr Val Ala Val Gly Gln
            195                 200                 205

Asp Ser Trp Ser Ile Asn Asp Glu Lys Ile Val Gly Trp Arg Leu Gly
            210                 215                 220

Gly Val Leu Pro Ile Glu Glu Ala Met Phe Phe Leu Leu Thr Asn Leu
225                 230                 235                 240

Met Ile Val Leu Gly Leu Ser Ala Cys Asp His Thr Gln Ala Leu Tyr
                245                 250                 255

Leu Leu His Gly Arg Thr Ile Tyr Gly Asn Lys Lys Met Pro Ser Ser
                260                 265                 270

Phe Pro Leu Ile Thr Pro Pro Val Leu Ser Leu Phe Phe Ser Ser Arg
                275                 280                 285

Pro Tyr Ser Ser Gln Pro Lys Arg Asp Leu Glu Leu Ala Val Lys Leu
                290                 295                 300

Leu Glu Lys Lys Ser Arg Ser Phe Phe Val Ala Ser Ala Gly Phe Pro
305                 310                 315                 320

Ser Glu Val Arg Glu Arg Leu Val Gly Leu Tyr Ala Phe Cys Arg Val
                325                 330                 335

Thr Asp Asp Leu Ile Asp Ser Pro Glu Val Ser Ser Asn Pro His Ala
                340                 345                 350

Thr Ile Asp Met Val Ser Asp Phe Leu Thr Leu Leu Phe Gly Pro Pro
                355                 360                 365

Leu His Pro Ser Gln Pro Asp Lys Ile Leu Ser Ser Pro Leu Leu Pro
                370                 375                 380

Pro Ser His Pro Ser Arg Pro Thr Gly Met Tyr Pro Leu Pro Pro Pro
385                 390                 395                 400

Pro Ser Leu Ser Pro Ala Glu Leu Val Gln Phe Leu Thr Glu Arg Val
                405                 410                 415

Pro Val Gln Tyr His Phe Ala Phe Arg Leu Leu Ala Lys Leu Gln Gly
                420                 425                 430

Leu Ile Pro Arg Tyr Pro Leu Asp Glu Leu Leu Arg Gly Tyr Thr Thr
                435                 440                 445

Asp Leu Ile Phe Pro Leu Ser Thr Glu Ala Val Gln Ala Arg Lys Thr
450                 455                 460

Pro Ile Glu Thr Thr Ala Asp Leu Leu Asp Tyr Gly Leu Cys Val Ala
465                 470                 475                 480

Gly Ser Val Ala Glu Leu Leu Val Tyr Val Ser Trp Ala Ser Ala Pro
                485                 490                 495

Ser Gln Val Pro Ala Thr Ile Glu Glu Arg Glu Ala Val Leu Val Ala
                500                 505                 510

Ser Arg Glu Met Gly Thr Ala Leu Gln Leu Val Asn Ile Ala Arg Asp
                515                 520                 525

Ile Lys Gly Asp Ala Thr Glu Gly Arg Phe Tyr Leu Pro Leu Ser Phe
                530                 535                 540

Phe Gly Leu Arg Asp Glu Ser Lys Leu Ala Ile Pro Thr Asp Trp Thr
545                 550                 555                 560
```

-continued

```
Glu Pro Arg Pro Gln Asp Phe Asp Lys Leu Leu Ser Leu Ser Pro Ser
                565                 570                 575

Ser Thr Leu Pro Ser Ser Asn Ala Ser Glu Ser Phe Arg Phe Glu Trp
            580                 585                 590

Lys Thr Tyr Ser Leu Pro Leu Val Ala Tyr Ala Glu Asp Leu Ala Lys
        595                 600                 605

Ser Tyr Lys Gly Ile Asp Arg Leu Pro Thr Glu Val Gln Ala Gly Met
    610                 615                 620

His Arg Ala Ala Cys Ala Ser Tyr Leu Leu Ile Gly Arg Glu Ile Lys
625                 630                 635                 640

Val Val Trp Lys Gly Asp Val Gly Glu Arg Arg Thr Val Ala Gly Trp
                645                 650                 655

Arg Arg Val Arg Lys Val Leu Ser Val Val Met Ser Gly Trp Glu Gly
                660                 665                 670

Gln

673
```

(2) INFORMATION FOR SEQ ID NO:24:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 24..500
        (D) OTHER INFORMATION: /product= "PRcDNA10"

(xi) SEQUENCE DESCRIPTION: SEQ ID NO:24:

```
AACACTTGGT TAGTTTCGAC GAC ATG CAG ATC TTC GTA AAG ACC CTC ACG         50
                        Met Gln Ile Phe Val Lys Thr Leu Thr
                         1               5

GGT AAG ACC ATC ACC CTT GAG GTG GAG TCT TCT GAC ACC ATC GAC AAC       98
Gly Lys Thr Ile Thr Leu Glu Val Glu Ser Ser Asp Thr Ile Asp Asn
 10              15                  20                  25

GTC AAG GCC AAG ATC CAG GAC AAG GAA GGA ATT CCC CCT GAT CAG CAG      146
Val Lys Ala Lys Ile Gln Asp Lys Glu Gly Ile Pro Pro Asp Gln Gln
                 30                  35                  40

CGA CTT ATC TTC GCC GGT AAG CAG CTC GAG GAT GGC CGA ACC CTT TCG      194
Arg Leu Ile Phe Ala Gly Lys Gln Leu Glu Asp Gly Arg Thr Leu Ser
             45                  50                  55

GAT TAC AAC ATC CAG AAA GAG TCC ACC CTC CAC CTC GTC CTT AGG TTG      242
Asp Tyr Asn Ile Gln Lys Glu Ser Thr Leu His Leu Val Leu Arg Leu
         60                  65                  70

CGA GGA GGA GCC AAG AAG CGA AAG AAG AAG CAG TAC ACT ACC CCC AAG      290
Arg Gly Gly Ala Lys Lys Arg Lys Lys Lys Gln Tyr Thr Thr Pro Lys
     75                  80                  85

AAG ATC AAG CAC AAG CGA AAG AAG GTC AAG ATG GCT ATT CTT AAG TAC      338
Lys Ile Lys His Lys Arg Lys Lys Val Lys Met Ala Ile Leu Lys Tyr
 90                  95                 100                 105
```

```
TAC AAG GTC GAC TCT GAT GGA AAG ATC AAG CGA CTT CGT CGA GAG TGC        386
Tyr Lys Val Asp Ser Asp Gly Lys Ile Lys Arg Leu Arg Arg Glu Cys
            110                 115                 120

CCC CAG CCC CAG TGC GGA GCT GGT ATC TTC ATG GCT TTC CAC TCC AAC        434
Pro Gln Pro Gln Cys Gly Ala Gly Ile Phe Met Ala Phe His Ser Asn
            125                 130                 135

CGA CAG ACT TGC GGA AAG TGT GGT CTT ACC TAC ACC TTC GCC GAG GGA        482
Arg Gln Thr Cys Gly Lys Cys Gly Leu Thr Tyr Thr Phe Ala Glu Gly
            140                 145                 150

ACC CAG CCC TCT GCT TAGATCATCA ATCGTTTGTT CCCGAGCGAT CTTTGAGTCT        537
Thr Gln Pro Ser Ala
    155

TTGTTACATT CTCAAAAAAA AAAAAAAAAA AAA                                   570
```

(2) INFORMATION FOR SEQ ID NO:25:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:25:

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Gln Tyr Thr Thr Pro Lys Lys Ile Lys His Lys Arg Lys
                85                  90                  95

Lys Val Lys Met Ala Ile Leu Lys Tyr Tyr Lys Val Asp Ser Asp Gly
            100                 105                 110

Lys Ile Lys Arg Leu Arg Arg Glu Cys Pro Gln Pro Gln Cys Gly Ala
        115                 120                 125

Gly Ile Phe Met Ala Phe His Ser Asn Arg Gln Thr Cys Gly Lys Cys
    130                 135                 140

Gly Leu Thr Tyr Thr Phe Ala Glu Gly Thr Gln Pro Ser Ala
145                 150                 155
```

(2) INFORMATION FOR SEQ ID NO:26:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
         (A) NAME/KEY: CDS
         (B) LOCATION: 57..278
         (D) OTHER INFORMATION: /product= "PRcDNA11"

(xi) SEQUENCE DESCRIPTION: SEQ ID NO:26:

```
TTTACACACA AACCTTACCT ACCTTTTCAA CAACAAATCA CACCTAAGCT TACATC         56

ATG GAG TCC ATC AAG ACC TCG ATT TCC AAC GCC GCC AAC TAC GCT TCT      104
Met Glu Ser Ile Lys Thr Ser Ile Ser Asn Ala Ala Asn Tyr Ala Ser
  1               5                  10                  15

GAG ACT GTC AAC CAG GCC ACT AGC GCC ACC TCC AAG GAG GCC AAC AAG      152
Glu Thr Val Asn Gln Ala Thr Ser Ala Thr Ser Lys Glu Ala Asn Lys
                 20                  25                  30

GAG GTT GCC AAG GAC TCC AAT GCC GGA GTT GGA ACC CGA ATC AAC GCC      200
Glu Val Ala Lys Asp Ser Asn Ala Gly Val Gly Thr Arg Ile Asn Ala
             35                  40                  45

GGA ATT GAT GCT CTT GGA GAC AAG GCC GAC GAG ACT TCG TCT GAT GCC      248
Gly Ile Asp Ala Leu Gly Asp Lys Ala Asp Glu Thr Ser Ser Asp Ala
 50                  55                  60

AAG TCC AAG GCC TAC AAG CAG AAC ATC TAAGTTATTT AGATAGTCGT            295
Lys Ser Lys Ala Tyr Lys Gln Asn Ile
 65                  70

CCATATTT                                                             303
```

(2) INFORMATION FOR SEQ ID NO:27:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO:27:

```
Met Glu Ser Ile Lys Thr Ser Ile Ser Asn Ala Ala Asn Tyr Ala Ser
  1               5                  10                  15

Glu Thr Val Asn Gln Ala Thr Ser Ala Thr Ser Lys Glu Ala Asn Lys
                 20                  25                  30

Glu Val Ala Lys Asp Ser Asn Ala Gly Val Gly Thr Arg Ile Asn Ala
             35                  40                  45

Gly Ile Asp Ala Leu Gly Asp Lys Ala Asp Glu Thr Ser Ser Asp Ala
 50                  55                  60

Lys Ser Lys Ala Tyr Lys Gln Asn Ile
 65                  70
```

(2) INFORMATION FOR SEQ ID NO:28:

(i) SEQUENCE CHARACTERISTICS:
        (A) LENGTH: 307 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Phaffia rhodozyma (ix) FEATURE:
              (A) NAME/KEY: CDS
              (B) LOCATION: 3..227
              (D) OTHER INFORMATION: /product= "PRcDNA18"

(xi) SEQUENCE DESCRIPTION: SEQ ID NO:28:

```
AC CCT TCC ATC GAG TCT GAG GCC CGA CAA CAC AAG CTC AAG AGG CTT         47
   Pro Ser Ile Glu Ser Glu Ala Arg Gln His Lys Leu Lys Arg Leu
    1               5                  10                  15

GTG CAG AGC CCC AAC TCT TTC TTC ATG GAC GTC AAG TGC CCT GGT TGC        95
Val Gln Ser Pro Asn Ser Phe Phe Met Asp Val Lys Cys Pro Gly Cys
                 20                  25                  30

TTC CAG ATC ACC ACC GTG TTC TCG CAC GCT TCC ACT GCC GTT CAG TGT       143
Phe Gln Ile Thr Thr Val Phe Ser His Ala Ser Thr Ala Val Gln Cys
             35                  40                  45

GGA TCG TGC CAG ACC ATC CTC TGC CAG CCC CGG GGA GGA AAG GCT CGA       191
Gly Ser Cys Gln Thr Ile Leu Cys Gln Pro Arg Gly Gly Lys Ala Arg
         50                  55                  60

CTT ACC GAG GGA TGC TCT TTC CGA CGA AAG AAC TAAGTTTCTG TTATCGGATG     244
Leu Thr Glu Gly Cys Ser Phe Arg Arg Lys Asn
     65                  70                  75

ATGCATTCAA ATAAAAGTCA AAAAAAAAAA AAAAAAAAAC TCGAGGGGGG GCCCGGTACC     304

CAA                                                                   307
```

(2) INFORMATION FOR SEQ ID NO:29:

(i) SEQUENCE CHARACTERISTICS:
              (A) LENGTH: 74 amino acids
              (B) TYPE: amino acid
              (D) TOPOLOGY: linear (ii) MOLECULE TYPE: protein (xi) SEQUENCE DESCRIPTION: SEQ ID NO:29:

```
Pro Ser Ile Glu Ser Glu Ala Arg Gln His Lys Leu Lys Arg Leu Val
 1               5                  10                  15

Gln Ser Pro Asn Ser Phe Phe Met Asp Val Lys Cys Pro Gly Cys Phe
             20                  25                  30

Gln Ile Thr Thr Val Phe Ser His Ala Ser Thr Ala Val Gln Cys Gly
         35                  40                  45

Ser Cys Gln Thr Ile Leu Cys Gln Pro Arg Gly Gly Lys Ala Arg Leu
     50                  55                  60

Thr Glu Gly Cys Ser Phe Arg Arg Lys Asn
 65                  70
```

(2) INFORMATION FOR SEQ ID NO:30:

(i) SEQUENCE CHARACTERISTICS:
              (A) LENGTH: 502 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (vi) ORIGINAL SOURCE:
              (A) ORGANISM: Phaffia rhodozyma -continued

```
    (ix) FEATURE:
         (A) NAME/KEY: CDS
         (B) LOCATION: 30..359
         (D) OTHER INFORMATION: /product= "PRcDNA35"

(xi) SEQUENCE DESCRIPTION: SEQ ID NO:30:

GTCAGCTCCG GCTTAAATCG ATTCGTACA ATG TCT GAA CTC GCC GCC TCC TAC        53
                                 Met Ser Glu Leu Ala Ala Ser Tyr
                                  1               5

GCC GCT CTT ATC CTC GCC GAC GAG GGT ATT GAG ATC ACC TCT GAG AAG       101
Ala Ala Leu Ile Leu Ala Asp Glu Gly Ile Glu Ile Thr Ser Glu Lys
         10                  15                  20

CTC GTC ACT CTC ACC ACC GCC GCC AAG GTT GAG CTT GAG CCC ATC TGG       149
Leu Val Thr Leu Thr Thr Ala Ala Lys Val Glu Leu Glu Pro Ile Trp
 25                  30                  35                  40

GCC ACT CTC CTT GCC AAG GCC CTC GAG GGA AAG AAC GTC AAG GAG TTG       197
Ala Thr Leu Leu Ala Lys Ala Leu Glu Gly Lys Asn Val Lys Glu Leu
                     45                  50                  55

CTT TCC AAC GTC GGA TCC GGA GCC GGA GGA GCT GCC CCC GCC GCC GCC       245
Leu Ser Asn Val Gly Ser Gly Ala Gly Gly Ala Ala Pro Ala Ala Ala
                 60                  65                  70

GTC GCC GGT GGA GCT TCC GCT GAC GCC TCT GCC CCC GCT GAG GAG AAG       293
Val Ala Gly Gly Ala Ser Ala Asp Ala Ser Ala Pro Ala Glu Glu Lys
             75                  80                  85

AAG GAG GAG AAG GCT GAG GAC AAG GAG GAG TCT GAC GAC GAC ATG GGT       341
Lys Glu Glu Lys Ala Glu Asp Lys Glu Glu Ser Asp Asp Asp Met Gly
         90                  95                 100

TTC GGA CTT TTC GAT TAAACTCCCT CGCCTAAAAA CCCTTTTCTT CAACCCCCTC       396
Phe Gly Leu Phe Asp
105

TCGTGGCATC GTTCACTCGA CCGCTGCGTT TGTTGTCCTT TCCTCACGAA TTTTGTCCTT     456

GTCTGGTTTC CCAATGGGAT NTCCTTGAAA TGANGTTTCC CAATTG                    502

(2) INFORMATION FOR SEQ ID NO:31:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:31:

Met Ser Glu Leu Ala Ala Ser Tyr Ala Ala Leu Ile Leu Ala Asp Glu
 1               5                  10                  15

Gly Ile Glu Ile Thr Ser Glu Lys Leu Val Thr Leu Thr Thr Ala Ala
             20                  25                  30

Lys Val Glu Leu Glu Pro Ile Trp Ala Thr Leu Leu Ala Lys Ala Leu
         35                  40                  45

Glu Gly Lys Asn Val Lys Glu Leu Leu Ser Asn Val Gly Ser Gly Ala
     50                  55                  60

Gly Gly Ala Ala Pro Ala Ala Ala Val Ala Gly Gly Ala Ser Ala Asp
 65                  70                  75                  80

Ala Ser Ala Pro Ala Glu Glu Lys Lys Glu Glu Lys Ala Glu Asp Lys
                 85                  90                  95

Glu Glu Ser Asp Asp Asp Met Gly Phe Gly Leu Phe Asp
            100                 105
```

(2) INFORMATION FOR SEQ ID NO:32:

(i) SEQUENCE CHARACTERISTICS:
        (A) LENGTH: 381 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 7..282
        (D) OTHER INFORMATION: /product= "PRcDNA38"

(xi) SEQUENCE DESCRIPTION: SEQ ID NO:32:

```
CTCAAG ATG ACC AAA GGT ACC TCC TCT TTC GGT AAG CGA CAC ACC AAG         48
       Met Thr Lys Gly Thr Ser Ser Phe Gly Lys Arg His Thr Lys
       1               5                   10

ACC CAC ACC ATC TGC CGA CGA TGT GGT AAC AGG GCT TTC CAC AGG CAG        96
Thr His Thr Ile Cys Arg Arg Cys Gly Asn Arg Ala Phe His Arg Gln
15              20                  25                  30

AAG AAG ACC TGT GCC CAG TGT GGA TAC CCT GCC GCC AAG ATG CGA AGC       144
Lys Lys Thr Cys Ala Gln Cys Gly Tyr Pro Ala Ala Lys Met Arg Ser
            35                  40                  45

TTC AAC TGG GGA GAG AAG GCC AAG AGG AGA AAG ACC ACC GGT ACC GGT       192
Phe Asn Trp Gly Glu Lys Ala Lys Arg Arg Lys Thr Thr Gly Thr Gly
        50                  55                  60

CGA ATG CAG CAC CTC AAG GAC GTC TCT CGA CGA TTC AAG AAC GGC TTC       240
Arg Met Gln His Leu Lys Asp Val Ser Arg Arg Phe Lys Asn Gly Phe
    65                  70                  75

CGA GAG GGA ACT TCC GCC ACC AAG AAG GTC AAG GCC GAG TAATCGGTTT        289
Arg Glu Gly Thr Ser Ala Thr Lys Lys Val Lys Ala Glu
80                  85                  90

ATCCATCACC TGGTGATCAG GGCGGGTAAT AATCTTTTGT TAGAGACTAT CCATGTTCTG     349

CTGCCGCATC AAACAAAAAA AAAAAAAAAA AA                                   381
```

(2) INFORMATION FOR SEQ ID NO:33:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:33:

```
Met Thr Lys Gly Thr Ser Ser Phe Gly Lys Arg His Thr Lys Thr His
1               5                   10                  15

Thr Ile Cys Arg Arg Cys Gly Asn Arg Ala Phe His Arg Gln Lys Lys
            20                  25                  30

Thr Cys Ala Gln Cys Gly Tyr Pro Ala Ala Lys Met Arg Ser Phe Asn
        35                  40                  45

Trp Gly Glu Lys Ala Lys Arg Arg Lys Thr Thr Gly Thr Gly Arg Met
    50                  55                  60
```

```
Gln His Leu Lys Asp Val Ser Arg Arg Phe Lys Asn Gly Phe Arg Glu
 65                  70                  75                  80

Gly Thr Ser Ala Thr Lys Lys Val Lys Ala Glu
                 85                  90
```

(2) INFORMATION FOR SEQ ID NO:34:

(i) SEQUENCE CHARACTERISTICS:
        (A) LENGTH: 473 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 19..321
        (D) OTHER INFORMATION: /product= "PRcDNA46"

(xi) SEQUENCE DESCRIPTION: SEQ ID NO:34:

```
CTCAAGAAGA AACTCGCC ATG CCT ACC CGA TTC TCC AAC ACC CGA AAG CAC         51
                    Met Pro Thr Arg Phe Ser Asn Thr Arg Lys His
                     1               5                      10

AGA GGA CAC GTC TCT GCC GGT CAC GGT CGT GTG GGA AAG CAC AGA AAG         99
Arg Gly His Val Ser Ala Gly His Gly Arg Val Gly Lys His Arg Lys
             15                  20                  25

CAC CCA GGA GGA CGA GGT CTT GCT GGA GGA CAG CAC CAC CAC CGA ACC        147
His Pro Gly Gly Arg Gly Leu Ala Gly Gly Gln His His His Arg Thr
         30                  35                  40

AAC TTC GAT AAG TAC CAC CCT GGA TAC TTC GGA AAG GTC GGA ATG AGG        195
Asn Phe Asp Lys Tyr His Pro Gly Tyr Phe Gly Lys Val Gly Met Arg
     45                  50                  55

CAC TTC CAC CTT ACC CGA NAC TCT TCC TGG TGC CCT ACC GTC AAC ATT        243
His Phe His Leu Thr Arg Xaa Ser Ser Trp Cys Pro Thr Val Asn Ile
 60                  65                  70                  75

GAC NAG CTC TGG ACT CTC GTC CCC GCT GAG GAG AAG AAG GAC TTC CCC        291
Asp Xaa Leu Trp Thr Leu Val Pro Ala Glu Glu Lys Lys Asp Phe Pro
                 80                  85                  90

AAC CAG GCT CGA CCT CGT CCC CGT TGT TGACACTTTG GCTCTCGGTT             338
Asn Gln Ala Arg Pro Arg Pro Arg Cys
             95                 100

ACGGCAATGT TCTTGGCAAG GGTCTACTTC CCCAGATCCC TTTAATCGTC AAGGCCCGAT     398

TCNTTTCCGC TCTTGCCGAG AANAANATCN ANGANGCTGG TTGGAATTCC TCTCCCCTTT     458

GTTCCCCCCN TAANG                                                      473
```

(2) INFORMATION FOR SEQ ID NO:35:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:35:

Met Pro Thr Arg Phe Ser Asn Thr Arg Lys His Arg Gly His Val Ser
 1               5                  10                  15

Ala Gly His Gly Arg Val Gly Lys His Arg Lys His Pro Gly Gly Arg
            20                  25                  30

Gly Leu Ala Gly Gly Gln His His His Arg Thr Asn Phe Asp Lys Tyr
        35                  40                  45

His Pro Gly Tyr Phe Gly Lys Val Gly Met Arg His Phe His Leu Thr
    50                  55                  60

Arg Xaa Ser Ser Trp Cys Pro Thr Val Asn Ile Asp Xaa Leu Trp Thr
65                  70                  75                  80

Leu Val Pro Ala Glu Glu Lys Lys Asp Phe Pro Asn Gln Ala Arg Pro
                85                  90                  95

Arg Pro Arg Cys
            100

(2) INFORMATION FOR SEQ ID NO:36:

(i) SEQUENCE CHARACTERISTICS:
        (A) LENGTH: 608 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 18..453
        (D) OTHER INFORMATION: /product= "PRcDNA64"

(xi) SEQUENCE DESCRIPTION: SEQ ID NO:36:

AAGACTCGTC GTTCAGC ATG TCC TCC GTC AAA GCC ACC AAA GGA AAG GGT         50
                   Met Ser Ser Val Lys Ala Thr Lys Gly Lys Gly
                    1               5                  10

CCC GCC GCC TCG GCT GAT GTT AAG GCC AAG GCC GCC AAG AAG GCT GCC        98
Pro Ala Ala Ser Ala Asp Val Lys Ala Lys Ala Ala Lys Lys Ala Ala
                15                  20                  25

CTC AAG GGT ACT CAG TCT ACT TCC ACC AGG AAG GTC CGA ACT TCG GTC       146
Leu Lys Gly Thr Gln Ser Thr Ser Thr Arg Lys Val Arg Thr Ser Val
            30                  35                  40

TCT TTC CAC CGA CCC AAG ACT CTC CGA CTT CCC CGA GCT CCC AAG TAC       194
Ser Phe His Arg Pro Lys Thr Leu Arg Leu Pro Arg Ala Pro Lys Tyr
        45                  50                  55

CCC CGA AAG TCG GTC CCT CAC GCC CCT CGA ATG GAT GAG TTC CGA ACT       242
Pro Arg Lys Ser Val Pro His Ala Pro Arg Met Asp Glu Phe Arg Thr
60                  65                  70                  75

ATC ATC CAC CCC TTG GCT ACC GAG TCC GCC ATG AAG AAG ATT GAG GAG       290
Ile Ile His Pro Leu Ala Thr Glu Ser Ala Met Lys Lys Ile Glu Glu
                80                  85                  90

CAC AAC ACC CTT GTG TTC ATC GTC GAT GTC AAG TCC AAC AAG CGA CAG       338
His Asn Thr Leu Val Phe Ile Val Asp Val Lys Ser Asn Lys Arg Gln
            95                  100                 105

```
ATC AAG GAC GCC GTC AAG AAG CTC TAC GAG GTC GAT ACC GTC CAC NTC      386
Ile Lys Asp Ala Val Lys Lys Leu Tyr Glu Val Asp Thr Val His Xaa
        110                 115                 120

AAC NCC TTG ATC ACC CCC GCC GGA AGG AAG AAG CTT ACG TCC GAC TTA      434
Asn Xaa Leu Ile Thr Pro Ala Gly Arg Lys Lys Leu Thr Ser Asp Leu
    125                 130                 135

CCC CCG ACC ACG ACG CTC T TAACGTTGCC AACAAGGCCG GCTACATCTA           483
Pro Pro Thr Thr Thr Leu
140                 145

ATCGACTCCA TCCCTTGGAT CGGTTCAGTT GTTTGGTTTG CATCCGGTTT CAGAGTTTGA    543

CGACCTTGAA ACTCNAANAC TTTGGATGCA TGTTTGAAAT TCTCNAAATA AAAAAAAAA     603

AAAAA                                                                608

(2) INFORMATION FOR SEQ ID NO:37:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:37:

Met Ser Ser Val Lys Ala Thr Lys Gly Lys Gly Pro Ala Ala Ser Ala
 1               5                  10                  15

Asp Val Lys Ala Lys Ala Ala Lys Lys Ala Ala Leu Lys Gly Thr Gln
                20                  25                  30

Ser Thr Ser Thr Arg Lys Val Arg Thr Ser Val Ser Phe His Arg Pro
            35                  40                  45

Lys Thr Leu Arg Leu Pro Arg Ala Pro Lys Tyr Pro Arg Lys Ser Val
        50                  55                  60

Pro His Ala Pro Arg Met Asp Glu Phe Arg Thr Ile Ile His Pro Leu
 65                 70                  75                  80

Ala Thr Glu Ser Ala Met Lys Lys Ile Glu Glu His Asn Thr Leu Val
                85                  90                  95

Phe Ile Val Asp Val Lys Ser Asn Lys Arg Gln Ile Lys Asp Ala Val
            100                 105                 110

Lys Lys Leu Tyr Glu Val Asp Thr Val His Xaa Asn Xaa Leu Ile Thr
        115                 120                 125

Pro Ala Gly Arg Lys Lys Leu Thr Ser Asp Leu Pro Pro Thr Thr Thr
    130                 135                 140

Leu
145

(2) INFORMATION FOR SEQ ID NO:38:

(i) SEQUENCE CHARACTERISTICS:
        (A) LENGTH: 466 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma
```

(ix) FEATURE:
    (A) NAME/KEY: CDS
    (B) LOCATION: 81..416
    (D) OTHER INFORMATION: /product= "PRcDNA68"

(xi) SEQUENCE DESCRIPTION: SEQ ID NO:38:

```
CTTTGAACCT CCAACCTCGG CATCAAGCAC TAGTCAGCCT CGGCTTAAAT CGATTCGTGT        60

AGCCTTTCAA ACTCGTAAAA ATG AAG CAC ATC GCC GCT TAC TTG CTC CTC          110
                      Met Lys His Ile Ala Ala Tyr Leu Leu Leu
                       1               5                  10

GCC ACC GGT GGA AAC NCC TCC CCC TCT GCC GCC GAT GTC AAG GCC CTC         158
Ala Thr Gly Gly Asn Xaa Ser Pro Ser Ala Ala Asp Val Lys Ala Leu
               15                  20                  25

CTT GCC ACC GTC GAC ATC GAG GCT GAT GAC GCC CGA CTT GAG ACC CTC         206
Leu Ala Thr Val Asp Ile Glu Ala Asp Asp Ala Arg Leu Glu Thr Leu
                30                  35                  40

ATC TCC GAG CTT AAC GGC AAG GAC TTG AAC ACC CTC ATC GCT GAG GGA         254
Ile Ser Glu Leu Asn Gly Lys Asp Leu Asn Thr Leu Ile Ala Glu Gly
            45                  50                  55

TCC GCC AAG CTC GCT TCC GTC CCC TCC GGA GGA GCC GCC TCT TCC GCT         302
Ser Ala Lys Leu Ala Ser Val Pro Ser Gly Gly Ala Ala Ser Ser Ala
    60                  65                  70

GCC CCC GCC GCC GCT GGA GGA GCC GCC GCC CCT GCC GCT GAG GAT AAG         350
Ala Pro Ala Ala Ala Gly Gly Ala Ala Ala Pro Ala Ala Glu Asp Lys
75                  80                  85                  90

AAG GAG GAG AAG GTC GAG GAC AAG GAG GAG TCT GAC GAC GAC ATG GGT         398
Lys Glu Glu Lys Val Glu Asp Lys Glu Glu Ser Asp Asp Asp Met Gly
                95                 100                 105

TTC GGA CTT TTC GAT TAAACTCCTT ACACCTTTTT CAAACTCTTC GTTGGCTCGA         453
Phe Gly Leu Phe Asp
            110

GGGGGGGCCC GGT                                                          466
```

(2) INFORMATION FOR SEQ ID NO:39:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:39:

```
Met Lys His Ile Ala Ala Tyr Leu Leu Leu Ala Thr Gly Gly Asn Xaa
 1               5                  10                  15

Ser Pro Ser Ala Ala Asp Val Lys Ala Leu Leu Ala Thr Val Asp Ile
                20                  25                  30

Glu Ala Asp Asp Ala Arg Leu Glu Thr Leu Ile Ser Glu Leu Asn Gly
            35                  40                  45

Lys Asp Leu Asn Thr Leu Ile Ala Glu Gly Ser Ala Lys Leu Ala Ser
        50                  55                  60

Val Pro Ser Gly Gly Ala Ala Ser Ser Ala Ala Pro Ala Ala Ala Gly
65                  70                  75                  80

Gly Ala Ala Ala Pro Ala Ala Glu Asp Lys Lys Glu Glu Lys Val Glu
                85                  90                  95

Asp Lys Glu Glu Ser Asp Asp Asp Met Gly Phe Gly Leu Phe Asp
            100                 105                 110
```

(2) INFORMATION FOR SEQ ID NO:40:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 49..501
        (D) OTHER INFORMATION: /product= "PRcDNA73"

(xi) SEQUENCE DESCRIPTION: SEQ ID NO:40:

```
CTTCCTCCCG TCAAGGCAAA CCTTCAGAAT CCTCTCAAGT CATTCAAC ATG GGA CGA        57
                                                     Met Gly Arg
                                                      1

GTC CGC ACC AAA ACC GTC AAG CGA GCT TCG CGA GTG ATG ATC GAG AAG        105
Val Arg Thr Lys Thr Val Lys Arg Ala Ser Arg Val Met Ile Glu Lys
      5              10                 15

TTC TAC CCT CGA CTC ACT CTT GAT TTC CAC ACC AAC AAG CGA ATC GCC        153
Phe Tyr Pro Arg Leu Thr Leu Asp Phe His Thr Asn Lys Arg Ile Ala
 20              25                 30                 35

GAC GAG GTT GCC ATC ATC CCC TCC AAG CGA CTT CGA AAC AAG ATC GCT        201
Asp Glu Val Ala Ile Ile Pro Ser Lys Arg Leu Arg Asn Lys Ile Ala
                 40                 45                 50

GGG TTC ACT ACC CAC TTG ATG AAG CGA ATC CAG AAG GGA CCC GTT CGA        249
Gly Phe Thr Thr His Leu Met Lys Arg Ile Gln Lys Gly Pro Val Arg
                     55                 60                 65

GGT ATC TCC TTC AAG CTT CAG GAG GAG GAG CGA GAG AGG AAG GAT CAG        297
Gly Ile Ser Phe Lys Leu Gln Glu Glu Glu Arg Glu Arg Lys Asp Gln
             70                 75                 80

TAC GTT CCT GAG GTC TCC GCC CTT GCC GCC CCT GAG CTG GGT TTG GAG        345
Tyr Val Pro Glu Val Ser Ala Leu Ala Ala Pro Glu Leu Gly Leu Glu
 85                 90                 95

GTT GAC CCC GAC ACC AAG GAT CTT CTC CGA TCC CTT GGC ATG GAC TCC        393
Val Asp Pro Asp Thr Lys Asp Leu Leu Arg Ser Leu Gly Met Asp Ser
100                105                110                115

ATC AAC GTC CAG GTC TCC GCT CCT ATC TCT TCC TAC GCT GCC CCC GAG        441
Ile Asn Val Gln Val Ser Ala Pro Ile Ser Ser Tyr Ala Ala Pro Glu
                120                125                130

CGA GGT CCC CGA GGT GCC GGA CGA NGT GGA CGA ATC GTC CCC GGA GCT        489
Arg Gly Pro Arg Gly Ala Gly Arg Xaa Gly Arg Ile Val Pro Gly Ala
                135                140                145

GGC CGA TAC TAAGTGTTTT CTTCAACCAN GGGATATTTG ATNATTCGCT                538
Gly Arg Tyr
        150

AGGCTTGAAA TTTTTTTATC ATTCTTCCTA TA                                    570
```

(2) INFORMATION FOR SEQ ID NO:41:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:41:

Met Gly Arg Val Arg Thr Lys Thr Val Lys Arg Ala Ser Arg Val Met
 1               5                  10                  15

Ile Glu Lys Phe Tyr Pro Arg Leu Thr Leu Asp Phe His Thr Asn Lys
                20                  25                  30

Arg Ile Ala Asp Glu Val Ala Ile Ile Pro Ser Lys Arg Leu Arg Asn
            35                  40                  45

Lys Ile Ala Gly Phe Thr Thr His Leu Met Lys Arg Ile Gln Lys Gly
        50                  55                  60

Pro Val Arg Gly Ile Ser Phe Lys Leu Gln Glu Glu Arg Glu Arg
65                  70                  75                  80

Lys Asp Gln Tyr Val Pro Glu Val Ser Ala Leu Ala Ala Pro Glu Leu
                85                  90                  95

Gly Leu Glu Val Asp Pro Asp Thr Lys Asp Leu Leu Arg Ser Leu Gly
                100                 105                 110

Met Asp Ser Ile Asn Val Gln Val Ser Ala Pro Ile Ser Ser Tyr Ala
            115                 120                 125

Ala Pro Glu Arg Gly Pro Arg Gly Ala Gly Arg Xaa Gly Arg Ile Val
        130                 135                 140

Pro Gly Ala Gly Arg Tyr
145                 150

(2) INFORMATION FOR SEQ ID NO:42:

(i) SEQUENCE CHARACTERISTICS:
        (A) LENGTH: 373 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 13..324
        (D) OTHER INFORMATION: /product= "PRcDNA76"

(xi) SEQUENCE DESCRIPTION: SEQ ID NO:42:

CCATCATCCA AC ATG CCT CCC AAA GTC AAG GCC AAG ACC GGT GTC GGT          48
              Met Pro Pro Lys Val Lys Ala Lys Thr Gly Val Gly
                1               5                  10

AAG ACC CAG AAG AAG AAG AAG TGG TCC AAG GGA AAG GTG AAG GAC AAG        96
Lys Thr Gln Lys Lys Lys Lys Trp Ser Lys Gly Lys Val Lys Asp Lys
        15                  20                  25

GCC GCC CAC CAC GTC GTT GTT GAT CAG GCC ACT TAC GAC AAG ATC GTT       144
Ala Ala His His Val Val Val Asp Gln Ala Thr Tyr Asp Lys Ile Val
            30                  35                  40

AAG GAG GTC CCC ACC TAC AAG TTG ATC TCC CAG TCT ATC TTG ATT GAC       192
Lys Glu Val Pro Thr Tyr Lys Leu Ile Ser Gln Ser Ile Leu Ile Asp
        45                  50                  55                  60

CGA CAC AAG GTT AAC GGT TCC GTC GCC CGA GCC GCT ATC CGA CAC CTT       240
Arg His Lys Val Asn Gly Ser Val Ala Arg Ala Ala Ile Arg His Leu
                65                  70                  75

-continued

```
GCC AAG GAG GGA TCC ATC AAG AAG ATT GTC CAC CAC AAC GGA CAG TGG        288
Ala Lys Glu Gly Ser Ile Lys Lys Ile Val His His Asn Gly Gln Trp
            80                  85                  90

ATC TAC ACC CGA GCC ACT GCC GCT CCT GAC GCA TAAATCTGAT GGATTTCATG      341
Ile Tyr Thr Arg Ala Thr Ala Ala Pro Asp Ala
        95                  100

GATCTTGAAA AATAAAAAAA AAAAAAAAAA AA                                     373
```

(2) INFORMATION FOR SEQ ID NO:43:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO:43:

```
Met Pro Pro Lys Val Lys Ala Lys Thr Gly Val Gly Lys Thr Gln Lys
 1               5                  10                  15

Lys Lys Lys Trp Ser Lys Gly Lys Val Lys Asp Lys Ala Ala His His
            20                  25                  30

Val Val Val Asp Gln Ala Thr Tyr Asp Lys Ile Val Lys Glu Val Pro
        35                  40                  45

Thr Tyr Lys Leu Ile Ser Gln Ser Ile Leu Ile Asp Arg His Lys Val
    50                  55                  60

Asn Gly Ser Val Ala Arg Ala Ala Ile Arg His Leu Ala Lys Glu Gly
 65                  70                  75                  80

Ser Ile Lys Lys Ile Val His His Asn Gly Gln Trp Ile Tyr Thr Arg
                85                  90                  95

Ala Thr Ala Ala Pro Asp Ala
            100
```

(2) INFORMATION FOR SEQ ID NO:44:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 13..435
        (D) OTHER INFORMATION: /product= "PRcDNA78"

(xi) SEQUENCE DESCRIPTION: SEQ ID NO:44:

```
AAAAAAGCCA AT ATG CTT ATC TCT AAA CAG AAC AGG AGG GCC ATC TTC          48
              Met Leu Ile Ser Lys Gln Asn Arg Arg Ala Ile Phe
               1               5                  10

GAG AAC CTC TTC AAG GAG GGA GTT GCC GTC GCC GCC AAG GAC TTC AAC        96
Glu Asn Leu Phe Lys Glu Gly Val Ala Val Ala Ala Lys Asp Phe Asn
            15                  20                  25
```

```
GCT GCC ACC CAC CCC GAG ATT GAG GGT GTC TCC AAC CTT GAG GTC ATC          144
Ala Ala Thr His Pro Glu Ile Glu Gly Val Ser Asn Leu Glu Val Ile
    30                  35                  40

AAG GCC ATG CAG TCT TTG ACC TCC AAG GGA TAC GTG AAG ACC CAG TTC          192
Lys Ala Met Gln Ser Leu Thr Ser Lys Gly Tyr Val Lys Thr Gln Phe
 45                  50                  55                  60

TCG TGG CAG TAC TAC TAC ACC CTC ACC CCT GAG GGT CTT GAC TAC              240
Ser Trp Gln Tyr Tyr Tyr Thr Leu Thr Pro Glu Gly Leu Asp Tyr
                 65                  70                  75

CTC CGA GAG TTC CTC CAC CTT CCC TCC GAG ATT GTC CCC AAC ACT CTC          288
Leu Arg Glu Phe Leu His Leu Pro Ser Glu Ile Val Pro Asn Thr Leu
                 80                  85                  90

AAG CGA CCC ACC CGA CCT GCC AAG GCC CAG GGT CCC GGA GGT GCC TAC          336
Lys Arg Pro Thr Arg Pro Ala Lys Ala Gln Gly Pro Gly Gly Ala Tyr
             95                 100                 105

CGA GCT CCC CGA GCC GAG GGT GCC GGT CGA GGA GAG TAC CGA CGA CGA          384
Arg Ala Pro Arg Ala Glu Gly Ala Gly Arg Gly Glu Tyr Arg Arg Arg
            110                 115                 120

GAG GAC GGT GCC GGT GCC TTC GGT GCC GGT CGA GGT GGA CCC CGA GCT          432
Glu Asp Gly Ala Gly Ala Phe Gly Ala Gly Arg Gly Gly Pro Arg Ala
125                 130                 135                 140

TAAATCCCAG AGCTTTTCTT TTTGTCGTTG CTGGGACTAT GGCATGATGA GCTGGCTTGC        492

AGAAAAAAAA AAAAAAAAA AA                                                  514

(2) INFORMATION FOR SEQ ID NO:45:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:45:

Met Leu Ile Ser Lys Gln Asn Arg Arg Ala Ile Phe Glu Asn Leu Phe
 1               5                  10                  15

Lys Glu Gly Val Ala Val Ala Ala Lys Asp Phe Asn Ala Ala Thr His
                20                  25                  30

Pro Glu Ile Glu Gly Val Ser Asn Leu Glu Val Ile Lys Ala Met Gln
             35                  40                  45

Ser Leu Thr Ser Lys Gly Tyr Val Lys Thr Gln Phe Ser Trp Gln Tyr
 50                  55                  60

Tyr Tyr Tyr Thr Leu Thr Pro Glu Gly Leu Asp Tyr Leu Arg Glu Phe
 65                  70                  75                  80

Leu His Leu Pro Ser Glu Ile Val Pro Asn Thr Leu Lys Arg Pro Thr
                 85                  90                  95

Arg Pro Ala Lys Ala Gln Gly Pro Gly Gly Ala Tyr Arg Ala Pro Arg
            100                 105                 110

Ala Glu Gly Ala Gly Arg Gly Glu Tyr Arg Arg Arg Glu Asp Gly Ala
            115                 120                 125

Gly Ala Phe Gly Ala Gly Arg Gly Gly Pro Arg Ala
            130                 135                 140

(2) INFORMATION FOR SEQ ID NO:46:

(i) SEQUENCE CHARACTERISTICS:
        (A) LENGTH: 437 base pairs
        (B) TYPE: nucleic acid
        (C) STRANDEDNESS: double
        (D) TOPOLOGY: linear
```

```
      (ii) MOLECULE TYPE: cDNA (iii) HYPOTHETICAL: NO (iv) ANTI-SENSE: NO (vi) ORIGINAL SOURCE:
           (A) ORGANISM: Phaffia rhodozyma (ix) FEATURE:
           (A) NAME/KEY: CDS
           (B) LOCATION: 30..308
           (D) OTHER INFORMATION: /product= "PRcDNA85"

(xi) SEQUENCE DESCRIPTION: SEQ ID NO:46:

CTCCCTCAAG AAATCAACCA CCGCACATC ATG TCC AAG CGA ACC AAG AAA GTT           53
                                   Met Ser Lys Arg Thr Lys Lys Val
                                    1               5

GGA ATC ACC GGA AAG TAC GGA GTC CGA TAC GGA GCT TCC CTC CGA AAG         101
Gly Ile Thr Gly Lys Tyr Gly Val Arg Tyr Gly Ala Ser Leu Arg Lys
         10                  15                  20

ACC GTC AAG AAG NTG GAG GTC TGG CAG CAC GGT ACC TAC ACC TGT GAC         149
Thr Val Lys Lys Xaa Glu Val Trp Gln His Gly Thr Tyr Thr Cys Asp
 25                  30                  35                  40

TTC TGC GGA AAG GAC GCC GTC AAG CGA ACC GCT GTT GGT ATC TGG AAG         197
Phe Cys Gly Lys Asp Ala Val Lys Arg Thr Ala Val Gly Ile Trp Lys
                 45                  50                  55

TGC CGA GGA TGC CGA AAG ACC ACC GCC GGT GGT GCT TGG CAG CTT CAG         245
Cys Arg Gly Cys Arg Lys Thr Thr Ala Gly Gly Ala Trp Gln Leu Gln
                     60                  65                  70

ACC ACC GCC GCT CTC ACC GTC AAG TCC ACC ACT CGA CGA CTC CGA GAG         293
Thr Thr Ala Ala Leu Thr Val Lys Ser Thr Thr Arg Arg Leu Arg Glu
                         75                  80                  85

CTC AAG GAG GTT TAAATTGAAT TCTGCACAAA GACAAAACTG TTGCGGGCGG             345
Leu Lys Glu Val
             90

GAGAGAGTGG ATTCATTCTT TTTTTTTGTA GATCTGAAGG GATGCCATGT CAACCCTTTC       405

GTTCCCCAAA AAAAAAAAAA AAAAAAAAAA AA                                     437

(2) INFORMATION FOR SEQ ID NO:47:

(i) SEQUENCE CHARACTERISTICS:
         (A) LENGTH: 92 amino acids
         (B) TYPE: amino acid
         (D) TOPOLOGY: linear (ii) MOLECULE TYPE: protein (xi) SEQUENCE DESCRIPTION: SEQ ID NO:47:

Met Ser Lys Arg Thr Lys Lys Val Gly Ile Thr Gly Lys Tyr Gly Val
 1               5                  10                  15

Arg Tyr Gly Ala Ser Leu Arg Lys Thr Val Lys Lys Xaa Glu Val Trp
                 20                  25                  30

Gln His Gly Thr Tyr Thr Cys Asp Phe Cys Gly Lys Asp Ala Val Lys
                 35                  40                  45

Arg Thr Ala Val Gly Ile Trp Lys Cys Arg Gly Cys Arg Lys Thr Thr
         50                  55                  60

Ala Gly Gly Ala Trp Gln Leu Gln Thr Thr Ala Ala Leu Thr Val Lys
 65                  70                  75                  80

Ser Thr Thr Arg Arg Leu Arg Glu Leu Lys Glu Val
                 85                  90
```

(2) INFORMATION FOR SEQ ID NO:48:

(i) SEQUENCE CHARACTERISTICS:
        (A) LENGTH: 509 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 35..400
        (D) OTHER INFORMATION: /product= "PRcDNA87"

(xi) SEQUENCE DESCRIPTION: SEQ ID NO:48:

```
GGAAGACCTC ACAGCAAGAC TAAGACTCTC AAAC ATG GCT ACC AAG ACC GGC          52
                                     Met Ala Thr Lys Thr Gly
                                       1               5

AAG ACT CGA TCC GCT CTC CAG GAC GTC GTT ACT CGG GAG TAC ACC ATC        100
Lys Thr Arg Ser Ala Leu Gln Asp Val Val Thr Arg Glu Tyr Thr Ile
             10                  15                  20

CAC CTC CAC AAG TAC GTT CAC GGA AGG TCT TTC AAG AAG CGA GCT CCT        148
His Leu His Lys Tyr Val His Gly Arg Ser Phe Lys Lys Arg Ala Pro
         25                  30                  35

TGG GCT GTC AAG TCC ATC CAG GAG TTT GCT CTC AAG TCG ATG GGA ACC        196
Trp Ala Val Lys Ser Ile Gln Glu Phe Ala Leu Lys Ser Met Gly Thr
     40                  45                  50

CGA GAT GTC CGA ATT GAC CCC AAG TTG AAC CAG GCC GTC TGG GGA CAG        244
Arg Asp Val Arg Ile Asp Pro Lys Leu Asn Gln Ala Val Trp Gly Gln
 55                  60                  65                  70

GGT GTC AAG AAC CCC CCC AAG CGA CTC CGA ATC CGA CTT GAG CGA AAG        292
Gly Val Lys Asn Pro Pro Lys Arg Leu Arg Ile Arg Leu Glu Arg Lys
             75                  80                  85

CGA AAC GAC GAG GAG GAT GCT AAG GAC AAG CTC TAC ACT CTT GCT ACC        340
Arg Asn Asp Glu Glu Asp Ala Lys Asp Lys Leu Tyr Thr Leu Ala Thr
         90                  95                 100

GTC GTC CCC GGA GTC ACC AAC TTC AAG GGT CTC CAA ACC GTT GTC GTT        388
Val Val Pro Gly Val Thr Asn Phe Lys Gly Leu Gln Thr Val Val Val
    105                 110                 115

GAC ACC GAG TAATTTTGTC TTGGATTTTC ATGACGGTCG ATTCAGCTGT                437
Asp Thr Glu
    120

TTCTTGGCGC CATTCTTCTT ATGCACTCTG ATGCCTTTCA CGACCCNTTT TTNTTTCTNA      497

TAAATAAAAA AA                                                          509
```

(2) INFORMATION FOR SEQ ID NO:49:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:49:

```
Met Ala Thr Lys Thr Gly Lys Thr Arg Ser Ala Leu Gln Asp Val Val
  1               5                  10                  15
```

```
Thr Arg Glu Tyr Thr Ile His Leu His Lys Tyr Val His Gly Arg Ser
         20                  25                  30

Phe Lys Lys Arg Ala Pro Trp Ala Val Lys Ser Ile Gln Glu Phe Ala
         35                  40                  45

Leu Lys Ser Met Gly Thr Arg Asp Val Arg Ile Asp Pro Lys Leu Asn
 50                  55                  60

Gln Ala Val Trp Gly Gln Gly Val Lys Asn Pro Pro Lys Arg Leu Arg
 65                  70                  75                  80

Ile Arg Leu Glu Arg Lys Arg Asn Asp Glu Glu Asp Ala Lys Asp Lys
                 85                  90                  95

Leu Tyr Thr Leu Ala Thr Val Val Pro Gly Val Thr Asn Phe Lys Gly
                100                 105                 110

Leu Gln Thr Val Val Val Asp Thr Glu
        115                 120

(2) INFORMATION FOR SEQ ID NO:50:

(i) SEQUENCE CHARACTERISTICS:
        (A) LENGTH: 542 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Phaffia rhodozyma (ix) FEATURE:
        (A) NAME/KEY: CDS
        (B) LOCATION: 18..443
        (D) OTHER INFORMATION: /product= "PRcDNA95"

(xi) SEQUENCE DESCRIPTION: SEQ ID NO:50:
```

```
AGTCGCTATA CATCAAG ATG TCC GTC GCT GTC CAG ACT TTC GGT AAG AAG        50
                   Met Ser Val Ala Val Gln Thr Phe Gly Lys Lys
                    1               5                  10

AAG ACT GCC ACC GCT GTG GCC CAC GCC ACC CCT GGC CGA GGT CTC ATC       98
Lys Thr Ala Thr Ala Val Ala His Ala Thr Pro Gly Arg Gly Leu Ile
             15                  20                  25

CGA CTT AAC GGA CAG CCT ATC TCA CTT GCC GAG CCT GCT CTC CTC CGA      146
Arg Leu Asn Gly Gln Pro Ile Ser Leu Ala Glu Pro Ala Leu Leu Arg
         30                  35                  40

TAC AAG TAC TAC GAG CCT ATC CTC GTC ATC GGA GCT GAG AAG ATC AAC      194
Tyr Lys Tyr Tyr Glu Pro Ile Leu Val Ile Gly Ala Glu Lys Ile Asn
 45                  50                  55

CAG ATC GAC ATC CGA CTC AAG GTC AAG GGT GGA GGA CAC GTC TCC CAG      242
Gln Ile Asp Ile Arg Leu Lys Val Lys Gly Gly Gly His Val Ser Gln
 60                  65                  70                  75

GTG TAC GCC GTC CGA CAG GCC ATC GGT AAG GCC ATC GTC GCT TAC TAC      290
Val Tyr Ala Val Arg Gln Ala Ile Gly Lys Ala Ile Val Ala Tyr Tyr
                 80                  85                  90

GCT AAG AAC GTC GAT GCC GCC TCT GCC CTC GAG ATC AAG AAG GCT CTC      338
Ala Lys Asn Val Asp Ala Ala Ser Ala Leu Glu Ile Lys Lys Ala Leu
                 95                 100                 105

GTC GCC TAC GAC CGA ACC CTC CTC ATC GCC GAT CCC CGA CGA ATG GAG      386
Val Ala Tyr Asp Arg Thr Leu Leu Ile Ala Asp Pro Arg Arg Met Glu
            110                 115                 120
```

```
CCC AAG AAG TTC GGA GGA CCC GGA GCC CGA GCC CGA GTC CAG AAG TCT        434
Pro Lys Lys Phe Gly Gly Pro Gly Ala Arg Ala Arg Val Gln Lys Ser
    125                 130                 135

TAC CGA TAAAAAGTGT TTGTCTTGTG GTCTGGCGGG TCATCTATCC AACATCTTTG         490
Tyr Arg
140

GAAAANANTT GTTTGGGTCA TATGTCATGC CTCTTTATGG AAAAAAAAAA AA              542

(2) INFORMATION FOR SEQ ID NO:51:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:51:

Met Ser Val Ala Val Gln Thr Phe Gly Lys Lys Lys Thr Ala Thr Ala
  1               5                  10                  15

Val Ala His Ala Thr Pro Gly Arg Gly Leu Ile Arg Leu Asn Gly Gln
                 20                  25                  30

Pro Ile Ser Leu Ala Glu Pro Ala Leu Leu Arg Tyr Lys Tyr Tyr Glu
             35                  40                  45

Pro Ile Leu Val Ile Gly Ala Glu Lys Ile Asn Gln Ile Asp Ile Arg
         50                  55                  60

Leu Lys Val Lys Gly Gly Gly His Val Ser Gln Val Tyr Ala Val Arg
 65                  70                  75                  80

Gln Ala Ile Gly Lys Ala Ile Val Ala Tyr Tyr Ala Lys Asn Val Asp
                 85                  90                  95

Ala Ala Ser Ala Leu Glu Ile Lys Lys Ala Leu Val Ala Tyr Asp Arg
                100                 105                 110

Thr Leu Leu Ile Ala Asp Pro Arg Arg Met Glu Pro Lys Lys Phe Gly
             115                 120                 125

Gly Pro Gly Ala Arg Ala Arg Val Gln Lys Ser Tyr Arg
        130                 135                 140
```